US011078543B2

(12) United States Patent
Ahlquist et al.

(10) Patent No.: US 11,078,543 B2
(45) Date of Patent: Aug. 3, 2021

(54) DETECTING PANCREATIC HIGH-GRADE DYSPLASIA

(71) Applicant: MAYO FOUNDATION FOR MEDICAL EDUCATION AND RESEARCH, Rochester, MN (US)

(72) Inventors: David A. Ahlquist, Rochester, MN (US); William R. Taylor, Lake City, MN (US); John B. Kisiel, Rochester, MN (US); Tracy C. Yab, Rochester, MN (US); Douglas W. Mahoney, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 28 days.

(21) Appl. No.: 16/093,534

(22) PCT Filed: Apr. 13, 2017

(86) PCT No.: PCT/US2017/027439
§ 371 (c)(1),
(2) Date: Oct. 12, 2018

(87) PCT Pub. No.: WO2017/180886
PCT Pub. Date: Oct. 19, 2017

(65) Prior Publication Data
US 2019/0161804 A1 May 30, 2019

Related U.S. Application Data

(60) Provisional application No. 62/322,610, filed on Apr. 14, 2016.

(51) Int. Cl.
C12Q 1/68 (2018.01)
C07H 21/04 (2006.01)
C12Q 1/6886 (2018.01)

(52) U.S. Cl.
CPC ...... *C12Q 1/6886* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

| | | |
|---|---|---|
| 5,352,775 A | 10/1994 | Albertsen |
| 5,362,623 A | 11/1994 | Vogelstein |
| 5,527,676 A | 6/1996 | Vogelstein |
| 5,541,308 A | 7/1996 | Hogan |
| 5,648,212 A | 7/1997 | Albertsen |
| 5,670,325 A | 9/1997 | Lapidus et al. |
| 5,691,454 A | 11/1997 | Albertsen |
| 5,741,650 A | 4/1998 | Lapidus et al. |
| 5,783,666 A | 7/1998 | Albertsen |
| 5,786,146 A | 7/1998 | Herman |
| 5,891,651 A | 4/1999 | Roche |
| 5,928,870 A | 7/1999 | Lapidus et al. |
| 5,952,178 A | 9/1999 | Lapidus et al. |
| 5,955,263 A | 9/1999 | Vogelstein |
| 6,020,137 A | 2/2000 | Lapidus et al. |
| RE36,713 E | 5/2000 | Vogelstein |
| 6,090,566 A | 7/2000 | Vogelstein |
| 6,114,124 A | 9/2000 | Albertsen |
| 6,235,470 B1 | 5/2001 | Sidransky |
| 6,245,515 B1 | 6/2001 | Vogelstein |
| 6,413,727 B1 | 7/2002 | Albertsen |
| 6,630,314 B2 | 10/2003 | Nair et al. |
| 6,677,312 B1 | 1/2004 | Vogelstein |
| 6,800,617 B1 | 10/2004 | Vogelstein |
| RE38,916 E | 12/2005 | Vogelstein |
| 7,037,650 B2 | 5/2006 | Gonzalgo et al. |
| 7,087,583 B2 | 8/2006 | Vogelstein |
| 7,267,955 B2 | 9/2007 | Vogelstein |
| 7,368,233 B2 | 5/2008 | Shuber et al. |
| 7,432,050 B2 | 10/2008 | Markowitz |
| 7,485,402 B2 | 2/2009 | Arai |
| 7,485,418 B2 | 2/2009 | Goggins |
| 7,485,420 B2 | 2/2009 | Markowitz |
| 8,114,587 B2 | 2/2012 | Gite et al. |
| 8,361,720 B2 | 1/2013 | Oldham-Haltom |
| 8,673,555 B2 | 3/2014 | Taylor |
| 8,808,990 B2 | 8/2014 | Lidgard et al. |

(Continued)

FOREIGN PATENT DOCUMENTS

| | | |
|---|---|---|
| EP | 2391729 | 12/2011 |
| WO | WO 00/26401 | 5/2000 |

(Continued)

OTHER PUBLICATIONS

Abbaszadegan, "Stool-based DNA testing, a new noninvasive method for colorectal cancer screening, the first report from Iran," World Journal of gastroenterology: WJG, vol. 13, p. 1528-1533, 2007.
Ahlquist D et al. (2010) "Next Generation Stool DNA Testing for Detection of Colorectal Neoplasia—Early Marker Evaluation", presented at Colorectal Cancer: Biology to Therapy, American Association for Cancer Research, 1 page.
Ahlquist D.A. et al., "Novel use of hypermethylated DNA markers in stool for detection of colorectal cancer: a feasibility study." Gastroenterology, 2002;122(Suppl):A40.
Ahlquist D.A., et al., "Colorectal cancer screening by detection of altered human DNA in stool: feasibility of a multitarget assay panel." Gastroenterology, 2000, 119(5):1219-27.
Ahlquist et al., "Next-generation stool DNA test accurately detects colorectal cancer and large adenomas." Gastroenterology (2012), 142, pp. 248-256.

(Continued)

*Primary Examiner* — Jeanine A Goldberg
(74) *Attorney, Agent, or Firm* — Casimir Jones, SC; Robert A. Goetz

(57) ABSTRACT

Provided herein is technology for pancreatic high-grade dysplasia screening and particularly, but not exclusively, to methods, compositions, and related uses for detecting the presence of pancreatic high-grade dysplasia (IPMN-HGD, PanIN-3, or PDAC).

7 Claims, 24 Drawing Sheets

Specification includes a Sequence Listing.

(56) References Cited

U.S. PATENT DOCUMENTS

| | | | |
|---|---|---|---|
| 8,969,046 | B2 | 3/2015 | Van Engeland et al. |
| 8,980,107 | B2 | 3/2015 | Domanico et al. |
| 8,993,341 | B2 | 3/2015 | Bruinsma et al. |
| 8,999,176 | B2 | 4/2015 | Domanico et al. |
| 9,000,146 | B2 | 4/2015 | Bruinsma et al. |
| 9,121,070 | B2 | 9/2015 | Taylor |
| 9,399,800 | B2 | 7/2016 | Taylor |
| 9,506,116 | B2 * | 11/2016 | Ahlquist ............. C12Q 1/6886 |
| 9,632,093 | B2 | 4/2017 | Taylor |
| 9,803,249 | B2 | 10/2017 | Taylor |
| 9,994,911 | B2 * | 6/2018 | Ahlquist ............. C12Q 1/6886 |
| 10,435,755 | B2 * | 10/2019 | Ahlquist ............. C12Q 1/6883 |
| 10,683,555 | B2 * | 6/2020 | Ahlquist ............. C12Q 1/6886 |
| 2003/0143606 | A1 | 7/2003 | Olek et al. |
| 2003/0224040 | A1 | 12/2003 | Baylin et al. |
| 2004/0234960 | A1 | 11/2004 | Hogan |
| 2006/0253259 | A1 | 11/2006 | Fernandez |
| 2007/0054295 | A1 | 3/2007 | Spivack |
| 2008/0039413 | A1 | 2/2008 | Morris et al. |
| 2008/0081333 | A1 | 4/2008 | Mori et al. |
| 2008/0213870 | A1 | 9/2008 | Cao et al. |
| 2009/0208505 | A1 | 8/2009 | Samuels |
| 2010/0167940 | A1 | 7/2010 | Feinberg |
| 2010/0317000 | A1 | 12/2010 | Zhu |
| 2011/0136687 | A1 | 6/2011 | Olek et al. |
| 2011/0183328 | A1 | 7/2011 | Taylor et al. |
| 2011/0287968 | A1 | 11/2011 | Weinhausel et al. |
| 2011/0318738 | A1 | 12/2011 | Jones et al. |
| 2012/0009597 | A1 | 1/2012 | Lao-Sirieix et al. |
| 2012/0034605 | A1 | 2/2012 | Hinoda et al. |
| 2012/0122088 | A1 | 5/2012 | Zou |
| 2012/0122106 | A1 | 5/2012 | Zou |
| 2012/0164110 | A1 | 6/2012 | Feinberg et al. |
| 2012/0164238 | A1 | 6/2012 | Louwagie |
| 2013/0012410 | A1 | 1/2013 | Zou et al. |
| 2013/0022974 | A1 | 1/2013 | Chinnaiyan |
| 2013/0065228 | A1 | 3/2013 | Hinoue |
| 2013/0109035 | A1 | 5/2013 | Das et al. |
| 2013/0244235 | A1 | 9/2013 | Ahlquist et al. |
| 2013/0288247 | A1 | 10/2013 | Mori et al. |
| 2014/0057262 | A1 | 2/2014 | Ahlquist et al. |
| 2014/0137274 | A1 | 5/2014 | Ishikawa |
| 2014/0162894 | A1 | 6/2014 | Hatchwell |
| 2014/0193813 | A1 | 7/2014 | Bruinsma |
| 2014/0194607 | A1 | 7/2014 | Bruinsma |
| 2014/0194608 | A1 | 7/2014 | Bruinsma |
| 2014/0274748 | A1 * | 9/2014 | Ahlquist ............. C12Q 1/6886 506/7 |
| 2014/0358448 | A1 | 12/2014 | Tai et al. |
| 2015/0275314 | A1 | 1/2015 | Ahlquist et al. |
| 2015/0126374 | A1 | 5/2015 | Califano |
| 2015/0240318 | A1 | 8/2015 | Van Engeland et al. |
| 2016/0040246 | A1 * | 2/2016 | Ahlquist ............. C12Q 1/6886 506/2 |
| 2016/0090634 | A1 | 3/2016 | Kisiel et al. |
| 2016/0194723 | A1 | 7/2016 | Louwagie |
| 2018/0037958 | A1 * | 2/2018 | Ahlquist .......... G01N 33/57407 |
| 2018/0258498 | A1 * | 9/2018 | Ahlquist ............. C12Q 1/6886 |
| 2020/0172982 | A1 * | 6/2020 | Ahlquist .......... G01N 33/57407 |

FOREIGN PATENT DOCUMENTS

| | | |
|---|---|---|
| WO | WO 2007/116417 | 10/2007 |
| WO | WO 2008/084219 | 7/2008 |
| WO | WO 2010/086389 | 8/2010 |
| WO | WO 2010/089538 | 8/2010 |
| WO | WO 2011/119934 | 9/2011 |
| WO | WO 2011/126768 | 10/2011 |
| WO | WO 2012/088298 | 6/2012 |
| WO | WO 2012/155072 | 11/2012 |
| WO | WO 2012/175562 | 12/2012 |
| WO | WO-2014159652 A2 * | 10/2014 ............ C12Q 1/6886 |
| WO | WO 2016/097120 | 6/2016 |
| WO | WO-2016160454 A1 * | 10/2016 ....... G01N 33/57407 |

OTHER PUBLICATIONS

Ahlquist et al., 1984, "HemoQuant, a new quantitative assay for fecal hemoglobin. Comparison with Hemoccult." Ann Intern Med, 101: 297-302.

Ahlquist et al., 1985, "Fecal blood levels in health and disease. A study using HemoQuant." N Engl J Med, 312: 1422-8.

Ahlquist et al., 1989, "Patterns of occult bleeding in asymptomatic colorectal cancer." Cancer, 63: 1826-30.

Ahlquist et al., 1993, "Accuracy of fecal occult blood screening for colorectal neoplasia. A prospective study using Hemoccult and HemoQuant tests." JAMA, 269: 1262-7.

Ahlquist et al., 2000, "Colorectal cancer screening by detection of altered human DNA in stool: feasibility of a multitarget assay panel." Gastroenterology, 119: 1219-27.

Ahlquist et al., 2008, "Stool DNA and occult blood testing for screen detection of colorectal neoplasia." Ann Intern Med, 149: 441-501.

Allison et al., 2007, "Screening for colorectal neoplasms with new fecal occult blood tests: update on performance characteristics." J Natl Cancer Inst, 99: 1462-70.

Anderson et al. Am. J. of Gastroenterology, Abstracts S1033, Oct. 2015.

Asai et al. "IKZF1 deletion is associated with a poor outcome in pediatric B-cell precursor acute lymphoblastic leukemia in Japan." Cancer Med. 2013; 2:412-9.

Aust De, "Mutations of the BRAF gene in ulcerative colitis-related colorectal carcinoma." Int. J. Cancer (2005), 115, pp. 673-677.

Azuara et al. "Novel Methylation Panel for the Early Detection of Colorectal Tumors in Stool DNA." Clinical Colorectal Cancer, vol. 9, No. 3, pp. 168-176, Jul. 2010.

Baxter, Eva "Investigating the association between BRAFv600E and methylation in sporadic colon cancer" PhD The University of Edinburgh, 2011.

Belinsky S.A., et al., "Promoter Hypermethylation of Multiple Genes in Sputum Precedes Lung Cancer Incidence in a High-Risk Cohort." Cancer Res, 2006;66:3338-44.

Bell et al., "c-Ki-ras gene mutations in dysplasia and carcinomas complicating ulcerative colitis." Br J Cancer (1991), 64, pp. 174-178.

Biankin et al. (2003) "Molecular pathogenesis of precursor lesions of pancreatic ductal adenocarcinoma" Pathology 35:14-24.

Brune, et al. (2008). "Genetic and epigenetic alterations of familial pancreatic cancers." Cancer Epidemiol Biomarkers Prev. 17 (12): 3536-3542.

Buck et al. "Design Strategies and Performance of Custom DNA Sequencing Primers" Biotechniques, 1999, 27(3): 528-536.

Cairns et al., "Guidelines for colorectal cancer screening and surveillance in moderate and high risk groups." Gut (2010); 59, pp. 666-689.

Cameron et al (1995) "Adenocarcinoma of the esophagogastric junction and Barrett's esophagus" Gastroenterology 109: 1541-1546.

Cameron et al. Blood, vol. 94, No. 7, pp. 2445-2451, Oct. 1999.

Camoes et al. "Potential downstream target genes of aberrant ETS transcription factors are differentially affected in Ewing's sarcoma and prostate carcinoma." PLoS One. 2012;7:e49819.

Campbell et al. "Aberrant expression of the neuronal transcription factor FOXP2 in neoplastic plasma cells." British journal of haematology. 2010; 149:221-30.

Chen "Expression and promoter methylation analysis of ATP-binding cassette genes in pancreatic cancer" Oncology Reports, 2012, 27:265-269.

Chen W.D., et al., "Detection in Fecal DNA of Colon Cancer—Specific Methylation of the Nonexpressed Vimentin Gene." J Natl Cancer Inst 2005;97:1124-32.

Crespi et al. "Colorectal cancer: a spreading but preventable disease" European Journal of Oncology. vol. 13(1). Mar. 2008. pp. 21-32.

De Kok, 2003, "Quantification and integrity analysis of DNA in the stool of colorectal cancer patients may represent a complex alternative to fecal occult blood testing." Clin Chem, 49: 2112-3.

(56) References Cited

OTHER PUBLICATIONS

Eads, et al. (1999). "CpG island hypermethylation in human colorectal tumors is not associated with DNA methyltransferase overexpression." Cancer Res. 59: 2302-2306.
Ebert M.P., et al., "Aristaless-like homeobox-4 gene methylation is a potential marker for colorectal adenocarcinomas." Gastroenterology 2006;131:1418-30.
Edge, S.; Fritz, A.G.; Greene, F.L.; Trotti, A. (Eds.), AJCC Cancer Staging Manual. 7th ed: Springer, New York; 2010; Book—only table of contents provided.
Esteller et al. "Inactivation of Glutathione S-Transferase P1 Gene by Promoter Hypermethylation in Human Neoplasia" Cancer Resarch, vol. 58, pp. 4515-4518, Oct. 1998.
Feng "Conservation and divergence of methylation patterning in plants and animals" PNAS 2010 vol. 107, No. 19, pp. 8689-8694.
Garrity-Park et al. "Methylation status of genes in non-neoplastic mucosa from patients with ulcerative colitis-associated colorectal cancer." Am J Gastroenterol (2010), 105, pp. 1610-1619.
Glockner, et al. (2009). "Methylation of TFPI2 in stool DNA: a potential novel biomarker for the detection of colorectal cancer." Cancer Res. 69: 4691-4699.
Goggins, M. "Molecular markers of early pancreatic cancer." J Clin Oncol 2005; 23: 4524.
Gonzalgo, et al. (1997) "Identification and characterization of differentially methylated regions of genomic DNA by methylation-sensitive arbitrarily primed PCR." Cancer Res. 57: 594-599.
Gonzalgo, et al. (1997). "Rapid quantitation of methylation differences at specific sites using methylation-sensitive single nucleotide primer extension (Ms-SNuPE)." Nucleic Acids Res. 25 (12): 2529-2531.
Grady W.M., et al., "Detection of Aberrantly Methylated hMLH1 Promoter DNA in the Serum of Patients with Microsatellite Unstable Colon Cancer 1." Cancer Res, 2001;61:900-2.
Grutzmann et al., "Sensitive Detection of Colorectal Cancer in Peripheral Blood by Septin 9 DNA Methylation Assay." PLoS ONE (2008), 3:e3759.
Gu et al. "Genome-scale DNA methylation mapping of clinical samples at single-nucleotide resolution." Nat Methods. 2010; 7:133-6.
Gu, et al. (2011). "Preparation of reduced representation bisulfite sequencing libraries for genome-scale DNA methylation profiling." Nature Protocols. 6 (4): 468-481.
Gurung et al. "Menin epigenetically represses Hedgehog signaling in MEN1 tumor syndrome." Cancer research. 2013;73:2650-8.
Guzinska-Ustymowicz et al., (2009), "Correlation between proliferation makers: PCNA, Ki-67, MCM-2 and antiapoptopic protein Bcl2 in colorectal cancer," Anticancer Research. 29:3049-3052.
Hardcastle et al., 1996, "Randomised controlled trial of faecal-occult-blood screening for colorectal cancer." Lancet, 348: 1472-7.
Harewood et al., 2000, "Fecal occult blood testing for iron deficiency: a reappraisal." Dig Dis, 18(2): 75-82.
Harewood et al., 2002, "Detection of occult upper gastrointestinal tract bleeding: performance differences in fecal occult blood tests." Mayo Clin Proc, 77: 23-28.
Heresbach et al., 2006, "Review in depth and meta-analysis of controlled trials on colorectal cancer screening by faecal occult blood test." Eur J Gastroenterol Hepatol, 18: 427-33.
Herman, et al. (1996). "Methylation-specific PCR: A novel PCR assay for methylation status of CpG islands." Proc. Natl. Acad. Sci. USA. 93: 9821-9826.
Hibi et al. (2010) "Methylation of the TFPI2 gene is frequently detected in advanced gastric carcinoma" Anticancer Res 30: 4131-3.
Hibi, et al. (2010). "Methylation of TFPI2 gene is frequently detected in advanced well-differentiated colorectal cancer." Anticancer Res. 30: 1205-1207.
Hirota et al., "pS2 expression as a possible diagnostic marker of colorectal carcinoma in ulcerative colitis." Oncol Rep (2000), 7, pp. 233-239.
Hoang et al., 1997, "BAT-26, an indicator of the replication error phenotype in colorectal cancers and cell lines." Cancer Res, 57: 300-3.
Holzmann et al., "Comparative analysis of histology, DNA content, p53 and Ki-ras mutations in colectomy specimens with long-standing ulcerative colitis." Int J Cancer (1998) 76, pp. 1-6.
Hong, et al. (2008). "Multiple genes are hypermethylated in intraductal papillary mucinous neoplasms of the pancreas." Mod Pathol. 21 912): 1499-1507.
Hoque M.O., et al., "Quantitative methylation-specific polymerase chain reaction gene patterns in urine sediment distinguish prostate cancer patients from control subjects." J Clin Oncol, 2005;23:6569-75.
Howe, et al., "Annual report to the nation on the status of cancer, 1975-2003, featuring cancer among U.S. Hispanic/Latino populations." Cancer (2006) 107, pp. 1711-1742.
Imperiale et al. "Multitarget Stool DNA Testing for Colorectal-Cancer Screening" New England Journal of Medicine, vol. 370, No. 14, Apr. 3, 2014, pp. 1287-1297.
Imperiale et al., "Fecal DNA versus fecal occult blood for colorectal-cancer screening in an average-risk population." N Engl J Med (2004), 351, pp. 2704-2714.
International Search Report and Written Opinion dated Dec. 28, 2011 from International Patent Application No. PCT/US2011/029959, international filing date Mar. 25, 2011.
International Search Report and Written Opinion, Int'l Patent Application No. PCT/US2015/022749, dated Aug. 19, 2015, 12 pages.
International Search Report and Written Opinion, Int'l Patent Application No. PCT/US2015/022751, dated Aug. 26, 2015, 25 pages.
International Search Report dated Jun. 10, 2013 from related International Patent Application No. PCT/US2013/027227.
Issa et al., "Accelerated Age-related CpG Island Methylation in Ulcerative Colitis." Cancer Res (2001), 61, pp. 3573-3577.
Itzkowitz et al. "Diagnosis and management of dysplasia in patients with inflammatory bowel diseases." Gastroenterology (2004) 126, pp. 1634-1648.
Itzkowitz S.H., et al., "Improved fecal DNA test for colorectal cancer screening." Clin Gastroenterol Hepatol 2007;5:111-7.
Jacobs et al. "Dysregulated methylation at imprinted genes in prostate tumor tissue detected by methylation microarray." BMC Urol. 2013;13:37.
Jemal et al., 2007, "Cancer statistics, 2007." CA Cancer J Clin, 57: 43-66.
Jess et al., "Risk of intestinal cancer in inflammatory bowel disease: a population-based study from olmsted county, Minnesota." Gastroenterology (2006) 130, pp. 1039-1046.
Jiao et al. "Somatic mutations in the Notch, NF-KB, PIK3CA, and Hedgehog pathways in human breast cancers." Genes, chromosomes & cancer. 2012; 51:480-9.
Kaiser. (2008). "Cancer genetics. A detailed genetic portrait of the deadliest human cancers." Science. 321: 1280-1281.
Kann L., et al., "Improved marker combination for detection of de novo genetic variation and aberrant DNA in colorectal neoplasia." Clin Chem 2006;52:2299-302.
Kariya et al., 1987, "Revision of consensus sequence of human Alu repeats—a review." Gene, 53: 1-10.
Kawai, et al. (1994). "Comparison of DNA methylation patterns among mouse cell lines by restriction landmark genomic screening." Mol. Cell Biol. 14 (11): 7421-7427.
Kim, H., et al., "Noninvasive molecular biomarkers for the detection of colorectal cancer," BMB Reports, 2008, vol. 41, No. 10, pp. 685-692.
Kisiel et al. "New DNA Methylation Markers for Pancreatic Cancer: Discovery, Tissue Validation, and Pilot Testing in Pancreatic Juice" Clinical Cancer Research, vol. 21, No. 19, May 28, 2015, pp. 4473-4481.
Kisiel et al. "Stool DNA testing for the detection of pancreatic cancer: assessment of methylation marker candidates." Cancer. 2012; 118:2623-31.
Kisiel et al. (AGA Abstracts, VS-68, vol. 138, No. 5, May 2010).
Kisiel, et al. (2011). "Stool DNA screening for colorectal cancer: opportunities to improve value with next generation tests." J Clin Gastroenterol. 45 (4): 301-8.

(56) References Cited

OTHER PUBLICATIONS

Kober et al. "Methyl-CpG binding column-based identification of nine genes hypermethylated in colorectal cancer." Molecular carcinogenesis. 2011; 50:846-56.

Kraus, et al., "Inflammation and colorectal cancer," Current Opinion in Pharmacology, vol. 9, No. 4, pp. 405-410 (2009).

Kronborg et al., 1996, "Randomised study of screening for colorectal cancer with faecal-occult-blood test." Lancet, 348: 1467-71.

Kronborg et al., 2004, "Randomized study of biennial screening with a faecal occult blood test: results after nine screening rounds." Scand J Gastroenterol, 39: 846-51.

Kuppuswamy et al. "Single nucleotide primer extension to detect genetic diseases: Experimental application to hemophilia B (factor IX) and cystic fibrosis genes" (1991) Proc. Natl. Acad. Sci. USA 88: 1143-1147.

Laird. (2010). "Principles and challenges of genome-wide DNA methylation analysis." Nat Rev Genet. 11: 191-203.

Lashner BA, "Evaluation of the Usefulness of Testing for p53 Mutations in Colorectal Cancer Surveillance for Ulcerative Colitis" Am J Gastroenterol (1999), 94, pp. 456-462.

Lee et al. "Pituitary homeobox 2 (PITX2) protects renal cancer cell lines against doxorubicin toxicity by transcriptional activation of the multidrug transporter ABCB1." International journal of cancer Journal international du cancer. 2013; 133:556-67.

Leung W.K., et al., "Detection of epigenetic changes in fecal DNA as a molecular screening test for colorectal cancer: A feasibility study." Clin Chem 2004; 50(11):2179-82.

Levin B, "Screening and Surveillance for Early Detection of Colorectal Cancer..." Gastroenterology (2008); 134, pp. 1570-1595.

Levin et al., 2008, "Screening and surveillance for the early detection of colorectal cancer and adenomatous polyps, 2008: a joint guideline from the American Cancer Society, the US Multi-Society Task Force on Colorectal Cancer, and the American College of Radiology." CA Cancer J Clin, 58: 130-60.

Li et al. "Association between Galphai2 and ELMO1/Dock180 connects chemokine signalling with Rac activation and metastasis." Nat Commun. 2013; 4:1706.

Lim, et al. (2010). "Cervical dysplasia: assessing methylation status (Methylight) of CCNA1, DAPK1, HS3ST2, PAX1 and TFPI2 (to improve diagnostic accuracy." Gynecol Oncol. 119: 225-231.

Lin, et al., Identification of disease-associated DNA methylation in intestinal tissues from patients with inflammatory bowel disease, Clinical Genetics, vol. 80, No. 1, pp. 59-67 (2011).

Liu et al. "Medulloblastoma expresses CD1d and can be targeted for immunotherapy with NKT cells." Clin Immunol. 2013;149:55-64.

Lokk et al. "Methylation Markers of Early-Stage Non-Small Cell Lung Cancer" PLOS ONE, vol. 7, No. 6, e398013, Jun. 2012.

Ma, et al. (2011). "MicroRNA-616 induces androgen-independent growth of prostate cancer cells by suppressing expression of tissue factor pathway inhibitor TFPI-2." Cancer Res. 71: 583-592.

Maeda, et al., "DNA hypermethylation in colorectal neoplasms and inflammatory bowel disease: a mini review," Inflammapharmacology, vol. 14, No. 5-6, pp. 204-206 (2006).

Mandel et al., 1993, "Reducing mortality from colorectal cancer by screening for fecal occult blood. Minnesota Colon Cancer Control Study." N Engl J Med, 328: 1365-71.

Matsubayashi, et al. (2006). "DNA methylation alterations in the pancreatic juice of patients with suspected pancreatic disease." Cancer Res. 66: 1208-1217.

Meissner et al. (2008). "Genome-scale DNA methylation maps of pluripotent and differentiated cells." Nature. 454: 766-70.

Meissner, 2006, "Patterns of colorectal cancer screening uptake among men and women in the United States." Cancer Epidemiol Biomarkers Prev, 15: 389-94.

Melle, et al. (2005), "Discovery and identification of a-defensins as low abundant, tumor-derived serum markers in colorectal cancer," 129(1): 66-73 abstract only.

Melotte et al., "N-Myc Downstream-Regulated Gene 4 (NDRG4): A Candidate Tumor Suppressor Gene and Potential Biomarker for Colorectal Cancer" (JNCL, vol. 101, No. 13, pp. 916-927, Jul. 2009).

Meuwis, "Contribution of proteomics to colorectal cancer diagnosis," Acta Endoscopica, vol. 37, p. 295-303, including translation, 2007.

Muller et al., 2004, "Methylation changes in faecal DNA: a marker for colorectal cancer screening?" Lancet, 363: 1283-5.

Naumov "Genome-scale analysis of DNA methylation in colorectal cancer using Infinium HumanMethylation450 BeadChips" Epigenetics, 2013, vol. 8, issue 9, pp. 921-934.

Nosho, et al. (2008): "PIK3CA mutation in colorectal cancer: Relationship with genetic and epigenetic alterations," Neoplasia. 10(6) 034-541, abstract only.

Obusez et al. "Adenocarcinoma in the ileal pouch: early detection and potential role of fecal DNA methylated markers in surveillance" (Int. J. Colorectal Dis. vol. 26, pp. 951-953, 2011).

Obusez et al. "Fecal methylated markers for the detection of adenocarcinoma in ileal pouches of patients with underlying ulcerative colitis" (Inflammatory Bowel Diseases: vol. 14, Issue pS42, Dec. 2008, P-0106).

Odze RD, "Genetic Alterations in Chronic Ulcerative Colitis-Associated Adenoma-Like DALMs Are Similar to Non-Colitic Sporadic Adenomas" Am J Surg Pathol (2000), 24, pp. 1209-1216.

Olaru, et al., "Unique patterns of CpG island methylation in inflammatory bowel disease-associated colorectal cancers," Inflammatory Bowel Diseases, vol. 18, No. 4, pp. 641-648 (Epub Aug. 9, 2011).

Olson et al., 2005, "DNA stabilization is critical for maximizing performance of fecal DNA-based colorectal cancer tests." Diagn Mol Pathol, 14: 183-91.

Omura, et al. (2008). "Genome-wide profiling of methylated promoters in pancreatic adenocarcinoma." Cancer Biol Ther. 7 (7): 1146-1156.

Omura, et al. (2009). "Epigenetics and epigenetic alterations in pancreatic cancer." Int. J. Clin Exp Pathol. 2: 310-326.

Osborn NK, and Ahlquist DA, "Stool screening for colorectal cancer: molecular approaches." Gastroenterology 2005;128:192-206.

Osborn, et al., "Aberrant methylation of the eyes absent 4 gene in ulcerative colitis-associated dysplasia," Clinical Gastroenterology and Hepatology, vol. 4, No. 2, pp. 212-218 (2006).

Oster, B. et al., "Identification and validation of highly frequent CpG island hypermethylation in colorectal adenomas and carcinomas." Int J Cancer. 2011;129(12):2855-66.

Pao et al. "The endothelin receptor B (EDNRB) promoter displays heterogeneous, site specific methylation patterns in normal and tumor cells" Human Molecular Genetics, vol. 10, No. 9, pp. 903-910.

Park, et al. (2002), "Expressiono f melanoma antigen-encoding genes (MAGE) by common primers for MAGE-A1 to -A6 in colorectal carcinomas among Koreans," J. Korean Med. Sci 17: 497-501.

Person et al. "Chronic cadmium exposure in vitro induces cancer cell characteristics in human lung cells." Toxicol Appl Pharmacol. 2013; 273(2):281-8.

Petko Z., et al., "Aberrantly Methylated CDKN2A, MGMT, and MLH1 in Colon Polyps and in Fecal DNA from Patients with Colorectal Polyps." Clin Cancer Res 2005;11:1203-9.

Raimondo et al. "487 Methylated DNA Markers in Pancreatic Juice Discriminate Pancreatic Cancer From Chronic Pancreatitis and Normal Controls" Gastroenterology 2013; 144:S-90.

Rex et al. "American College of Gastroenterology guidelines for colorectal cancer screening 2008." Am J Gastroenterol (2009); 104, pp. 739-750.

Ruppenthal et al. "TWIST1 Promoter Methylation in Primary Colorectal Carcinoma" Pathol. Oncol. Res., 2011, 17:867-872.

Sadri and Hornsby "Rapid Analysis of DNA Methylation Using New Restriction Enzyme Sites Created by Bisulfite Modification." (1996) Nucl. Acids Res. 24: 5058-5059.

(56) References Cited

OTHER PUBLICATIONS

Saitoh et al. (1995), "Intestinal protein loss and bleeding assessed by fecal hemoglobin, transferrin, albumin, and alpha-1-antitrypsin levels in patients with colorectal diseases," Digestion. 56(1): 67-75, abstract only.
Sambrook et al., 1989, Fritsch, E.F., Maniatis, T. (ed.), Molecular Cloning, Cold Spring Harbor Lab. Press, Cold Spring Harbor, N.Y., 30 pages.
Samowitz et al., 1999, "BAT-26 and BAT-40 instability in colorectal adenomas and carcinomas and germline polymorphisms." Am J Path, 154: 1637-41.
Sato et al., "Aberrant methylation of the HPP1 gene in ulcerative colitis-associated colorectal carcinoma." Cancer Res (2002), 62, pp. 6820-6822.
Sato, et al. (2003). "Discovery of novel targets of aberrant methylation in pancreatic carcinoma using high-throughput microarrays." Cancer Res. 63: 3735-3742.
Sato, et al. (2008). "CpG island methylation profile of pancreatic intraepithelial neoplasia." Mod Pathol. 21 93): 238-244.
Schulmann, et al., Molecular phenotype of inflammatory bowel disease-associated neoplasms with microsatellite instability, Gastroenterology, vol. 129, No. 1, pp. 74-85 (2005).
Schwartz et al., 1983, "The "HemoQuant" test: a specific and quantitative determination of heme (hemoglobin) in feces and other materials." Clin Chem, 29: 2061-7.
Schwartz et al., 1985, "Quantitative fecal recovery of ingested hemoglobin-heme in blood: comparisons by HemoQuant assay with ingested meat and fish." Gastroenterology, 89: 19-26.
Sen-Yo et al. "TWIST1 hypermethylation is observed in pancreatic cancer" Biomedical Reports; 1:33-33, 2013.
Seshagiri et al. "Recurrent R-spondin fusions in colon cancer." Nature. 2012; 488:660-4.
Shin et al. "Bile-based detection of extrahepatic cholangiocarcinoma with quantitative DNA methylation markers and its high sensitivity." The Journal of molecular diagnostics : JMD. 2012;14:256-63.
Singer-Sam et al. "A quantitative HpaII-PCR assay to measure methylation of DNA from a small number of cells" (1990) Nucl. Acids Res. 18(3): 687.
Singer-Sam et al. "A sensitive, quantitative assay for measurement of allele-specific transcripts differing by a single nucleotide." (1992) PCR Methods Appl. 1: 160-163.
Singh et al., 2006, "Risk of developing colorectal cancer following a negative colonoscopy examination: evidence for a 10-year interval between colonoscopies." JAMA, 295: 2366-73.
Stumm et al. "Strong expression of the neuronal transcription factor FOXP2 is linked to an increased risk of early PSA recurrence in ERG fusion-negative cancers." Journal of clinical pathology. 2013;66:563-8.
Summons to attend oral proceedings, European patent application No. 11760295.3, mailed Mar. 4, 2016.
Surdez et al. "Targeting the EWSR1-FLI1 oncogene-induced protein kinase PKC-beta abolishes ewing sarcoma growth." Cancer research. 2012;72:4494-503.
Szabo and Mann "Allele-specific expression and total expression levels of imprinted genes during early mouse development: implications for imprinting mechanisms." (1995) Genes Dev. 9(24): 3097-3108.
Tang, et al. (2010). "Prognostic significance of tissue factor pathway inhibitor 2 in pancreatic carcinoma and its effect on tumor invasion and metastatis." Med Oncol. 27: 867-875.
Taylor et al. "Expression of p53 in colorectal cancer and dysplasia complicating ulcerative colitis." Br J Surg (1993), 80, pp. 442-444.
Tibble, et al. (2001). "Faecal capprotectin and faecal occult blood tests in the diagnosis of colorectal carcinoma and adenoma.," Gut. 49:402-408.
Tonack, et al. (2009). "Pancreatic cancer: proteomic approaches to a challenging disease." Pancreatology. 9: 567-576.
Toyota, et al. (1999). "Identification of differentially methylated sequences in colorectal cancer by methylated CpG island amplification." Cancer Res. 59: 2307-2312.

Tsunoda, et al. (2009). "Methylation of CLDN6, FBN2, RBP1, RBP4, TFPI2 and TMEFF2 in esophageal squamous cell carcinoma." Oncol Rep. 21: 1067-1073.
Uchida, et al. (1994), "Immunochemical detection of human lactoferrin in feces as a new marker for inflammatory gastrointestinal disorders and colon cancer," Clinical Biochemistry. 27(4)L 259-264, abstract only.
Vincent et al. "Genome-wide analysis of promoter methylation associated with gene expression profile in pancreatic adenocarcinoma." Clinical cancer research : an official journal of the American Association for Cancer Research. 2011; 17:4341-54.
Wang, "Gene expression profiles and molecular markers to predict recurrence of duke's B Colon Cancer," vol. 22, p. 1564-1571, 2004.
Watanabe, T., "RUNX3 copy number predicts the development of UC-associated colorectal cancer" International Journal of Oncology (2011), 38, pp. 201-207.
Wen, et al. (2006), "Frequence epigenetic silencing of the bome morphogenic protein 2 gene through methylation in gastic carcinomas," Onogene. 25:2666-2673.
Wheeler et al. "Hypermethylation of the promoter region of the E-cadherin gene (CDH1) in sporadic and ulcerative colitis associated colorectal cancer." Gut (2001), 48, pp. 367-371.
Winawer et al., 1993, "Screening for colorectal cancer with fecal occult blood testing and sigmoidoscopy." J Natl Cancer Inst, 85: 1311-8.
Wittekind et al. (1986), "Localization of CEA, HCG, lysozyme, alpha-1-antitrypsin, and alpha-1-antichymotrypsin in gastric cancer and prognosis," Virchows Arch 409:715-724.
Wu, "Aberrant Gene Methylation in the Neoplastic Progression of Barrett's Esophagus: Identification of Candidate Diagnostic Markers" Gastroenterology (2011) 14: S-222.
Xiong, et al. (1997). Nucleic Acids Res. 25 (12): 2532-2534.
Yachida, et al. (2010). "Distant metastasis occurs late during the genetic evolution of pancreatic cancer." Nature. 467: 1114-1117.
Yamaguchi, et al. (2005). "Pancreatic juice cytology in intraductal papillary mucinous neoplasm of the pancreas." Pancreatology. 5: 416-421.
Yang N. et al. "Methylation markers for CCNA1 and C13ORF18 are strongly associated with high-grade cervical intraepithelial neoplasia and cervical cancer in cervical scrapings." Cancer epidemiology, biomarkers & prevention : a publication of the American Association for Cancer Research, cosponsored by the American Society of Preventive Oncology. 2009;18:3000-7.
Young, "Fecal Immunochemical Tests (FIT) vs. Office-based guaiac fecal occult blood test (FOBT)," Practical Gastroenterology, Colorectal Cancer, series 3, p. 46-56, 2004.
Zhang et al. (2009). "DNA methylation analysis of chromosome 21 gene promoters at single base pair and single allele resolution." PLoS Genet. 5 (3): e1000438.
Zhao et al. "Genome-wide identification of Epstein-Barr virus-driven promoter methylation profiles of human genes in gastric cancer cells." Cancer. 2013;119:304-12.
Zijlstra et al., 2002, "A quantitative analysis of rate-limiting steps in the metastatic cascade using human-specific real-time polymerase chain reaction." Cancer Res, 62: 7083-92.
Zou H., et al., "A Sensitive Method to Quantify Human Long DNA in Stool: Relevance to Colorectal Cancer Screening." Cancer Epidemiol Biomarkers Prev 2006;15:1115-9.
Zou H.Z., et al., "Detection of aberrant p16 methylation in the serum of colorectal cancer patients." Clin Cancer Res 2002;8(1):188-91.
Zou, et al. (2007), "Highly methylated genes in colorectal neoplasia: Implications for screening," Cancer Epidemilogy Biomarkers Prev. 16(12): 2686-2696.
Zou, et al. (2009). "T2036 Pan-Detection of Gastrointestinal Neoplasms by Stool DNA Testing Establishment of Feasibility." Gastroenterology. 136: A-625.
Zou, et al., "High Detection Rates of Colorectal Neoplasia by Stool DNA Testing with a Novel Digital Melt Curve Assay," Gastroenterology, vol. 136, No. 2, Feb. 1, 2009, pp. 459-470.
Zou, et al., "T2034 Stool DNA and Occult Blood for Detection of Colorectal Cancer: Complementary Markers," Gastroenterology, vol. 136, No. 5, May 1, 2009, p. A-625.

(56) References Cited

OTHER PUBLICATIONS

Tan et al. "Variable promoter region CpG island methylation of the putative tumor suppressor gene Connexin 26 in breast cancer" Carcinogenesis. 2002 23(2): 231-236.

Jin et al. "A multicenter, Double-blinded Validation study of methylation biomarkers for progression prediction in Barrett's Esophagus" Cancer Research, May 15, 2009, vol. 69, pp. 4112-4115.

Kaz et al. "DNA methylation profiling in Barrett's esophagus and esophageal adenocarcinoma reveals unique methylation signatures and molecular subclasses" Epigenetics, Dec. 1, 2011, vol. 6, pp. 1403-1412.

Zhai et al. "Genome-wide DNA Methylation Profiling of Cell-Free Serum DNA in Esophageal Adenocarcinoma and Barrett Esophagus" Neoplasia, Jan. 11, 2012, vol. 14, No. 1, pp. 29-33.

International Search Report, International Application No. PCT/US2016/023782, dated Sep. 1, 2016.

Haag S, et al., "Regression of Barrett's esophagus: the role of acid suppression, surgery, and ablative methods." Gastrointest Endosc. Aug 1999;50(2):229-40.

Kisiel, et al. "Su1340 Detection of Colorectal Cancer and Polyps in Patients with Inflammatory Bowel Disease by Novel Methylated Stool DNA Markers" Gastroenerology, vol. 146, No. 5, May 1, 2014, pp. S-440.

Taylor et al. "109 Discovery of Novel DNA Methylation Markers for the Detection of Colorectal Neopalsia: Selection by Methylome-Wide Analysis" Gastroenterology, vol. 146, No. 5, May 1, 2014, pp. S-30.

Kim et al. Methylation profiles of multiple CpG island loci in extrahepatic cholangiocarcinoma versus those of intrahepatic cholangiocarcinomas. Arch Pathol Lab Med 131:923-930, 2007.

Qiu et al. Hypermethylation of ACP1, BMP4, and TSPYL5 in Hepatocellular Carcinoma and Their Potential Clinical Significance, Digestive Diseases and Sciences, Sep. 19, 2015, vol. 61, No. 1, pp. 149-157.

International Search Report and Written Opinion, International Patent Application No. PCT/US2017/049915, dated Jan. 18, 2018.

Gao et al. "Global Analysis of DNA Methylation in hepatocellular cariconma by a liquid hybridization cpature-based bisulfite sequencing approach" Clinical Epigenetics, vol. 7, No. 86, Aug. 2015.

Barat et al. "Comparative Correlation Structure of Colon Cancer Locus Specific Methylation: Characterisation of Patient Profiles and Potential Markers across 3 Array-Based Datasets" J. of Cancer, vol. 6, pp. 795-811, Jul. 2015.

Sloane et al. "Epigenetic inactivation of the candidate tumor suppressor USP44 is a frequent and early event in colorectal neoplasia" Epigenetics, vol. 9, No. 8, pp. 1092-1100, Aug. 2014.

Kisiel AGA Abstracts #469, S-84, May 2013.

Loh et al. Genes Chromosomes and Cancer 47:449-460 2008.

Costello. 1994 vol. 269, No. 25, pp. 17228-17237.

Hesselink et al. ClinCancer Res 2011; 17:2459-2465.

Jiang et al. Gastroenterology Apr. 2008 vol. 134, No. 4., suppl 1, pp. A484.

Melotte et al. Cellular Oncology 2008 vol. 30, No. 2, p. 181.

Lenhard et al. Clinical Gastroenterology and Hepatology 2005; 3:142-149.

Fearnhead et al., "The ABC of APC," Hum. Mol. Genet. 2001, vol. 10, No. 7, pp. 721-733.

Fearon E., et al., "A Genetic Model for Colorectal Tumorigenesis", Cell, 1990, vol. 61, pp. 759-767.

Kinzler K., et al., "Lessons from Hereditary Colorectal Cancer" Cell, 1996, vol. 87, pp. 159-170.

Powell S., et al., "APC Mutations Occur Early During Colorectal Tumorigenesis", Letters to Nature, 1992, vol. 359, pp. 235-237.

International Search Report and Written Opinion, International Patent Application No. PCT/US2017/027439, dated Sep. 13, 2017, 26 pages.

Kisiel et al. "Stool DNA Testing for the Detection of Pancreatic Cancer: Identification and Assessment of Methylation Market Candidates" Gastroenterology, Apr. 21, 2011, vol. 140, iss. 5, suppl. 1, p. S-185.

Raimondo et al. "781 Sensitive DNA Marker Panel for Detection of Pancreatic Cancer by Assay in Pancreatic Juice" Gastroenterology, May 2, 2014, vol. 146, iss. 5, suppl. 1, p. S-132.

EP Search Report, EP Patent Application No. 17783141.9, dated Mar. 19, 2020, 13 pages.

Majumder, S. et al. Detection of Pancreatic High-Grade Dysplasia and Cancer using Novel Methylated DNA Markers: Discovery and Tissue Validation, AGA Abstracts vol. 150, Issue 4, Supplement 1, S120-S121, Apr. 1, 2016.

JP Notification of Reasons for Refusal, JP Patent Application No. 2018-554339, dated Apr. 20, 2021, 10 pages.

Majumder, S. et al. Molecular detection of pancreatic neoplasia: Current status and future promise, World J. Gastroenterol Oct. 28, 2015; 21(40): 11387-11395.

Wood, L et al. Pathology and Molecular Genetics of Pancreatic Neoplasms, Cancer J. 2012; 18(6): 492-501.

KR Office Action, KR Patent Application No. 10-2018-7032924, dated Jun. 18, 2021, 16 pages.

\* cited by examiner

DETECTING PANCREATIC HIGH-GRADE DYSPLASIA

FIELD OF INVENTION

Provided herein is technology for pancreatic high-grade dysplasia screening and particularly, but not exclusively, to methods, compositions, and related uses for detecting the presence of pancreatic high-grade dysplasia (intraductal papillary mucinous neoplasm high grade dysplasia (IPMN-HGD), pancreatic intraepithelial neoplasia 3 (PanIN-3), or pancreatic ductal adenocarcinoma (PDAC)).

BACKGROUND

Despite medical advances, pancreatic cancer is one of the most deadly diseases. In 2011, there were estimated 44,030 people diagnosed with pancreatic cancer in the U.S. of which approximately 37,660 people died. Pancreatic cancer is the fourth most common cancer-related cause of death among U.S. men (after lung, prostate and colorectal cancer) and women (after lung, breast and colorectal cancer). The peak incidence occurs in the 7th and 8th decades of life with the incidence nearly the same in both men and women. While death rates of lung, colorectal, breast, and prostate cancer have declined in the U.S. since 2003, pancreatic cancer has increased during that same time. The estimated new cases of pancreatic cancer globally in 2011 in developed countries is 84,200 (men) and 80,900 (women), while the estimated deaths are 82,700 (men) and 79,100 (women). Unfortunately, most of the symptomatic patients are incurable. The prognosis for pancreatic cancer patients is very poor with a 5-year relative survival rate of 6% for all stages combined. This is due to the late stage of the disease at the time of diagnosis.

There is a great need for early detection of pancreatic cancer to improve the survival rate of these patients.

SUMMARY

Pancreatic cancer, currently the 4$^{th}$ most common cause of cancer death in USA (see, Siegel, R., et al., CA Cancer J Clin, 2014. 64(1): p. 9-29), is the most lethal of all cancers with an overall 5-year survival under 5% (see, Wolfgang, C. L., et al., CA: a cancer journal for clinicians, 2013. 63(5): p. 318-48). Each year, the number of pancreatic cancers diagnosed nearly equals the number of deaths for the disease. This dismal outcome has not changed over the past 3 decades, despite efforts to improve therapy (see, Wolfgang, C. L., et al., CA: a cancer journal for clinicians, 2013. 63(5): p. 318-48). Of grave concern, pancreatic cancer is on the rise. In the US, pancreatic cancer is anticipated to become the 2$^{nd}$ most common cause for cancer death by 2030 (see, Rahib, L., et al., Cancer research, 2014. 74(14): p. 4006). In other parts of the world, pancreatic cancer is one of the only cancers with a worsening forecast, whereas the incidence and mortality of other common cancers (e.g., breast, colon, and prostate) are trending downward (see, Malvezzi, M., et al., Annals of oncology: official journal of the European Society for Medical Oncology/ESMO, 2014).

Pancreatic cancer is usually diagnosed after symptoms and at late stage, as there are no effective or widely-used screening tools. Currently, 85% of cases present with metastatic disease and typically survive <6 months after diagnosis (see, Wolfgang, C. L., et al., CA: a cancer journal for clinicians, 2013. 63(5): p. 318-48). For the few who present symptomatically without apparent locally advanced disease or distant metastasis and go on to resection, overall survival is less than 20% at 5 years (see, Wolfgang, C. L., et al., CA: a cancer journal for clinicians, 2013. 63(5): p. 318-48). Encouragingly, the small subset of cases found with earliest stage tumors have the best outcomes, with 5 year survival rates of 30-60% with lesions<2 cm and over 75% with those <1 cm (see, Sohn, T., et al., Journal of gastrointestinal surgery: official journal of the Society for Surgery of the Alimentary Tract, 2000. 4(6): p. 567-579; Furukawa, H., et al., Cancer, 1996. 78(5): p. 986-990; Shimizu, Y., et al., Journal of gastroenterology and hepatology, 2005. 20(10): p. 1591-1594; Ishikawa, O., et al., Hepato-Gastroenterology, 1999. 46(25): p. 8-15; Tsuchiya, R., et al., Annals of Surgery, 1986. 203(1): p. 77-81). Furthermore, incidentally discovered early stage pancreatic cancers in persons without symptoms appear to have high survival rates with curative resection, based on small anecdotal series (see, Yeo, C. J. and J. L. Cameron, Langenbeck's archives of surgery/Deutsche Gesellschaft für Chirurgie, 1998. 383(2): p. 129-33; Okano, K. and Y. Suzuki, World journal of gastroenterology: WJG, 2014. 20(32): p. 11230-11240). Thus, there is solid evidence that pre-symptomatic detection of earliest stage pancreatic cancer can lead to high cure rates, which strikingly underscores the need for an effective screening tool.

Sporadic forms of pancreatic cancer account for >90% of all cases, and <10% of cases have an underlying genetic or acquired predisposing condition. Such high risk acquired conditions include certain rare genetic disorders, chronic pancreatitis, incidentally discovered cystic pancreatic precancers (particularly intraductal papillary mucinous neoplasms (IPMNs)), obesity, and recent-onset diabetes mellitus (see, Chakraborty, S., et al., Biochimica et biophysica acta, 2011. 1815(1): p. 44-64). Screening and surveillance programs using various endoscopic and imaging methods are inconsistently applied to patients with these known hereditary or acquired risk factors. Because the large majority of pancreatic cancers occur in persons without obvious risk factors, selective screening in the high-risk subset will have little influence on cancer incidence or mortality overall. To have maximal impact on pancreatic cancer mortality, an effective population-wide screening tool is required.

To lessen the heavy toll of this dread disease, effective screening approaches are urgently needed. There is an imperative for innovation that will deliver accurate, affordable, and safe screening tools for the pre-symptomatic detection of earliest stage cancer and advanced precancer.

The present invention addresses this need. Indeed, the present invention provides novel methylated DNA markers that discriminate cases with high-grade precursor lesions and cancer from controls with normal pancreas or low-grade precursors.

Methylated DNA has been studied as a potential class of biomarkers in the tissues of most tumor types. In many instances, DNA methyltransferases add a methyl group to DNA at cytosine-phosphate-guanine (CpG) island sites as an epigenetic control of gene expression. In a biologically attractive mechanism, acquired methylation events in promoter regions of tumor suppressor genes are thought to silence expression, thus contributing to oncogenesis. DNA methylation may be a more chemically and biologically stable diagnostic tool than RNA or protein expression (Laird (2010) Nat Rev Genet 11: 191-203). Furthermore, in other cancers like sporadic colon cancer, methylation markers offer excellent specificity and are more broadly informative and sensitive than are individual DNA mutations (Zou et al (2007) Cancer Epidemiol Biomarkers Prev 16: 2686-96).

Analysis of CpG islands has yielded important findings when applied to animal models and human cell lines. For example, Zhang and colleagues found that amplicons from different parts of the same CpG island may have different levels of methylation (Zhang et al. (2009) PLoS Genet 5: e1000438). Further, methylation levels were distributed bi-modally between highly methylated and unmethylated sequences, further supporting the binary switch-like pattern of DNA methyltransferase activity (Zhang et al. (2009) PLoS Genet 5: e1000438). Analysis of murine tissues in vivo and cell lines in vitro demonstrated that only about 0.3% of high CpG density promoters (HCP, defined as having >7% CpG sequence within a 300 base pair region) were methylated, whereas areas of low CpG density (LCP, defined as having <5% CpG sequence within a 300 base pair region) tended to be frequently methylated in a dynamic tissue-specific pattern (Meissner et al. (2008) Nature 454: 766-70). HCPs include promoters for ubiquitous housekeeping genes and highly regulated developmental genes. Among the HCP sites methylated at >50% were several established markers such as Wnt 2, NDRG2, SFRP2, and BMP3 (Meissner et al. (2008) Nature 454: 766-70).

Experiments conducted during the course of developing embodiments for the present invention compared the methylation state of DNA markers from pancreatic tissue of subjects having intraductal papillary mucinous neoplasm high grade dysplasia (IPMN-HGD), pancreatic intraepithelial neoplasia 3 (PanIN-3), or pancreatic ductal adenocarcinoma (PDAC) to the methylation state of the same DNA markers from control subjects (e.g., subjects having IPMN-low grade dysplasia (IPMN-LGD), PanIN-1, and PanIN-2 for the respective tissue type). Such experiments identified and validated methylated DNA marker candidates that discriminate a case group with high-grade precursors (IPMN-HGD, PanIN-3) or invasive cancer (PDAC) from a control group with either normal pancreas or low-grade precursor lesions (IPMN-low grade dysplasia (IPMN-LGD), PanIN-1, and PanIN-2) (see, Examples I, II, IV, and V).

Accordingly, provided herein is technology for pancreatic high-grade dysplasia (IPMN-HGD, PanIN-3, or PDAC) screening (e.g., surveilling) and particularly, but not exclusively, to methods, compositions, and related uses for detecting the presence of pancreatic high-grade dysplasia (IPMN-HGD, PanIN-3, or PDAC).

Markers and/or panels of markers were identified (e.g., a chromosomal region having an annotation provided in Table 2) capable of detecting pancreatic high-grade dysplasia in subjects (IPMN-HGD, PanIN-3, or PDAC) (see, Examples I, II, IV, and V) (BMP3, NDRG4, ABCB1, AK055957, C13ORF18, CD1D, CLEC11A, DLX4, ELMO1, EMX1, FER1L4, FRMD4A, GRIN2D, HOXA1, LRRC4, PRKCB, SP9, ST6GAL2, ST8SIA1, TBX15, VWC2, and ZNF781).

As described herein, the technology provides a number of methylated DNA markers and subsets thereof (e.g., sets of 2, 3, 4, 5, 6, 7, 10, 15, 19, 20, 21, 50, 75, 94 markers) with high discrimination for detecting the presence of pancreatic high-grade dysplasia (IPMN-HGD, PanIN-3, or PDAC) in subjects. Experiments applied a selection filter to candidate markers to identify markers that provide a high signal to noise ratio and a low background level to provide high specificity, e.g., when assaying media (e.g., colorectal tissue, stool sample) for purposes of screening or diagnosis (e.g., cancer screening or diagnosis).

In some embodiments, the technology is related to assessing the presence of and methylation state of one or more of the markers identified herein in a biological sample. These markers comprise one or more differentially methylated regions (DMR) as discussed herein, e.g., as provided in Table 2. Methylation state is assessed in embodiments of the technology. As such, the technology provided herein is not restricted in the method by which a gene's methylation state is measured. For example, in some embodiments the methylation state is measured by a genome scanning method. For example, one method involves restriction landmark genomic scanning (Kawai et al. (1994) Mol. Cell. Biol. 14: 7421-7427) and another example involves methylation-sensitive arbitrarily primed PCR (Gonzalgo et al. (1997) Cancer Res. 57: 594-599). In some embodiments, changes in methylation patterns at specific CpG sites are monitored by digestion of genomic DNA with methylation-sensitive restriction enzymes followed by Southern analysis of the regions of interest (digestion-Southern method). In some embodiments, analyzing changes in methylation patterns involves a PCR-based process that involves digestion of genomic DNA with methylation-sensitive restriction enzymes prior to PCR amplification (Singer-Sam et al. (1990) Nucl. Acids Res. 18: 687). In addition, other techniques have been reported that utilize bisulfite treatment of DNA as a starting point for methylation analysis. These include methylation-specific PCR (MSP) (Herman et al. (1992) Proc. Natl. Acad. Sci. USA 93: 9821-9826) and restriction enzyme digestion of PCR products amplified from bisulfite-converted DNA (Sadri and Hornsby (1996) Nucl. Acids Res. 24: 5058-5059; and Xiong and Laird (1997) Nucl. Acids Res. 25: 2532-2534). PCR techniques have been developed for detection of gene mutations (Kuppuswamy et al. (1991) Proc. Natl. Acad. Sci. USA 88: 1143-1147) and quantification of allelic-specific expression (Szabo and Mann (1995) Genes Dev. 9: 3097-3108; and Singer-Sam et al. (1992) PCR Methods Appl. 1: 160-163). Such techniques use internal primers, which anneal to a PCR-generated template and terminate immediately 5' of the single nucleotide to be assayed. Methods using a "quantitative Ms-SNuPE assay" as described in U.S. Pat. No. 7,037,650 are used in some embodiments.

Upon evaluating a methylation state, the methylation state is often expressed as the fraction or percentage of individual strands of DNA that is methylated at a particular site (e.g., at a single nucleotide, at a particular region or locus, at a longer sequence of interest, e.g., up to a ~100-bp, 200-bp, 500-bp, 1000-bp subsequence of a DNA or longer) relative to the total population of DNA in the sample comprising that particular site. Traditionally, the amount of the unmethylated nucleic acid is determined by PCR using calibrators. Then, a known amount of DNA is bisulfite treated and the resulting methylation-specific sequence is determined using either a real-time PCR or other exponential amplification, e.g., a QUARTS assay (e.g., as provided by U.S. Pat. Nos. 8,361, 720; 8,916,344; and U.S. Pat. Appl. Pub. Nos. 2012/0122088 and 2012/0122106).

For example, in some embodiments methods comprise generating a standard curve for the unmethylated target by using external standards. The standard curve is constructed from at least two points and relates the real-time Ct value for unmethylated DNA to known quantitative standards. Then, a second standard curve for the methylated target is constructed from at least two points and external standards. This second standard curve relates the Ct for methylated DNA to known quantitative standards. Next, the test sample Ct values are determined for the methylated and unmethylated populations and the genomic equivalents of DNA are calculated from the standard curves produced by the first two steps. The percentage of methylation at the site of interest is calculated from the amount of methylated DNAs relative to the total amount of DNAs in the population, e.g., (number of methylated DNAs)/(the number of methylated DNAs+number of unmethylated DNAs)×100.

Also provided herein are compositions and kits for practicing the methods. For example, in some embodiments, reagents (e.g., primers, probes) specific for one or more markers are provided alone or in sets (e.g., sets of primers pairs for amplifying a plurality of markers). Additional reagents for conducting a detection assay may also be provided (e.g., enzymes, buffers, positive and negative controls for conducting QuARTS, PCR, sequencing, bisulfate, or other assays). In some embodiments, the kits containing one or more reagent necessary, sufficient, or useful for conducting a method are provided. Also provided are reactions mixtures containing the reagents. Further provided are master mix reagent sets containing a plurality of reagents that may be added to each other and/or to a test sample to complete a reaction mixture.

In some embodiments, the technology described herein is associated with a programmable machine designed to perform a sequence of arithmetic or logical operations as provided by the methods described herein. For example, some embodiments of the technology are associated with (e.g., implemented in) computer software and/or computer hardware. In one aspect, the technology relates to a computer comprising a form of memory, an element for performing arithmetic and logical operations, and a processing element (e.g., a microprocessor) for executing a series of instructions (e.g., a method as provided herein) to read, manipulate, and store data. In some embodiments, a microprocessor is part of a system for determining a methylation state (e.g., of one or more DMR, e.g., DMR 1-96 as provided in Tables 2 and 6); comparing methylation states (e.g., of one or more DMR, e.g., DMR 1-96 as provided in Tables 2 and 6); generating standard curves; determining a Ct value; calculating a fraction, frequency, or percentage of methylation (e.g., of one or more DMR, e.g., DMR 1-96 as provided in Tables 2 and 6); identifying a CpG island; determining a specificity and/or sensitivity of an assay or marker; calculating an ROC curve and an associated AUC; sequence analysis; all as described herein or is known in the art.

In some embodiments, a microprocessor or computer uses methylation state data in an algorithm to predict a site of a cancer.

In some embodiments, a software or hardware component receives the results of multiple assays and determines a single value result to report to a user that indicates a cancer risk based on the results of the multiple assays (e.g., determining the methylation state of multiple DMR, e.g., as provided in Tables 2 and 6). Related embodiments calculate a risk factor based on a mathematical combination (e.g., a weighted combination, a linear combination) of the results from multiple assays, e.g., determining the methylation states of multiple markers (such as multiple DMR, e.g., as provided in Tables 2 and 6). In some embodiments, the methylation state of a DMR defines a dimension and may have values in a multidimensional space and the coordinate defined by the methylation states of multiple DMR is a result, e.g., to report to a user.

Some embodiments comprise a storage medium and memory components. Memory components (e.g., volatile and/or nonvolatile memory) find use in storing instructions (e.g., an embodiment of a process as provided herein) and/or data (e.g., a work piece such as methylation measurements, sequences, and statistical descriptions associated therewith). Some embodiments relate to systems also comprising one or more of a CPU, a graphics card, and a user interface (e.g., comprising an output device such as display and an input device such as a keyboard).

Programmable machines associated with the technology comprise conventional extant technologies and technologies in development or yet to be developed (e.g., a quantum computer, a chemical computer, a DNA computer, an optical computer, a spintronics based computer, etc.).

In some embodiments, the technology comprises a wired (e.g., metallic cable, fiber optic) or wireless transmission medium for transmitting data. For example, some embodiments relate to data transmission over a network (e.g., a local area network (LAN), a wide area network (WAN), an ad-hoc network, the internet, etc.). In some embodiments, programmable machines are present on such a network as peers and in some embodiments the programmable machines have a client/server relationship.

In some embodiments, data are stored on a computer-readable storage medium such as a hard disk, flash memory, optical media, a floppy disk, etc.

In some embodiments, the technology provided herein is associated with a plurality of programmable devices that operate in concert to perform a method as described herein. For example, in some embodiments, a plurality of computers (e.g., connected by a network) may work in parallel to collect and process data, e.g., in an implementation of cluster computing or grid computing or some other distributed computer architecture that relies on complete computers (with onboard CPUs, storage, power supplies, network interfaces, etc.) connected to a network (private, public, or the internet) by a conventional network interface, such as Ethernet, fiber optic, or by a wireless network technology.

For example, some embodiments provide a computer that includes a computer-readable medium. The embodiment includes a random access memory (RAM) coupled to a processor. The processor executes computer-executable program instructions stored in memory. Such processors may include a microprocessor, an ASIC, a state machine, or other processor, and can be any of a number of computer processors, such as processors from Intel Corporation of Santa Clara, Calif. and Motorola Corporation of Schaumburg, Ill. Such processors include, or may be in communication with, media, for example computer-readable media, which stores instructions that, when executed by the processor, cause the processor to perform the steps described herein.

Embodiments of computer-readable media include, but are not limited to, an electronic, optical, magnetic, or other storage or transmission device capable of providing a processor with computer-readable instructions. Other examples of suitable media include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any suitable computer-programming language, including, for example, C, C++, C #, Visual Basic, Java, Python, Perl, and JavaScript.

Computers are connected in some embodiments to a network. Computers may also include a number of external or internal devices such as a mouse, a CD-ROM, DVD, a keyboard, a display, or other input or output devices. Examples of computers are personal computers, digital assistants, personal digital assistants, cellular phones, mobile phones, smart phones, pagers, digital tablets, laptop computers, internet appliances, and other processor-based devices. In general, the computers related to aspects of the technology provided herein may be any type of processor-based platform that operates on any operating system, such as Microsoft Windows, Linux, UNIX, Mac OS X, etc., capable of supporting one or more programs comprising the technology provided herein. Some embodiments comprise a personal computer executing other application programs (e.g., applications). The applications can be contained in memory and can include, for example, a word processing application, a spreadsheet application, an email application, an instant messenger application, a presentation application, an Internet browser application, a calendar/organizer application, and any other application capable of being executed by a client device.

All such components, computers, and systems described herein as associated with the technology may be logical or virtual.

Provided herein is technology related to a method of screening for pancreatic high-grade dysplasia (IPMN-HGD, PanIN-3, or PDAC) in a sample obtained from a subject, the method comprising assaying a methylation state of a marker in a sample obtained from a subject; and identifying the subject as having pancreatic high-grade dysplasia (IPMN-HGD, PanIN-3, or PDAC) when the methylation state of the marker is different than a methylation state of the marker assayed in a subject that does not have pancreatic high-grade dysplasia (IPMN-HGD, PanIN-3, or PDAC), wherein the marker comprises one or more bases in a differentially methylated region (DMR) selected from BMP3, NDRG4, ABCB1, AK055957, C13ORF18, CD1D, CLEC11A, DLX4, ELMO1, EMX1, FER1L4, FRMD4A, GRIN2D, HOXA1, LRRC4, PRKCB, SP9, ST6GAL2, ST8SIA1, TBX15, VWC2, and ZNF781 as provided in Tables 2 and 6.

The technology is not limited in the methylation state assessed. In some embodiments assessing the methylation state of the marker in the sample comprises determining the methylation state of one base. In some embodiments, assaying the methylation state of the marker in the sample comprises determining the extent of methylation at a plurality of bases. Moreover, in some embodiments the methylation state of the marker comprises an increased methylation of the marker relative to a normal methylation state of the marker. In some embodiments, the methylation state of the marker comprises a decreased methylation of the marker relative to a normal methylation state of the marker. In some embodiments the methylation state of the marker comprises a different pattern of methylation of the marker relative to a normal methylation state of the marker.

Furthermore, in some embodiments the marker is a region of 100 or fewer bases, the marker is a region of 500 or fewer bases, the marker is a region of 1000 or fewer bases, the marker is a region of 5000 or fewer bases, or, in some embodiments, the marker is one base. In some embodiments the marker is in a high CpG density promoter.

The technology is not limited by sample type. For example, in some embodiments the sample is a stool sample, a tissue sample (e.g., stomach tissue, pancreatic tissue, bile duct/liver tissue, pancreatic juice, pancreatic cyst fluid, and colorectal tissue), a blood sample (e.g., plasma, serum, whole blood), an excretion, or a urine sample.

Furthermore, the technology is not limited in the method used to determine methylation state. In some embodiments the assaying comprises using methylation specific polymerase chain reaction, nucleic acid sequencing, mass spectrometry, methylation specific nuclease, mass-based separation, or target capture. In some embodiments, the assaying comprises use of a methylation specific oligonucleotide. In some embodiments, the technology uses massively parallel sequencing (e.g., next-generation sequencing) to determine methylation state, e.g., sequencing-by-synthesis, real-time (e.g., single-molecule) sequencing, bead emulsion sequencing, nanopore sequencing, etc.

The technology provides reagents for detecting a DMR, e.g., in some embodiments are provided a set of oligonucleotides comprising the sequences provided by SEQ ID NO: 1-44 (Table 3) and SEQ ID NO: 45, 46, 47 and 48 (Table 7). In some embodiments are provided an oligonucleotide comprising a sequence complementary to a chromosomal region having a base in a DMR, e.g., an oligonucleotide sensitive to methylation state of a DMR.

The technology provides various panels of markers, e.g., in some embodiments the marker comprises a chromosomal region having an annotation that is provided in Tables 2 and 6 and that comprises the marker (see, Tables 2 and 6). In addition, embodiments provide a method of analyzing a DMR from Tables 2 and 6 with one or more of DMR Nos. 1-96.

Kit embodiments are provided, e.g., a kit comprising a bisulfite reagent; and a control nucleic acid comprising a sequence from a DMR selected from a group consisting of DMR 1-96 (from Tables 2 and 6) and having a methylation state associated with a subject who does not have pancreatic high-grade dysplasia (IPMN-HGD, PanIN-3, or PDAC). Kit embodiments are provided, e.g., a kit comprising a bisulfite reagent; and a control nucleic acid comprising a sequence from a DMR selected from a group consisting of DMR 1-96 or DMR 1, 21, 24, 25, 26, 55, 70, 77, 81, 84, 92, 95 and 96 (from Tables 2 and 6) and having a methylation state associated with a subject who does not have pancreatic high-grade dysplasia (IPMN-HGD, PanIN-3, or PDAC).

Some kit embodiments comprise a sample collector for obtaining a sample from a subject (e.g., a stool sample); reagents for isolating a nucleic acid from the sample; a bisulfite reagent; and an oligonucleotide as described herein.

The technology is related to embodiments of compositions (e.g., reaction mixtures). In some embodiments are provided a composition comprising a nucleic acid comprising a DMR and a bisulfite reagent. Some embodiments provide a composition comprising a nucleic acid comprising a DMR and an oligonucleotide as described herein. Some embodiments provide a composition comprising a nucleic acid comprising a DMR and a methylation-sensitive restriction enzyme. Some embodiments provide a composition comprising a nucleic acid comprising a DMR and a polymerase.

Additional related method embodiments are provided for screening for pancreatic high-grade dysplasia (IPMN-HGD, PanIN-3, or PDAC) in a sample obtained from a subject, e.g., a method comprising determining a methylation state of a marker in the sample comprising a base in a DMR that is one or more of DMR 1-96 or DMR 1, 21, 24, 25, 26, 55, 70, 77, 81, 84, 92, 95 and 96 (from Tables 2 and 6); comparing the methylation state of the marker from the subject sample to a methylation state of the marker from a normal control sample from a subject who does not have pancreatic high-grade dysplasia (IPMN-HGD, PanIN-3, or PDAC); and determining a confidence interval and/or a p value of the difference in the methylation state of the subject sample and the normal control sample.

In some embodiments, the confidence interval is 90%, 95%, 97.5%, 98%, 99%, 99.5%, 99.9% or 99.99% and the p value is 0.1, 0.05, 0.025, 0.02, 0.01, 0.005, 0.001, or 0.0001. Some embodiments of methods provide steps of reacting a nucleic acid comprising a DMR with a bisulfate reagent to produce a bisulfate-reacted nucleic acid; sequencing the bisulfate-reacted nucleic acid to provide a nucleotide sequence of the bisulfate-reacted nucleic acid; comparing the nucleotide sequence of the bisulfate-reacted nucleic acid with a nucleotide sequence of a nucleic acid comprising the DMR from a subject who does not have a cancer to identify differences in the two sequences; and identifying the subject as having a neoplasm when a difference is present.

Systems for screening for pancreatic high-grade dysplasia (IPMN-HGD, PanIN-3, or PDAC) in a sample obtained from a subject are provided by the technology. Exemplary embodiments of systems include, e.g., a system for screening for pancreatic high-grade dysplasia (IPMN-HGD, PanIN-3, or PDAC) in a sample obtained from a subject, the system comprising an analysis component configured to determine the methylation state of a sample, a software component configured to compare the methylation state of the sample with a control sample or a reference sample methylation state recorded in a database, and an alert component configured to alert a user of a pancreatic high-grade dysplasia-associated methylation state (e.g., a methylation state for no pancreatic high-grade dysplasia, a methylation state for pancreatic high-grade dysplasia). An alert is determined in some embodiments by a software component that receives the results from multiple assays (e.g., determining the methylation states of multiple markers, e.g., DMR, e.g., as provided in Tables 2 and 6) and calculating a value or result to report based on the multiple results. Some embodiments provide a database of weighted parameters associated with each DMR provided herein for use in calculating a value or result and/or an alert to report to a user (e.g., such as a physician, nurse, clinician, etc.). In some embodiments all results from multiple assays are reported and in some embodiments one or more results are used to provide a score, value, or result based on a composite of one or more results from multiple assays that is indicative of a pancreatic high-grade dysplasia risk in a subject.

In some embodiments of systems, a sample comprises a nucleic acid comprising a DMR. In some embodiments the system further comprises a component for isolating a nucleic acid, a component for collecting a sample such as a component for collecting a stool sample. In some embodiments, the system comprises nucleic acid sequences comprising a DMR. In some embodiments the database comprises nucleic acid sequences from subjects who do not have pancreatic high-grade dysplasia (IPMN-HGD, PanIN-3, or PDAC). Also provided are nucleic acids, e.g., a set of nucleic acids, each nucleic acid having a sequence comprising a DMR. In some embodiments the set of nucleic acids wherein each nucleic acid has a sequence from a subject who does not have pancreatic high-grade dysplasia (IPMN-HGD, PanIN-3, or PDAC). Related system embodiments comprise a set of nucleic acids as described and a database of nucleic acid sequences associated with the set of nucleic acids. Some embodiments further comprise a bisulfate reagent. And, some embodiments further comprise a nucleic acid sequencer.

In certain embodiments, methods for detecting pancreatic high-grade dysplasia in a sample obtained from a subject are provided, comprising a) obtaining a sample comprising DNA from a subject; b) treating the obtained DNA with a reagent which selectively modifies unmethylated cytosine residues in the obtained DNA to produce modified residues but which does not modify methylated cytosine residues; c) determining the methylation level of one or more DNA methylation markers in the DNA having undergone the treating of step b), wherein one or more DNA methylation markers comprises a base in a differentially methylated region (DMR) as provided by DMR 1-96 or DMR 1, 21, 24, 25, 26, 55, 70, 77, 81, 84, 92, 95 and 96 (from Tables 2 and 6), d) comparing the determined methylation level of the one or more DNA methylation markers with methylation level references for the one or more DNA methylation markers for subjects who do not have pancreatic high-grade dysplasia (IPMN-HGD, PanIN-3, or PDAC); and e) identifying the subject as having pancreatic high-grade dysplasia (IPMN-HGD, PanIN-3, or PDAC) when differences are present.

In some embodiments, a determination of elevated methylation in one or more of the DNA methylation markers comprises a determination of altered methylation within a region selected from the group consisting of a CpG island and a CpG island shore.

In some embodiments, a determination of elevated methylation within the CpG island or CpG shore comprises elevated methylation within a coding region or a regulatory region of the DNA methylation marker.

In some embodiments, the determining the methylation level of one or more DNA methylation markers in the DNA having undergone the treating of step b) comprises determining the methylation score and/or the methylation frequency of the one or more DNA methylation markers. In some embodiments, the treating of step b) is accomplished through bisulfite modification of the obtained DNA.

In some embodiments, the determining the methylation level of one or more DNA methylation markers in the DNA having undergone the treating of step b) is achieved by a technique selected from the group consisting of methylation-specific PCR, quantitative methylation-specific PCR, methylation-sensitive DNA restriction enzyme analysis, quantitative bisulfite pyrosequencing, and bisulfite genomic sequencing PCR.

In some embodiments, the sample comprises pancreatic tissue and/or pancreatic juice. colorectal tissue. In some embodiments, the sample comprises pancreatic cyst fluid. In some embodiments, the sample comprises a stool sample. In some embodiments, the sample comprises a blood sample.

In certain embodiments, the present invention provides methods for characterizing a biological sample through measuring a methylation level of a CpG site for two or more genes selected from either BMP3, NDRG4, ABCB1, AK055957, C13ORF18, CD1D, CLEC11A, DLX4, ELMO1, EMX1, FER1L4, FRMD4A, GRIN2D, HOXA1, LRRC4, PRKCB, SP9, ST6GAL2, ST8SIA1, TBX15, VWC2, and ZNF781 in a biological sample of a human.

Such methods are not limited to a particular method for measuring a methylation level of a CpG site. In some embodiments, such methods measure the methylation level of a CpG site through treating genomic DNA in the biological sample with bisulfite; amplifying the bisulfite-treated genomic DNA using a set of primers for the selected two or more genes; and determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR.

In some embodiments, measuring the methylation level a CpG site for two or more genes comprises a determination selected from the group consisting of determining the methylation score of said CpG site and determining the methylation frequency of said CpG site.

In some embodiments, such methods further comprise comparing the methylation level to a methylation level of a corresponding set of genes in control samples without pancreatic high-grade dysplasia (IPMN-HGD, PanIN-3, or PDAC); and determining that the individual has pancreatic high-grade dysplasia (IPMN-HGD, PanIN-3, or PDAC) when the methylation level measured in the two or more genes is higher than the methylation level measured in the respective control samples.

Such methods are not limited to a particular type of biological sample. In some embodiments, the biological sample comprises pancreatic tissue and/or pancreatic cyst fluid. In some embodiments, the biological sample comprises a stool sample, a blood sample, and/or a blood fraction sample.

In some embodiments, the CpG site is present in a coding region or a regulatory region.

In some embodiments, the following set of primers for the selected two or more genes:
for BMP3 a set of primers consisting of SEQ ID NOS: 45 and 46,
for NDRG4 a set of primers consisting of SEQ ID NOS: 47 and 48,
for ABCB1 a set of primers consisting of SEQ ID NOS: 1 and 2,
for AK055957 a set of primers consisting of SEQ ID NOS: 3 and 4,
for C13ORF18 a set of primers consisting of SEQ ID NOS: 7 and 8,
for CD1D a set of primers consisting of SEQ ID NOS: 43 and 44,
for CLEC11A a set of primers consisting of SEQ ID NOS: 9 and 10,
for DLX4 a set of primers consisting of SEQ ID NOS: 11 and 12,
for ELMO1 a set of primers consisting of SEQ ID NOS: 13 and 14,
for EMX1 a set of primers consisting of SEQ ID NOS: 15 and 16,
for FER1L4 a set of primers consisting of SEQ ID NOS: 17 and 18,
for FRMD4A a set of primers consisting of SEQ ID NOS: 19 and 20,
for GRIN2D a set of primers consisting of SEQ ID NOS: 21 and 22,
for HOXA1 a set of primers consisting of SEQ ID NOS: 23 and 24,
for LRRC4 a set of primers consisting of SEQ ID NOS: 25 and 26,
for PRKCB a set of primers consisting of SEQ ID NOS: 29 and 30,
for SP9 a set of primers consisting of SEQ ID NOS: 31 and 32,
for ST6GAL2 a set of primers consisting of SEQ ID NOS: 33 and 34,
for ST8SIA1 a set of primers consisting of SEQ ID NOS: 35 and 36,
for TBX15 a set of primers consisting of SEQ ID NOS: 37 and 38,
for VWC2 a set of primers consisting of SEQ ID NOS: 39 and 40, and
for ZNF781 a set of primers consisting of SEQ ID NOS: 41 and 42.

Additional embodiments will be apparent to persons skilled in the relevant art based on the teachings contained herein.

BRIEF DESCRIPTION OF THE DRAWINGS

FIG. 2 demonstrates distribution of the top three methylated DNA markers in pancreatic cyst fluid (normalized by beta-actin) across cases (HGD/cancer) and controls (LGD/ No dysplasia) (see, Example V).

FIG. 3 shows pancreatic cyst fluid levels of two top candidate methylated DNA markers (normalized by beta-actin) across each cyst category (see, Example VI).

DETAILED DESCRIPTION

Figure 1A:
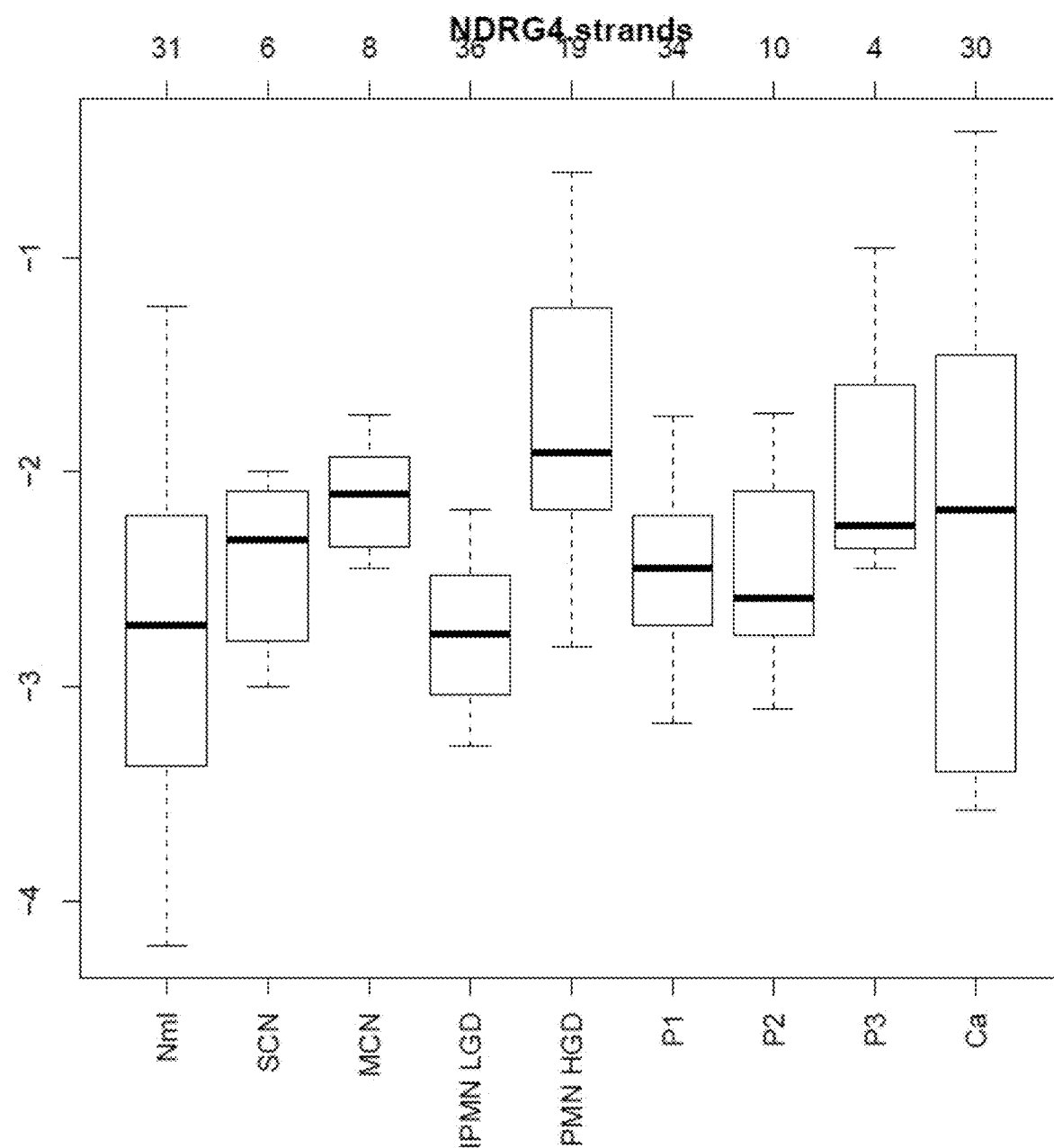
FIG. 1A-Y provides distribution plots of different markers assayed from pancreatic tissue as described in Example I.

Provided herein is technology for pancreatic high-grade dysplasia screening and particularly, but not exclusively, to methods, compositions, and related uses for detecting the presence of pancreatic high-grade dysplasia (IPMN-HGD, PanIN-3, or PDAC).

As the technology is described herein, the section headings used are for organizational purposes only and are not to be construed as limiting the subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the invention may be readily combined, without departing from the scope or spirit of the invention.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein, a "nucleic acid" or "nucleic acid molecule" generally refers to any ribonucleic acid or deoxyribonucleic acid, which may be unmodified or modified DNA or RNA. "Nucleic acids" include, without limitation, single- and double-stranded nucleic acids. As used herein, the term "nucleic acid" also includes DNA as described above that contains one or more modified bases. Thus, DNA with a backbone modified for stability or for other reasons is a "nucleic acid". The term "nucleic acid" as it is used herein embraces such chemically, enzymatically, or metabolically modified forms of nucleic acids, as well as the chemical forms of DNA characteristic of viruses and cells, including for example, simple and complex cells.

The terms "oligonucleotide" or "polynucleotide" or "nucleotide" or "nucleic acid" refer to a molecule having two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof. Typical deoxyribonucleotides for DNA are thymine, adenine, cytosine, and guanine. Typical ribonucleotides for RNA are uracil, adenine, cytosine, and guanine.

As used herein, the terms "locus" or "region" of a nucleic acid refer to a subregion of a nucleic acid, e.g., a gene on a chromosome, a single nucleotide, a CpG island, etc.

The terms "complementary" and "complementarity" refer to nucleotides (e.g., 1 nucleotide) or polynucleotides (e.g., a sequence of nucleotides) related by the base-pairing rules. For example, the sequence 5'-A-G-T-3' is complementary to the sequence 3'-T-C-A-5'. Complementarity may be "partial," in which only some of the nucleic acids' bases are matched according to the base pairing rules. Or, there may be "complete" or "total" complementarity between the nucleic acids. The degree of complementarity between nucleic acid strands effects the efficiency and strength of hybridization between nucleic acid strands. This is of particular importance in amplification reactions and in detection methods that depend upon binding between nucleic acids.

The term "gene" refers to a nucleic acid (e.g., DNA or RNA) sequence that comprises coding sequences necessary for the production of an RNA, or of a polypeptide or its precursor. A functional polypeptide can be encoded by a full length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends, e.g., for a distance of about 1 kb on either end, such that the gene corresponds to the length of the full-length mRNA (e.g., comprising coding, regulatory, structural and other sequences). The sequences that are located 5' of the coding region and that are present on the mRNA are referred to as 5' non-translated or untranslated sequences. The sequences that are located 3' or downstream of the coding region and that are present on the mRNA are referred to as 3' non-translated or 3' untranslated sequences. The term "gene" encompasses both cDNA and genomic forms of a gene. In some organisms (e.g., eukaryotes), a genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' ends of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, posttranscriptional cleavage, and polyadenylation.

The term "allele" refers to a variation of a gene; the variations include but are not limited to variants and mutants, polymorphic loci, and single nucleotide polymorphic loci, frameshift, and splice mutations. An allele may occur naturally in a population or it might arise during the lifetime of any particular individual of the population.

Thus, the terms "variant" and "mutant" when used in reference to a nucleotide sequence refer to a nucleic acid sequence that differs by one or more nucleotides from another, usually related, nucleotide acid sequence. A "variation" is a difference between two different nucleotide sequences; typically, one sequence is a reference sequence.

"Amplification" is a special case of nucleic acid replication involving template specificity. It is to be contrasted with non-specific template replication (e.g., replication that is template-dependent but not dependent on a specific template). Template specificity is here distinguished from fidelity of replication (e.g., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Amplification of nucleic acids generally refers to the production of multiple copies of a polynucleotide, or a portion of the polynucleotide, typically starting from a small amount of the polynucleotide (e.g., a single polynucleotide molecule, 10 to 100 copies of a polynucleotide molecule, which may or may not be exactly the same), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810) are forms of amplification. Additional types of amplification include, but are not limited to, allele-specific PCR (see, e.g., U.S. Pat. No. 5,639,611), assembly PCR (see, e.g., U.S. Pat. No. 5,965,408), helicase-dependent amplification (see, e.g., U.S. Pat. No. 7,662,594), Hot-start PCR (see, e.g., U.S. Pat. Nos. 5,773,258 and 5,338,671), intersequence-specfic PCR, inverse PCR (see, e.g., Triglia, et al et al. (1988) Nucleic Acids Res., 16:8186), ligation-mediated PCR (see, e.g., Guilfoyle, R. et al., Nucleic Acids Research, 25:1854-1858 (1997); U.S. Pat. No. 5,508,169), methylation-specific PCR (see, e.g., Herman, et al., (1996) PNAS 93(13) 9821-9826), miniprimer PCR, multiplex ligation-dependent probe amplification (see, e.g., Schouten, et al., (2002) Nucleic Acids Research 30(12): e57), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80), nested PCR, overlap-extension PCR (see, e.g., Higuchi, et al., (1988) Nucleic Acids Research 16(15) 7351-7367), real time PCR (see, e.g., Higuchi, et al et al., (1992) Biotechnology 10:413-417; Higuchi, et al., (1993) Biotechnology 11:1026-1030), reverse transcription PCR (see, e.g., Bustin, S. A. (2000) J. Molecular Endocrinology 25:169-193), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525).

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-beta replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al, Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics 4:560). Finally, thermostable template-dependant DNA polymerases (e.g., Taq and Pfu DNA polymerases), by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "nucleic acid detection assay" refers to any method of determining the nucleotide composition of a nucleic acid of interest. Nucleic acid detection assay include but are not limited to, DNA sequencing methods, probe hybridization methods, structure specific cleavage assays (e.g., the INVADER assay, Hologic, Inc.) and are described, e.g., in U.S. Pat. Nos. 5,846,717, 5,985,557, 5,994,069, 6,001,567, 6,090,543, and 6,872,816; Lyamichev et al., Nat. Biotech., 17:292 (1999), Hall et al., PNAS, USA, 97:8272 (2000), and US 2009/0253142); enzyme mismatch cleavage methods (e.g., Variagenics, U.S. Pat. Nos. 6,110,684, 5,958,692, 5,851,770); polymerase chain reaction; branched hybridization methods (e.g., Chiron, U.S. Pat. Nos. 5,849,481, 5,710,264, 5,124,246, and 5,624,802); rolling circle replication (e.g., U.S. Pat. Nos. 6,210,884, 6,183,960 and 6,235,502); NASBA (e.g., U.S. Pat. No. 5,409,818); molecular beacon technology (e.g., U.S. Pat. No. 6,150,097); E-sensor technology (Motorola, U.S. Pat. Nos. 6,248,229, 6,221,583, 6,013,170, and 6,063,573); cycling probe technology (e.g., U.S. Pat. Nos. 5,403,711, 5,011,769, and 5,660,988); Dade Behring signal amplification methods (e.g., U.S. Pat. Nos. 6,121,001, 6,110,677, 5,914,230, 5,882,867, and 5,792,614); ligase chain reaction (e.g., Barnay Proc. Natl. Acad. Sci USA 88, 189-93 (1991)); and sandwich hybridization methods (e.g., U.S. Pat. No. 5,288,609).

The term "amplifiable nucleic acid" refers to a nucleic acid that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (e.g., in the presence of nucleotides and an inducing agent such as a DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, and the use of the method.

The term "probe" refers to an oligonucleotide (e.g., a sequence of nucleotides), whether occurring naturally as in a purified restriction digest or produced synthetically, recombinantly, or by PCR amplification, that is capable of hybridizing to another oligonucleotide of interest. A probe may be single-stranded or double-stranded. Probes are useful in the detection, identification, and isolation of particular gene sequences (e.g., a "capture probe"). It is contemplated that any probe used in the present invention may, in some embodiments, be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, "methylation" refers to cytosine methylation at positions C5 or N4 of cytosine, the N6 position of adenine, or other types of nucleic acid methylation. In vitro amplified DNA is usually unmethylated because typical in vitro DNA amplification methods do not retain the methylation pattern of the amplification template. However, "unmethylated DNA" or "methylated DNA" can also refer to amplified DNA whose original template was unmethylated or methylated, respectively.

Accordingly, as used herein a "methylated nucleotide" or a "methylated nucleotide base" refers to the presence of a methyl moiety on a nucleotide base, where the methyl moiety is not present in a recognized typical nucleotide base. For example, cytosine does not contain a methyl moiety on its pyrimidine ring, but 5-methylcytosine contains a methyl moiety at position 5 of its pyrimidine ring. Therefore, cytosine is not a methylated nucleotide and 5-methylcytosine is a methylated nucleotide. In another example, thymine contains a methyl moiety at position 5 of its pyrimidine ring; however, for purposes herein, thymine is not considered a methylated nucleotide when present in DNA since thymine is a typical nucleotide base of DNA.

As used herein, a "methylated nucleic acid molecule" refers to a nucleic acid molecule that contains one or more methylated nucleotides.

As used herein, a "methylation state", "methylation profile", and "methylation status" of a nucleic acid molecule refers to the presence of absence of one or more methylated nucleotide bases in the nucleic acid molecule. For example, a nucleic acid molecule containing a methylated cytosine is considered methylated (e.g., the methylation state of the nucleic acid molecule is methylated). A nucleic acid molecule that does not contain any methylated nucleotides is considered unmethylated.

The methylation state of a particular nucleic acid sequence (e.g., a gene marker or DNA region as described herein) can indicate the methylation state of every base in the sequence or can indicate the methylation state of a subset of the bases (e.g., of one or more cytosines) within the sequence, or can indicate information regarding regional methylation density within the sequence with or without providing precise information of the locations within the sequence the methylation occurs.

The methylation state of a nucleotide locus in a nucleic acid molecule refers to the presence or absence of a methylated nucleotide at a particular locus in the nucleic acid molecule. For example, the methylation state of a cytosine at the 7th nucleotide in a nucleic acid molecule is methylated when the nucleotide present at the 7th nucleotide in the nucleic acid molecule is 5-methylcytosine. Similarly, the methylation state of a cytosine at the 7th nucleotide in a nucleic acid molecule is unmethylated when the nucleotide present at the 7th nucleotide in the nucleic acid molecule is cytosine (and not 5-methylcytosine).

The methylation status can optionally be represented or indicated by a "methylation value" (e.g., representing a methylation frequency, fraction, ratio, percent, etc.) A methylation value can be generated, for example, by quantifying the amount of intact nucleic acid present following restriction digestion with a methylation dependent restriction enzyme or by comparing amplification profiles after bisulfate reaction or by comparing sequences of bisulfite-treated and untreated nucleic acids. Accordingly, a value, e.g., a methylation value, represents the methylation status and can thus be used as a quantitative indicator of methylation status across multiple copies of a locus. This is of particular use when it is desirable to compare the methylation status of a sequence in a sample to a threshold or reference value.

As used herein, "methylation frequency" or "methylation percent (%)" refer to the number of instances in which a molecule or locus is methylated relative to the number of instances the molecule or locus is unmethylated.

As such, the methylation state describes the state of methylation of a nucleic acid (e.g., a genomic sequence). In addition, the methylation state refers to the characteristics of a nucleic acid segment at a particular genomic locus relevant to methylation. Such characteristics include, but are not limited to, whether any of the cytosine (C) residues within this DNA sequence are methylated, the location of methylated C residue(s), the frequency or percentage of methylated C throughout any particular region of a nucleic acid, and allelic differences in methylation due to, e.g., difference in the origin of the alleles. The terms "methylation state", "methylation profile", and "methylation status" also refer to the relative concentration, absolute concentration, or pattern of methylated C or unmethylated C throughout any particular region of a nucleic acid in a biological sample. For example, if the cytosine (C) residue(s) within a nucleic acid sequence are methylated it may be referred to as "hypermethylated" or having "increased methylation", whereas if the cytosine (C) residue(s) within a DNA sequence are not methylated it may be referred to as "hypomethylated" or having "decreased methylation". Likewise, if the cytosine (C) residue(s) within a nucleic acid sequence are methylated as compared to another nucleic acid sequence (e.g., from a different region or from a different individual, etc.) that sequence is considered hypermethylated or having increased methylation compared to the other nucleic acid sequence. Alternatively, if the cytosine (C) residue(s) within a DNA sequence are not methylated as compared to another nucleic acid sequence (e.g., from a different region or from a different individual, etc.) that sequence is considered hypomethylated or having decreased methylation compared to the other nucleic acid sequence. Additionally, the term "methylation pattern" as used herein refers to the collective sites of methylated and unmethylated nucleotides over a region of a nucleic acid. Two nucleic acids may have the same or similar methylation frequency or methylation percent but have different methylation patterns when the number of methylated and unmethylated nucleotides are the same or similar throughout the region but the locations of methylated and unmethylated nucleotides are different. Sequences are said to be "differentially methylated" or as having a "difference in methylation" or having a "different methylation state" when they differ in the extent (e.g., one has increased or decreased methylation relative to the other), frequency, or pattern of methylation. The term "differential methylation" refers to a difference in the level or pattern of nucleic acid methylation in a cancer positive sample as compared with the level or pattern of nucleic acid methylation in a cancer negative sample. It may also refer to the difference in levels or patterns between patients that have recurrence of cancer after surgery versus patients who not have recurrence. Differential methylation and specific levels or patterns of DNA methylation are prognostic and predictive biomarkers, e.g., once the correct cut-off or predictive characteristics have been defined.

Methylation state frequency can be used to describe a population of individuals or a sample from a single individual. For example, a nucleotide locus having a methylation state frequency of 50% is methylated in 50% of instances and unmethylated in 50% of instances. Such a frequency can be used, for example, to describe the degree to which a nucleotide locus or nucleic acid region is methylated in a population of individuals or a collection of nucleic acids. Thus, when methylation in a first population or pool of nucleic acid molecules is different from methylation in a second population or pool of nucleic acid molecules, the methylation state frequency of the first population or pool will be different from the methylation state frequency of the second population or pool. Such a frequency also can be used, for example, to describe the degree to which a nucleotide locus or nucleic acid region is methylated in a single individual. For example, such a frequency can be used to describe the degree to which a group of cells from a tissue sample are methylated or unmethylated at a nucleotide locus or nucleic acid region.

As used herein a "nucleotide locus" refers to the location of a nucleotide in a nucleic acid molecule. A nucleotide locus of a methylated nucleotide refers to the location of a methylated nucleotide in a nucleic acid molecule.

Typically, methylation of human DNA occurs on a dinucleotide sequence including an adjacent guanine and cytosine where the cytosine is located 5' of the guanine (also termed CpG dinucleotide sequences). Most cytosines within the CpG dinucleotides are methylated in the human genome, however some remain unmethylated in specific CpG dinucleotide rich genomic regions, known as CpG islands (see, e.g, Antequera et al. (1990) Cell 62: 503-514).

As used herein, a "CpG island" refers to a G:C-rich region of genomic DNA containing an increased number of CpG dinucleotides relative to total genomic DNA. A CpG island can be at least 100, 200, or more base pairs in length, where the G:C content of the region is at least 50% and the ratio of observed CpG frequency over expected frequency is 0.6; in some instances, a CpG island can be at least 500 base pairs in length, where the G:C content of the region is at least 55%) and the ratio of observed CpG frequency over expected frequency is 0.65. The observed CpG frequency over expected frequency can be calculated according to the method provided in Gardiner-Garden et al (1987) J. Mol. Biol. 196: 261-281. For example, the observed CpG frequency over expected frequency can be calculated according to the formula $R=(A \times B)/(C \times D)$, where R is the ratio of observed CpG frequency over expected frequency, A is the number of CpG dinucleotides in an analyzed sequence, B is the total number of nucleotides in the analyzed sequence, C is the total number of C nucleotides in the analyzed sequence, and D is the total number of G nucleotides in the analyzed sequence. Methylation state is typically determined in CpG islands, e.g., at promoter regions. It will be appreciated though that other sequences in the human genome are prone to DNA methylation such as CpA and CpT (see, e.g., Ramsahoye (2000) Proc. Natl. Acad. Sci. USA 97: 5237-5242; Salmon and Kaye (1970) Biochim. Biophys. Acta. 204: 340-351; Grafstrom (1985) Nucleic Acids Res. 13: 2827-2842; Nyce (1986) Nucleic Acids Res. 14: 4353-4367; Woodcock (1987) Biochem. Biophys. Res. Commun. 145: 888-894).

As used herein, a reagent that modifies a nucleotide of the nucleic acid molecule as a function of the methylation state of the nucleic acid molecule, or a methylation-specific reagent, refers to a compound or composition or other agent that can change the nucleotide sequence of a nucleic acid molecule in a manner that reflects the methylation state of the nucleic acid molecule. Methods of treating a nucleic acid molecule with such a reagent can include contacting the nucleic acid molecule with the reagent, coupled with additional steps, if desired, to accomplish the desired change of nucleotide sequence. Such a change in the nucleic acid molecule's nucleotide sequence can result in a nucleic acid molecule in which each methylated nucleotide is modified to a different nucleotide. Such a change in the nucleic acid nucleotide sequence can result in a nucleic acid molecule in which each unmethylated nucleotide is modified to a different nucleotide. Such a change in the nucleic acid nucleotide sequence can result in a nucleic acid molecule in which each of a selected nucleotide which is unmethylated (e.g., each unmethylated cytosine) is modified to a different nucleotide. Use of such a reagent to change the nucleic acid nucleotide sequence can result in a nucleic acid molecule in which each nucleotide that is a methylated nucleotide (e.g., each methylated cytosine) is modified to a different nucleotide. As used herein, use of a reagent that modifies a selected nucleotide refers to a reagent that modifies one nucleotide of the four typically occurring nucleotides in a nucleic acid molecule (C, G, T, and A for DNA and C, G, U, and A for RNA), such that the reagent modifies the one nucleotide without modifying the other three nucleotides. In one exemplary embodiment, such a reagent modifies an unmethylated selected nucleotide to produce a different nucleotide. In another exemplary embodiment, such a reagent can deaminate unmethylated cytosine nucleotides. An exemplary reagent is bisulfite.

As used herein, the term "bisulfite reagent" refers to a reagent comprising in some embodiments bisulfite, disulfite, hydrogen sulfite, or combinations thereof to distinguish between methylated and unmethylated cytidines, e.g., in CpG dinucleotide sequences.

The term "methylation assay" refers to any assay for determining the methylation state of one or more CpG dinucleotide sequences within a sequence of a nucleic acid.

The term "MS AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al. (1997) Cancer Research 57: 594-599.

The term "MethyLight™" refers to the art-recognized fluorescence-based real-time PCR technique described by Eads et al. (1999) Cancer Res. 59: 2302-2306.

The term "HeavyMethyl™" refers to an assay wherein methylation specific blocking probes (also referred to herein as blockers) covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo & Jones (1997) Nucleic Acids Res. 25: 2529-2531.

The term "MSP" (Methylation-specific PCR) refers to the art-recognized methylation assay described by Herman et al. (1996) Proc. Natl. Acad. Sci. USA 93: 9821-9826, and by U.S. Pat. No. 5,786,146.

The term "COBRA" (Combined Bisulfite Restriction Analysis) refers to the art-recognized methylation assay described by Xiong & Laird (1997) Nucleic Acids Res. 25: 2532-2534.

The term "MCA" (Methylated CpG Island Amplification) refers to the methylation assay described by Toyota et al. (1999) Cancer Res. 59: 2307-12, and in WO 00/26401A1.

As used herein, a "selected nucleotide" refers to one nucleotide of the four typically occurring nucleotides in a nucleic acid molecule (C, G, T, and A for DNA and C, G, U, and A for RNA), and can include methylated derivatives of the typically occurring nucleotides (e.g., when C is the selected nucleotide, both methylated and unmethylated C are included within the meaning of a selected nucleotide), whereas a methylated selected nucleotide refers specifically to a methylated typically occurring nucleotide and an unmethylated selected nucleotides refers specifically to an unmethylated typically occurring nucleotide.

The terms "methylation-specific restriction enzyme" or "methylation-sensitive restriction enzyme" refers to an enzyme that selectively digests a nucleic acid dependent on the methylation state of its recognition site. In the case of a restriction enzyme that specifically cuts if the recognition site is not methylated or is hemimethylated, the cut will not take place or will take place with a significantly reduced efficiency if the recognition site is methylated. In the case of a restriction enzyme that specifically cuts if the recognition site is methylated, the cut will not take place or will take place with a significantly reduced efficiency if the recognition site is not methylated. Preferred are methylation-specific restriction enzymes, the recognition sequence of which contains a CG dinucleotide (for instance a recognition sequence such as CGCG or CCCGGG). Further preferred for some embodiments are restriction enzymes that do not cut if the cytosine in this dinucleotide is methylated at the carbon atom C5.

As used herein, a "different nucleotide" refers to a nucleotide that is chemically different from a selected nucleotide, typically such that the different nucleotide has Watson-Crick base-pairing properties that differ from the selected nucleotide, whereby the typically occurring nucleotide that is complementary to the selected nucleotide is not the same as the typically occurring nucleotide that is complementary to the different nucleotide. For example, when C is the selected nucleotide, U or T can be the different nucleotide, which is exemplified by the complementarity of C to G and the complementarity of U or T to A. As used herein, a nucleotide that is complementary to the selected nucleotide or that is complementary to the different nucleotide refers to a nucleotide that base-pairs, under high stringency conditions, with the selected nucleotide or different nucleotide with higher affinity than the complementary nucleotide's base-paring with three of the four typically occurring nucleotides. An example of complementarity is Watson-Crick base pairing in DNA (e.g., A-T and C-G) and RNA (e.g., A-U and C-G). Thus, for example, G base-pairs, under high stringency conditions, with higher affinity to C than G base-pairs to G, A, or T and, therefore, when C is the selected nucleotide, G is a nucleotide complementary to the selected nucleotide.

As used herein, the "sensitivity" of a given marker refers to the percentage of samples that report a DNA methylation value above a threshold value that distinguishes between neoplastic and non-neoplastic samples. In some embodiments, a positive is defined as a histology-confirmed neoplasia that reports a DNA methylation value above a threshold value (e.g., the range associated with disease), and a false negative is defined as a histology-confirmed neoplasia that reports a DNA methylation value below the threshold value (e.g., the range associated with no disease). The value of sensitivity, therefore, reflects the probability that a DNA methylation measurement for a given marker obtained from a known diseased sample will be in the range of disease-associated measurements. As defined here, the clinical relevance of the calculated sensitivity value represents an estimation of the probability that a given marker would detect the presence of a clinical condition when applied to a subject with that condition.

As used herein, the "specificity" of a given marker refers to the percentage of non-neoplastic samples that report a DNA methylation value below a threshold value that distinguishes between neoplastic and non-neoplastic samples. In some embodiments, a negative is defined as a histology-confirmed non-neoplastic sample that reports a DNA methylation value below the threshold value (e.g., the range associated with no disease) and a false positive is defined as a histology-confirmed non-neoplastic sample that reports a DNA methylation value above the threshold value (e.g., the range associated with disease). The value of specificity, therefore, reflects the probability that a DNA methylation measurement for a given marker obtained from a known non-neoplastic sample will be in the range of non-disease associated measurements. As defined here, the clinical relevance of the calculated specificity value represents an estimation of the probability that a given marker would detect the absence of a clinical condition when applied to a patient without that condition.

The term "AUC" as used herein is an abbreviation for the "area under a curve". In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a diagnostic test (the larger the area the better; the optimum is 1; a random test would have a ROC curve lying on the diagonal with an area of 0.5; for reference: J. P. Egan. (1975) Signal Detection Theory and ROC Analysis, Academic Press, New York).

As used herein, the term "neoplasm" refers to "an abnormal mass of tissue, the growth of which exceeds and is uncoordinated with that of the normal tissues" See, e.g., Willis R A, "The Spread of Tumors in the Human Body", London, Butterworth & Co, 1952.

As used herein, the term "adenoma" refers to a benign tumor of glandular origin. Although these growths are benign, over time they may progress to become malignant.

The term "pre-cancerous" or "pre-neoplastic" and equivalents thereof refer to any cellular proliferative disorder that is undergoing malignant transformation.

A "site" or "region" of a neoplasm, adenoma, cancer, etc. is the tissue, organ, cell type, anatomical area, body part, etc. in a subject's body where the neoplasm, adenoma, cancer, etc. is located.

As used herein, a "diagnostic" test application includes the detection or identification of a disease state or condition of a subject, determining the likelihood that a subject will contract a given disease or condition, determining the likelihood that a subject with a disease or condition will respond to therapy, determining the prognosis of a subject with a disease or condition (or its likely progression or regression), and determining the effect of a treatment on a subject with a disease or condition. For example, a diagnostic can be used for detecting the presence or likelihood of a subject contracting a neoplasm or the likelihood that such a subject will respond favorably to a compound (e.g., a pharmaceutical, e.g., a drug) or other treatment.

The term "marker", as used herein, refers to a substance (e.g., a nucleic acid or a region of a nucleic acid) that is able to diagnose a disorder (e.g., a non-cancerous disorder) (e.g., a cancerous disorder) by distinguishing disorder-associated cells (e.g., non-cancerous cells associated with the disorder) (e.g., cancerous cells associated with the disorder) from normal cells, e.g., based its methylation state.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. Examples of non-isolated nucleic acids include: a given DNA sequence (e.g., a gene) found on the host cell chromosome in proximity to neighboring genes; RNA sequences, such as a specific mRNA sequence encoding a specific protein, found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may be single-stranded), but may contain both the sense and anti-sense strands (i.e., the oligonucleotide may be double-stranded). An isolated nucleic acid may, after isolation from its natural or typical environment, by be combined with other nucleic acids or molecules. For example, an isolated nucleic acid may be present in a host cell in which into which it has been placed, e.g., for heterologous expression.

The term "purified" refers to molecules, either nucleic acid or amino acid sequences that are removed from their natural environment, isolated, or separated. An "isolated nucleic acid sequence" may therefore be a purified nucleic acid sequence. "Substantially purified" molecules are at least 60% free, preferably at least 75% free, and more preferably at least 90% free from other components with which they are naturally associated. As used herein, the terms "purified" or "to purify" also refer to the removal of contaminants from a sample. The removal of contaminating proteins results in an increase in the percent of polypeptide or nucleic acid of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "composition comprising" a given polynucleotide sequence or polypeptide refers broadly to any composition containing the given polynucleotide sequence or polypeptide. The composition may comprise an aqueous solution containing salts (e.g., NaCl), detergents (e.g., SDS), and other components (e.g., Denhardt's solution, dry milk, salmon sperm DNA, etc.).

The term "sample" is used in its broadest sense. In one sense it can refer to an animal cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention As used herein, a "remote sample" as used in some contexts relates to a sample indirectly collected from a site that is not the cell, tissue, or organ source of the sample. For instance, when sample material originating from the pancreas is assessed in a stool sample (e.g., not from a sample taken directly from a pancreas), the sample is a remote sample.

As used herein, the terms "patient" or "subject" refer to organisms to be subject to various tests provided by the technology. The term "subject" includes animals, preferably mammals, including humans. In a preferred embodiment, the subject is a primate. In an even more preferred embodiment, the subject is a human.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

Embodiments of the Technology

In contrast to traditional views that pancreatic cancer is an inherently fast-growing malignancy with inevitably high mortality, recent computational models suggest that it may take an average of 20 years for progression from molecular initiation through precancer development, cancer evolution, and metastases (see, Yachida, S., et al., Nature, 2010. 467(7319): p. 1114-1117) much like the growth rates and natural history of colorectal neoplasia (see, Stryker, S. J., et al., Gastroenterology, 1987. 93(5): p. 1009-13; Bozic, I., et al., Proceedings of the National Academy of Sciences of the United States of America, 2010. 107(43): p. 18545-50). The long pre-symptomatic dwell time at both precancer and early T1 cancer stages may actually provide a relatively long window of opportunity for screen detection.

Cancer precursor lesions in the pancreas are well-described histologically (see, Zamboni, G., et al., Clinical gastroenterology, 2013. 27(2): p. 299-322). These lesions are remarkably common, occurring in 13-25% of the general population and offer screening targets that could potentially translate into pancreatic cancer prevention. However, their detection is currently haphazard and their management problematic. They rarely cause symptoms and are currently detected primarily as incidental findings. The most prevalent type, pancreatic intra-epithelial neoplasia (PanIN), is difficult to detect by imaging and is largely a histologic finding. Precancers detectable by imaging are typically cystic and include serous cystadenomas which are usually innocuous, intraductal papillary mucinous neoplasms (IPMNs) which have intermediate risk of progression, and mucinous cystic neoplasms which have high malignant potential (see, Morris-Stiff, G., et al., HPB: the official journal of the International Hepato Pancreato Biliary Association, 2013. 15(3): p. 175-81). Most precancers do not progress, and available approaches to predicting risk are imperfect. Currently-used scoring systems based on radiographic structural features, cytologic sampling, or molecular testing have failed to accurately predict histology (see, Correa-Gallego, C., et al., Pancreatology: official journal of the International Association of Pancreatology, 2010. 10(2-3): p. 144-50). Consequently, many lesions triggering pancreatic resection prove to be non-neoplastic or contain no high grade dysplasia (see, Correa-Gallego, C., et al., Pancreatology: official journal of the International Association of Pancreatology, 2010. 10(2-3): p. 144-50).

The slow natural history of pancreatic cancer progression offers ample opportunity for detection of curable pancreatic neoplasia. The innovation challenge is to develop noninvasive or minimally invasive tools with high clinical sensitivity and with the ability to accurately discriminate precancers with high grade dysplasia that are most suitable for resection.

Experiments conducted during the course of developing embodiments for the present invention compared the methylation state of DNA markers from pancreatic tissue of subjects having IPMN-HGD, PanIN-3, or PDAC to the methylation state of the same DNA markers from control subjects (e.g., subjects having IPMN-low grade dysplasia (IPMN-LGD), PanIN-1, and PanIN-2 for the respective tissue type). Such experiments identified and validated methylated DNA marker candidates that discriminate a case group with high-grade precursors (IPMN-HGD, PanIN-3) or invasive cancer (PDAC) from a control group with either normal pancreas or low-grade precursor lesions (IPMN-low grade dysplasia (IPMN-LGD), PanIN-1, and PanIN-2) (see, Examples I, II, IV and V).

Accordingly, provided herein is technology for pancreatic high-grade dysplasia screening (e.g., surveilling) and particularly, but not exclusively, to methods, compositions, and related uses for detecting the presence of pancreatic high-grade dysplasia (IPMN-HGD, PanIN-3, or PDAC) in subjects.

Markers and/or panels of markers were identified (e.g., a chromosomal region having an annotation provided in Tables 2 and 6) capable of detecting pancreatic high-grade dysplasia (IPMN-HGD, PanIN-3, or PDAC) (see, Examples I, II, IV and V) (BMP3, NDRG4, ABCB1, AK055957, C13ORF18, CD1D, CLEC11A, DLX4, ELMO1, EMX1, FER1L4, FRMD4A, GRIN2D, HOXA1, LRRC4, PRKCB, SP9, ST6GAL2, ST8SIA1, TBX15, VWC2, and ZNF781).

Although the disclosure herein refers to certain illustrated embodiments, it is to be understood that these embodiments are presented by way of example and not by way of limitation.

The methods comprise determining the methylation status of at least one methylation marker in a biological sample isolated from a subject, wherein a change in the methylation state of the marker is indicative of the presence, or class of pancreatic high-grade dysplasia (IPMN-HGD, PanIN-3, or PDAC). Particular embodiments relate to markers comprising a differentially methylated region (DMR, e.g., DMR 1-96 or DMR 1, 21, 24, 25, 26, 55, 70, 77, 81, 84, 92, 95 and 96 (from Tables 2 and 6)) that are used for diagnosis (e.g., screening) of pancreatic high-grade dysplasia (IPMN-HGD, PanIN-3, or PDAC).

In addition to embodiments wherein the methylation analysis of at least one marker, a region of a marker, or a base of a marker comprising a DMR (e.g., DMR 1-96 or DMR 1, 21, 24, 25, 26, 55, 70, 77, 81, 84, 92, 95 and 96) provided herein and listed in Tables 2 and 6 is analyzed, the technology also provides panels of markers comprising at least one marker, region of a marker, or base of a marker comprising a DMR with utility for the detection of pancreatic high-grade dysplasia (IPMN-HGD, PanIN-3, or PDAC) in a subject.

Some embodiments of the technology are based upon the analysis of the CpG methylation status of at least one marker, region of a marker, or base of a marker comprising a DMR.

In some embodiments, the present technology provides for the use of the bisulfite technique in combination with one or more methylation assays to determine the methylation status of CpG dinucleotide sequences within at least one marker comprising a DMR (e.g., as provided in Tables 2 and 6 (e.g., DMR 1-96)). Genomic CpG dinucleotides can be methylated or unmethylated (alternatively known as up- and down-methylated respectively). However the methods of the present invention are suitable for the analysis of biological samples of a heterogeneous nature, e.g., a low concentration of tumor cells, or biological materials therefrom, within a background of a remote sample (e.g., blood, organ effluent, or stool). Accordingly, when analyzing the methylation status of a CpG position within such a sample one may use a quantitative assay for determining the level (e.g., percent, fraction, ratio, proportion, or degree) of methylation at a particular CpG position.

According to the present technology, determination of the methylation status of CpG dinucleotide sequences in markers comprising a DMR has utility both in the diagnosis and characterization of pancreatic high-grade dysplasia (IPMN-HGD, PanIN-3, or PDAC) in subjects.

Combinations of Markers

In some embodiments, the technology relates to assessing the methylation state of combinations of markers comprising two or more DMRs from Tables 2 and 6 (e.g., two or more DMRs from DMR Nos. 1-96). In some embodiments, assessing the methylation state of more than one marker increases the specificity and/or sensitivity of a screen or diagnostic for identifying the presence of pancreatic high-grade dysplasia (IPMN-HGD, PanIN-3, or PDAC) in a subject.

Various cancers are predicted by various combinations of markers, e.g., as identified by statistical techniques related to specificity and sensitivity of prediction. The technology provides methods for identifying predictive combinations and validated predictive combinations for some cancers.

In some embodiments, combinations of markers (e.g., comprising a DMR) predict the site of a neoplasm.

For example, markers and/or panels of markers were identified (e.g., a chromosomal region having an annotation provided in Tables 2 and 6) capable of detecting pancreatic high-grade dysplasia (IPMN-HGD, PanIN-3, or PDAC) (see, Examples I, II, IV and V) (BMP3, NDRG4, ABCB1, AK055957, C13ORF18, CD1D, CLEC11A, DLX4, ELMO1, EMX1, FER1L4, FRMD4A, GRIN2D, HOXA1, LRRC4, PRKCB, SP9, ST6GAL2, ST8SIA1, TBX15, VWC2, and ZNF781).

Methods for Assaying Methylation State

The most frequently used method for analyzing a nucleic acid for the presence of 5-methylcytosine is based upon the bisulfite method described by Frommer, et al. for the detection of 5-methylcytosines in DNA (Frommer et al. (1992) Proc. Natl. Acad. Sci. USA 89: 1827-31) or variations thereof. The bisulfite method of mapping 5-methylcytosines is based on the observation that cytosine, but not 5-methylcytosine, reacts with hydrogen sulfite ion (also known as bisulfite). The reaction is usually performed according to the following steps: first, cytosine reacts with hydrogen sulfite to form a sulfonated cytosine. Next, spontaneous deamination of the sulfonated reaction intermediate results in a sulfonated uracil. Finally, the sulfonated uricil is desulfonated under alkaline conditions to form uracil. Detection is possible because uracil forms base pairs with adenine (thus behaving like thymine), whereas 5-methylcytosine base pairs with guanine (thus behaving like cytosine). This makes the discrimination of methylated cytosines from non-methylated cytosines possible by, e.g., bisulfite genomic sequencing (Grigg G, & Clark S, Bioessays (1994) 16: 431-36; Grigg G, DNA Seq. (1996) 6: 189-98) or methylation-specific PCR (MSP) as is disclosed, e.g., in U.S. Pat. No. 5,786,146.

Some conventional technologies are related to methods comprising enclosing the DNA to be analyzed in an agarose matrix, thereby preventing the diffusion and renaturation of the DNA (bisulfite only reacts with single-stranded DNA), and replacing precipitation and purification steps with a fast dialysis (Olek A, et al. (1996) "A modified and improved method for bisulfite based cytosine methylation analysis" Nucleic Acids Res. 24: 5064-6). It is thus possible to analyze individual cells for methylation status, illustrating the utility and sensitivity of the method. An overview of conventional methods for detecting 5-methylcytosine is provided by Rein, T., et al. (1998) Nucleic Acids Res. 26: 2255.

The bisulfite technique typically involves amplifying short, specific fragments of a known nucleic acid subsequent to a bisulfite treatment, then either assaying the product by sequencing (Olek & Walter (1997) Nat. Genet. 17: 275-6) or a primer extension reaction (Gonzalgo & Jones (1997) Nucleic Acids Res. 25: 2529-31; WO 95/00669; U.S. Pat. No. 6,251,594) to analyze individual cytosine positions. Some methods use enzymatic digestion (Xiong & Laird (1997) Nucleic Acids Res. 25: 2532-4). Detection by hybridization has also been described in the art (Olek et al., WO 99/28498). Additionally, use of the bisulfite technique for methylation detection with respect to individual genes has been described (Grigg & Clark (1994) Bioessays 16: 431-6; Zeschnigk et al. (1997) Hum Mol Genet. 6: 387-95; Feil et al. (1994) Nucleic Acids Res. 22: 695; Martin et al. (1995) Gene 157: 261-4; WO 9746705; WO 9515373).

Various methylation assay procedures are known in the art and can be used in conjunction with bisulfite treatment according to the present technology. These assays allow for determination of the methylation state of one or a plurality of CpG dinucleotides (e.g., CpG islands) within a nucleic acid sequence. Such assays involve, among other techniques, sequencing of bisulfite-treated nucleic acid, PCR (for sequence-specific amplification), Southern blot analysis, and use of methylation-sensitive restriction enzymes.

For example, genomic sequencing has been simplified for analysis of methylation patterns and 5-methylcytosine distributions by using bisulfite treatment (Frommer et al. (1992) Proc. Natl. Acad. Sci. USA 89: 1827-1831). Additionally, restriction enzyme digestion of PCR products amplified from bisulfite-converted DNA finds use in assessing methylation state, e.g., as described by Sadri & Hornsby (1997) Nucl. Acids Res. 24: 5058-5059 or as embodied in the method known as COBRA (Combined Bisulfite Restriction Analysis) (Xiong & Laird (1997) Nucleic Acids Res. 25: 2532-2534).

COBRA™ analysis is a quantitative methylation assay useful for determining DNA methylation levels at specific loci in small amounts of genomic DNA (Xiong & Laird, Nucleic Acids Res. 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (Proc. Natl. Acad. Sci. USA 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from microdissected paraffin-embedded tissue samples.

Typical reagents (e.g., as might be found in a typical COBRA™-based kit) for COBRA™ analysis may include, but are not limited to: PCR primers for specific loci (e.g., specific genes, markers, DMR, regions of genes, regions of markers, bisulfite treated DNA sequence, CpG island, etc.); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., Cancer Res. 59:2302-2306, 1999), Ms-SNuPE™ (Methylation-sensitive Single Nucleotide Primer Extension) reactions (Gonzalgo & Jones, Nucleic Acids Res. 25:2529-2531, 1997), methylation-specific PCR ("MSP"; Herman et al., Proc. Natl. Acad. Sci. USA 93:9821-9826, 1996; U.S. Pat. No.

5,786,146), and methylated CpG island amplification ("MCA"; Toyota et al., Cancer Res. 59:2307-12, 1999) are used alone or in combination with one or more of these methods.

The "HeavyMethyl™" assay, technique is a quantitative method for assessing methylation differences based on methylation-specific amplification of bisulfite-treated DNA. Methylation-specific blocking probes ("blockers") covering CpG positions between, or covered by, the amplification primers enable methylation-specific selective amplification of a nucleic acid sample.

The term "HeavyMethyl™ MethyLight™" assay refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific loci (e.g., specific genes, markers, DMR, regions of genes, regions of markers, bisulfite treated DNA sequence, CpG island, or bisulfite treated DNA sequence or CpG island, etc.); blocking oligonucleotides; optimized PCR buffers and deoxynucleotides; and Taq polymerase.

MSP (methylation-specific PCR) allows for assessing the methylation status of virtually any group of CpG sites within a CpG island, independent of the use of methylation-sensitive restriction enzymes (Herman et al. Proc. Natl. Acad. Sci. USA 93:9821-9826, 1996; U.S. Pat. No. 5,786,146). Briefly, DNA is modified by sodium bisulfite, which converts unmethylated, but not methylated cytosines, to uracil, and the products are subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific loci (e.g., specific genes, markers, DMR, regions of genes, regions of markers, bisulfite treated DNA sequence, CpG island, etc.); optimized PCR buffers and deoxynucleotides, and specific probes.

The MethyLight™ assay is a high-throughput quantitative methylation assay that utilizes fluorescence-based real-time PCR (e.g., TaqMan®) that requires no further manipulations after the PCR step (Eads et al., Cancer Res. 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" reaction, e.g., with PCR primers that overlap known CpG dinucleotides. Sequence discrimination occurs both at the level of the amplification process and at the level of the fluorescence detection process.

The MethyLight™ assay is used as a quantitative test for methylation patterns in a nucleic acid, e.g., a genomic DNA sample, wherein sequence discrimination occurs at the level of probe hybridization. In a quantitative version, the PCR reaction provides for a methylation specific amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (e.g., a fluorescence-based version of the HeavyMethyl™ and MSP techniques) or with oligonucleotides covering potential methylation sites.

The MethyLight™ process is used with any suitable probe (e.g. a "TaqMan®" probe, a Lightcycler® probe, etc.) For example, in some applications double-stranded genomic DNA is treated with sodium bisulfite and subjected to one of two sets of PCR reactions using TaqMan® probes, e.g., with MSP primers and/or HeavyMethyl blocker oligonucleotides and a TaqMan® probe. The TaqMan® probe is dual-labeled with fluorescent "reporter" and "quencher" molecules and is designed to be specific for a relatively high GC content region so that it melts at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe, overlie any CpG dinucleotides. Alternatively, a qualitative test for genomic methylation is achieved by probing the biased PCR pool with either control oligonucleotides that do not cover known methylation sites (a fluorescence-based version of the HeavyMethyl™ and MSP techniques) or with oligonucleotides covering potential methylation sites.

The QM™ process can be used with any suitable probe, e.g., "TaqMan®" probes, Lightcycler® probes, in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about a 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific loci (e.g., specific genes, markers, DMR, regions of genes, regions of markers, bisulfite treated DNA sequence, CpG island, etc.); TaqMan® or Lightcycler® probes; optimized PCR buffers and deoxynucleotides; and Taq polymerase.

The Ms-SNuPE™ technique is a quantitative method for assessing methylation differences at specific CpG sites based on bisulfite treatment of DNA, followed by single-nucleotide primer extension (Gonzalgo & Jones, Nucleic Acids Res. 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site of interest. Small amounts of DNA can be analyzed (e.g., microdissected pathology sections) and it avoids utilization of restriction enzymes for determining the methylation status at CpG sites.

Typical reagents (e.g., as might be found in a typical Ms-SNuPE™-based kit) for Ms-SNuPE™ analysis may include, but are not limited to: PCR primers for specific loci (e.g., specific genes, markers, DMR, regions of genes, regions of markers, bisulfite treated DNA sequence, CpG island, etc.); optimized PCR buffers and deoxynucleotides; gel extraction kit; positive control primers; Ms-SNuPE™ primers for specific loci; reaction buffer (for the Ms-SNuPE reaction); and labeled nucleotides. Additionally, bisulfite conversion reagents may include: DNA denaturation buffer; sulfonation buffer; DNA recovery reagents or kit (e.g., precipitation, ultrafiltration, affinity column); desulfonation buffer; and DNA recovery components.

Reduced Representation Bisulfite Sequencing (RRBS) begins with bisulfite treatment of nucleic acid to convert all unmethylated cytosines to uracil, followed by restriction enzyme digestion (e.g., by an enzyme that recognizes a site including a CG sequence such as MspI) and complete sequencing of fragments after coupling to an adapter ligand. The choice of restriction enzyme enriches the fragments for CpG dense regions, reducing the number of redundant sequences that may map to multiple gene positions during analysis. As such, RRBS reduces the complexity of the nucleic acid sample by selecting a subset (e.g., by size selection using preparative gel electrophoresis) of restriction fragments for sequencing. As opposed to whole-genome bisulfite sequencing, every fragment produced by the restriction enzyme digestion contains DNA methylation information for at least one CpG dinucleotide. As such, RRBS enriches the sample for promoters, CpG islands, and other genomic features with a high frequency of restriction enzyme cut sites in these regions and thus provides an assay to assess the methylation state of one or more genomic loci.

A typical protocol for RRBS comprises the steps of digesting a nucleic acid sample with a restriction enzyme such as MspI, filling in overhangs and A-tailing, ligating adaptors, bisulfite conversion, and PCR. See, e.g., et al. (2005) "Genome-scale DNA methylation mapping of clinical samples at single-nucleotide resolution" Nat Methods 7: 133-6; Meissner et al. (2005) "Reduced representation bisulfite sequencing for comparative high-resolution DNA methylation analysis" Nucleic Acids Res. 33: 5868-77.

In some embodiments, a quantitative allele-specific real-time target and signal amplification (QUARTS) assay is used to evaluate methylation state. Three reactions sequentially occur in each QUARTS assay, including amplification (reaction 1) and target probe cleavage (reaction 2) in the primary reaction; and FRET cleavage and fluorescent signal generation (reaction 3) in the secondary reaction. When target nucleic acid is amplified with specific primers, a specific detection probe with a flap sequence loosely binds to the amplicon. The presence of the specific invasive oligonucleotide at the target binding site causes cleavase to release the flap sequence by cutting between the detection probe and the flap sequence. The flap sequence is complementary to a nonhairpin portion of a corresponding FRET cassette. Accordingly, the flap sequence functions as an invasive oligonucleotide on the FRET cassette and effects a cleavage between the FRET cassette fluorophore and a quencher, which produces a fluorescent signal. The cleavage reaction can cut multiple probes per target and thus release multiple fluorophore per flap, providing exponential signal amplification. QuARTS can detect multiple targets in a single reaction well by using FRET cassettes with different dyes. See, e.g., in Zou et al. (2010) "Sensitive quantification of methylated markers with a novel methylation specific technology" Clin Chem 56: A199; U.S. patent application Ser. Nos. 12/946,737, 12/946,745, 12/946,752, and 61/548,639.

The term "bisulfite reagent" refers to a reagent comprising bisulfite, disulfite, hydrogen sulfite, or combinations thereof, useful as disclosed herein to distinguish between methylated and unmethylated CpG dinucleotide sequences. Methods of said treatment are known in the art (e.g., PCT/EP2004/011715). It is preferred that the bisulfite treatment is conducted in the presence of denaturing solvents such as but not limited to n-alkylenglycol or diethylene glycol dimethyl ether (DME), or in the presence of dioxane or dioxane derivatives. In some embodiments the denaturing solvents are used in concentrations between 1% and 35% (v/v). In some embodiments, the bisulfite reaction is carried out in the presence of scavengers such as but not limited to chromane derivatives, e.g., 6-hydroxy-2,5,7,8,-tetramethylchromane 2-carboxylic acid or trihydroxybenzone acid and derivates thereof, e.g., Gallic acid (see: PCT/EP2004/011715). The bisulfite conversion is preferably carried out at a reaction temperature between 30° C. and 70° C., whereby the temperature is increased to over 85° C. for short times during the reaction (see: PCT/EP2004/011715). The bisulfite treated DNA is preferably purified prior to the quantification. This may be conducted by any means known in the art, such as but not limited to ultrafiltration, e.g., by means of Microcon™ columns (manufactured by Millipore™). The purification is carried out according to a modified manufacturer's protocol (see, e.g., PCT/EP2004/011715).

In some embodiments, fragments of the treated DNA are amplified using sets of primer oligonucleotides according to the present invention (e.g., see Tables 3 and 7) and an amplification enzyme. The amplification of several DNA segments can be carried out simultaneously in one and the same reaction vessel. Typically, the amplification is carried out using a polymerase chain reaction (PCR). Amplicons are typically 100 to 2000 base pairs in length.

In another embodiment of the method, the methylation status of CpG positions within or near a marker comprising a DMR (e.g., DMR 1-96; Tables 2 and 6) may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primer pairs contain at least one primer that hybridizes to a bisulfite treated CpG dinucleotide. Therefore, the sequence of said primers comprises at least one CpG dinucleotide. MSP primers specific for non-methylated DNA contain a "T" at the position of the C position in the CpG.

The fragments obtained by means of the amplification can carry a directly or indirectly detectable label. In some embodiments, the labels are fluorescent labels, radionuclides, or detachable molecule fragments having a typical mass that can be detected in a mass spectrometer. Where said labels are mass labels, some embodiments provide that the labeled amplicons have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Methods for isolating DNA suitable for these assay technologies are known in the art. In particular, some embodiments comprise isolation of nucleic acids as described in U.S. patent application Ser. No. 13/470,251 ("Isolation of Nucleic Acids").

Methods

In some embodiments the technology, methods are provided that comprise the following steps:
1) contacting a nucleic acid (e.g., genomic DNA, e.g., isolated from a body fluids such as a stool sample, a blood sample, or a tissue sample (e.g., pancreatic tissue)) obtained from a subject with at least one reagent or series of reagents that distinguishes between methylated and non-methylated CpG dinucleotides within at least one marker comprising a DMR (e.g., DMR 1-96 or DMR 1, 21, 24, 25, 26, 55, 70, 77, 81, 84, and 92, 95 and 96 (from Tables 2 and 6)) and
2) detecting a lack of pancreatic high-grade dysplasia (IPMN-HGD, PanIN-3, or PDAC) (e.g., afforded with a sensitivity of greater than or equal to 80% and a specificity of greater than or equal to 80%).

In some embodiments the technology, methods are provided that comprise the following steps:
1) contacting a nucleic acid (e.g., genomic DNA, e.g., isolated from a body fluids such as a stool sample, a blood sample, or a tissue sample (e.g., pancreatic tissue)) obtained from a subject with at least one reagent or series of reagents that distinguishes between methylated and non-methylated CpG dinucleotides within at least one marker comprising a DMR (e.g., DMR 1-96 or DMR 1, 21, 24, 25, 26, 55, 70, 77, 81, 84, and 92, 95 and 96 (from Tables 2 and 6)) and
2) classifying pancreatic high-grade dysplasia (IPMN-HGD, PanIN-3, or PDAC) (e.g., afforded with a sensitivity of greater than or equal to 80% and a specificity of greater than or equal to 80%).

Preferably, the sensitivity is from about 70% to about 100%, or from about 80% to about 90%, or from about 80% to about 85%. Preferably, the specificity is from about 70% to about 100%, or from about 80% to about 90%, or from about 80% to about 85%.

Genomic DNA may be isolated by any means, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants, e.g., by digestion with proteinase K. The genomic DNA is then recovered from the solution. This may be carried out by means of a variety of methods including salting out, organic extraction, or binding of the DNA to a solid phase support. The choice of method will be affected by several factors including time, expense, and required quantity of DNA. All clinical sample types comprising neoplastic matter or pre-neoplastic matter are suitable for use in the present method, e.g., cell lines, histological slides, biopsies, paraffin-embedded tissue, body fluids, stool, colonic effluent, urine, blood plasma, blood serum, whole blood, isolated blood cells, cells isolated from the blood, and combinations thereof.

In some embodiments wherein the sample includes pancreatic tissue and/or pancreatic juice.

The technology is not limited in the methods used to prepare the samples and provide a nucleic acid for testing. For example, in some embodiments, a DNA is isolated from a stool sample or from blood or from a plasma sample using direct gene capture, e.g., as detailed in U.S. Pat. Appl. Ser. No. 61/485,386 or by a related method.

The genomic DNA sample is then treated with at least one reagent, or series of reagents, that distinguishes between methylated and non-methylated CpG dinucleotides within at least one marker comprising a DMR (e.g., DMR 1-96, e.g., as provided by Tables 2 and 6).

In some embodiments, the reagent converts cytosine bases which are unmethylated at the 5'-position to uracil, thymine, or another base which is dissimilar to cytosine in terms of hybridization behavior. However in some embodiments, the reagent may be a methylation sensitive restriction enzyme.

In some embodiments, the genomic DNA sample is treated in such a manner that cytosine bases that are unmethylated at the 5' position are converted to uracil, thymine, or another base that is dissimilar to cytosine in terms of hybridization behavior. In some embodiments, this treatment is carried out with bisulfate (hydrogen sulfite, disulfite) followed by alkaline hydrolysis.

The treated nucleic acid is then analyzed to determine the methylation state of the target gene sequences (at least one gene, genomic sequence, or nucleotide from a marker comprising a DMR, e.g., at least one DMR chosen from DMR 1-96, e.g., as provided in Tables 2 and 6). The method of analysis may be selected from those known in the art, including those listed herein, e.g., QuARTS and MSP as described herein.

The technology relates to the analysis of any sample associated with pancreatic high-grade dysplasia (IPMN-HGD, PanIN-3, or PDAC). For example, in some embodiments the sample comprises a tissue and/or biological fluid obtained from a patient. In some embodiments, the sample comprises colorectal tissue. In some embodiments, the sample comprises a secretion. In some embodiments, the sample comprises blood, serum, plasma, gastric secretions, pancreatic juice, a gastrointestinal biopsy sample, microdissected cells from an esophageal biopsy, esophageal cells sloughed into the gastrointestinal lumen, and/or esophageal cells recovered from stool. In some embodiments, the subject is human. These samples may originate from the upper gastrointestinal tract, the lower gastrointestinal tract, or comprise cells, tissues, and/or secretions from both the upper gastrointestinal tract and the lower gastrointestinal tract. The sample may include cells, secretions, or tissues from the liver, bile ducts, pancreas, stomach, colon, rectum, esophagus, small intestine, appendix, duodenum, polyps, gall bladder, anus, and/or peritoneum. In some embodiments, the sample comprises cellular fluid, ascites, urine, feces, pancreatic fluid, fluid obtained during endoscopy, blood, mucus, or saliva. In some embodiments, the sample is a stool sample.

Such samples can be obtained by any number of means known in the art, such as will be apparent to the skilled person. For instance, urine and fecal samples are easily attainable, while blood, ascites, serum, or pancreatic fluid samples can be obtained parenterally by using a needle and syringe, for instance. Cell free or substantially cell free samples can be obtained by subjecting the sample to various techniques known to those of skill in the art which include, but are not limited to, centrifugation and filtration. Although it is generally preferred that no invasive techniques are used to obtain the sample, it still may be preferable to obtain samples such as tissue homogenates, tissue sections, and biopsy specimens.

In some embodiments of the technology, a method for diagnosing pancreatic high-grade dysplasia (IPMN-HGD, PanIN-3, or PDAC) in a subject is provided. The terms "diagnosing" and "diagnosis" as used herein refer to methods by which the skilled artisan can estimate and even determine whether or not a subject is suffering from a given disease or condition or may develop a given disease or condition in the future. The skilled artisan often makes a diagnosis on the basis of one or more diagnostic indicators, such as for example a biomarker (e.g., a DMR as disclosed herein), the methylation state of which is indicative of the presence, severity, or absence of the condition.

Along with diagnosis, clinical cancer prognosis (e.g., for pancreatic high-grade dysplasia (IPMN-HGD, PanIN-3, or PDAC)) relates to determining the aggressiveness of the cancer and the likelihood of tumor recurrence to plan the most effective therapy. If a more accurate prognosis can be made or even a potential risk for developing the cancer can be assessed, appropriate therapy, and in some instances less severe therapy for the patient can be chosen. Assessment (e.g., determining methylation state) of cancer biomarkers is useful to separate subjects with good prognosis and/or low risk of developing cancer who will need no therapy or limited therapy from those more likely to develop cancer or suffer a recurrence of cancer who might benefit from more intensive treatments.

As such, "making a diagnosis" or "diagnosing", as used herein, is further inclusive of making determining a risk of developing cancer or determining a prognosis, which can provide for predicting a clinical outcome (with or without medical treatment), selecting an appropriate treatment (or whether treatment would be effective), or monitoring a current treatment and potentially changing the treatment, based on the measure of the diagnostic biomarkers (e.g., DMR) disclosed herein. Further, in some embodiments of the presently disclosed subject matter, multiple determinations of the biomarkers over time can be made to facilitate diagnosis and/or prognosis. A temporal change in the biomarker can be used to predict a clinical outcome, monitor the progression of pancreatic high-grade dysplasia (IPMN-HGD, PanIN-3, or PDAC), and/or monitor the efficacy of appropriate therapies directed against the cancer. In such an embodiment for example, one might expect to see a change in the methylation state of one or more biomarkers (e.g., DMR) disclosed herein (and potentially one or more additional biomarker(s), if monitored) in a biological sample over time during the course of an effective therapy.

The presently disclosed subject matter further provides in some embodiments a method for determining whether to initiate or continue prophylaxis or treatment of pancreatic high-grade dysplasia (IPMN-HGD, PanIN-3, or PDAC) in a subject. In some embodiments, the method comprises providing a series of biological samples over a time period from the subject; analyzing the series of biological samples to determine a methylation state of at least one biomarker disclosed herein in each of the biological samples; and comparing any measurable change in the methylation states of one or more of the biomarkers in each of the biological samples. Any changes in the methylation states of biomarkers over the time period can be used to predict risk of developing pancreatic high-grade dysplasia (IPMN-HGD, PanIN-3, or PDAC), predict clinical outcome, determine whether to initiate or continue the prophylaxis or therapy of the cancer, and whether a current therapy is effectively treating the pancreatic high-grade dysplasia (IPMN-HGD, PanIN-3, or PDAC). For example, a first time point can be selected prior to initiation of a treatment and a second time point can be selected at some time after initiation of the treatment. Methylation states can be measured in each of the samples taken from different time points and qualitative and/or quantitative differences noted. A change in the methylation states of the biomarker levels from the different samples can be correlated with risk (e.g., risk of developing pancreatic high-grade dysplasia (IPMN-HGD, PanIN-3, or PDAC)), prognosis, determining treatment efficacy, and/or progression of the disorder in the subject.

In preferred embodiments, the methods and compositions of the invention are for treatment or diagnosis of disease at an early stage, for example, before symptoms of the disease appear. In some embodiments, the methods and compositions of the invention are for treatment or diagnosis of disease at a clinical stage.

As noted, in some embodiments, multiple determinations of one or more diagnostic or prognostic biomarkers can be made, and a temporal change in the marker can be used to determine a diagnosis or prognosis. For example, a diagnostic marker can be determined at an initial time, and again at a second time. In such embodiments, an increase in the marker from the initial time to the second time can be diagnostic of a particular type or severity of the disorder, or a given prognosis. Likewise, a decrease in the marker from the initial time to the second time can be indicative of a particular type or severity of a disorder, or a given prognosis. Furthermore, the degree of change of one or more markers can be related to the severity of the disorder and future adverse events. The skilled artisan will understand that, while in certain embodiments comparative measurements can be made of the same biomarker at multiple time points, one can also measure a given biomarker at one time point, and a second biomarker at a second time point, and a comparison of these markers can provide diagnostic information.

As used herein, the phrase "determining the prognosis" refers to methods by which the skilled artisan can predict the course or outcome of a condition in a subject. The term "prognosis" does not refer to the ability to predict the course or outcome of a condition with 100% accuracy, or even that a given course or outcome is predictably more or less likely to occur based on the methylation state of a biomarker (e.g., a DMR). Instead, the skilled artisan will understand that the term "prognosis" refers to an increased probability that a certain course or outcome will occur; that is, that a course or outcome is more likely to occur in a subject exhibiting a given condition, when compared to those individuals not exhibiting the condition. For example, in individuals not exhibiting the condition (e.g., having a normal methylation state of one or more DMR), the chance of a given outcome may be very low.

In some embodiments, a statistical analysis associates a prognostic indicator with a predisposition to an adverse outcome. For example, in some embodiments, a methylation state different from that in a normal control sample obtained from a patient who does not have a disorder can signal that a subject is more likely to suffer from a disorder than subjects with a level that is more similar to the methylation state in the control sample, as determined by a level of statistical significance. Additionally, a change in methylation state from a baseline (e.g., "normal") level can be reflective of subject prognosis, and the degree of change in methylation state can be related to the severity of adverse events. Statistical significance is often determined by comparing two or more populations and determining a confidence interval and/or a p value (see, e.g., Dowdy and Wearden, Statistics for Research, John Wiley & Sons, New York, 1983). Exemplary confidence intervals of the present subject matter are 90%, 95%, 97.5%, 98%, 99%, 99.5%, 99.9% and 99.99%, while exemplary p values are 0.1, 0.05, 0.025, 0.02, 0.01, 0.005, 0.001, and 0.0001.

In other embodiments, a threshold degree of change in the methylation state of a prognostic or diagnostic biomarker disclosed herein (e.g., a DMR) can be established, and the degree of change in the methylation state of the biomarker in a biological sample is simply compared to the threshold degree of change in the methylation state. A preferred threshold change in the methylation state for biomarkers provided herein is about 5%, about 10%, about 15%, about 20%, about 25%, about 30%, about 50%, about 75%, about 100%, and about 150%. In yet other embodiments, a "nomogram" can be established, by which a methylation state of a prognostic or diagnostic indicator (biomarker or combination of biomarkers) is directly related to an associated disposition towards a given outcome. The skilled artisan is acquainted with the use of such nomograms to relate two numeric values with the understanding that the uncertainty in this measurement is the same as the uncertainty in the marker concentration because individual sample measurements are referenced, not population averages.

In some embodiments, a control sample is analyzed concurrently with the biological sample, such that the results obtained from the biological sample can be compared to the results obtained from the control sample. Additionally, it is contemplated that standard curves can be provided, with which assay results for the biological sample may be compared. Such standard curves present methylation states of a biomarker as a function of assay units, e.g., fluorescent signal intensity, if a fluorescent label is used. Using samples taken from multiple donors, standard curves can be provided for control methylation states of the one or more biomarkers in normal tissue, as well as for "at-risk" levels of the one or more biomarkers in tissue taken from donors with metaplasia or from donors with a disorder (e.g., pancreatic high-grade dysplasia (IPMN-HGD, PanIN-3, or PDAC)). In certain embodiments of the method, a subject is identified as having pancreatic high-grade dysplasia (IPMN-HGD, PanIN-3, or PDAC) upon identifying an aberrant methylation state of one or more DMR provided herein in a biological sample obtained from the subject. In other embodiments of the method, the detection of an aberrant methylation state of one or more of such biomarkers in a biological sample obtained from the subject results in the subject being identified as having pancreatic high-grade dysplasia (IPMN-HGD, PanIN-3, or PDAC).

The analysis of markers can be carried out separately or simultaneously with additional markers within one test sample. For example, several markers can be combined into one test for efficient processing of a multiple of samples and for potentially providing greater diagnostic and/or prognostic accuracy. In addition, one skilled in the art would recognize the value of testing multiple samples (for example, at successive time points) from the same subject. Such testing of serial samples can allow the identification of changes in marker methylation states over time. Changes in methylation state, as well as the absence of change in methylation state, can provide useful information about the disease status that includes, but is not limited to, identifying the approximate time from onset of the event, the presence and amount of salvageable tissue, the appropriateness of drug therapies, the effectiveness of various therapies, and identification of the subject's outcome, including risk of future events.

The analysis of biomarkers can be carried out in a variety of physical formats. For example, the use of microtiter plates or automation can be used to facilitate the processing of large numbers of test samples. Alternatively, single sample formats could be developed to facilitate immediate treatment and diagnosis in a timely fashion, for example, in ambulatory transport or emergency room settings.

In some embodiments, the subject is diagnosed as having pancreatic high-grade dysplasia (IPMN-HGD, PanIN-3, or PDAC) if, when compared to a control methylation state, there is a measurable difference in the methylation state of at least one biomarker in the sample. Conversely, when no change in methylation state is identified in the biological sample, the subject can be identified as not having pancreatic high-grade dysplasia (IPMN-HGD, PanIN-3, or PDAC), not being at risk for pancreatic high-grade dysplasia (IPMN-HGD, PanIN-3, or PDAC), or as having a low risk of pancreatic high-grade dysplasia (IPMN-HGD, PanIN-3, or PDAC). In this regard, subjects having pancreatic high-grade dysplasia (IPMN-HGD, PanIN-3, or PDAC) or risk thereof can be differentiated from subjects having low to substantially no pancreatic high-grade dysplasia (IPMN-HGD, PanIN-3, or PDAC) or risk thereof. Those subjects having a risk of developing pancreatic high-grade dysplasia (IPMN-HGD, PanIN-3, or PDAC) can be placed on a more intensive and/or regular screening schedule.

As mentioned above, depending on the embodiment of the method of the present technology, detecting a change in methylation state of the one or more biomarkers can be a qualitative determination or it can be a quantitative determination. As such, the step of diagnosing a subject as having, or at risk of developing, pancreatic high-grade dysplasia (IPMN-HGD, PanIN-3, or PDAC) indicates that certain threshold measurements are made, e.g., the methylation state of the one or more biomarkers in the biological sample varies from a predetermined control methylation state. In some embodiments of the method, the control methylation state is any detectable methylation state of the biomarker. In other embodiments of the method where a control sample is tested concurrently with the biological sample, the predetermined methylation state is the methylation state in the control sample. In other embodiments of the method, the predetermined methylation state is based upon and/or identified by a standard curve. In other embodiments of the method, the predetermined methylation state is a specifically state or range of state. As such, the predetermined methylation state can be chosen, within acceptable limits that will be apparent to those skilled in the art, based in part on the embodiment of the method being practiced and the desired specificity, etc.

Further with respect to diagnostic methods, a preferred subject is a vertebrate subject. A preferred vertebrate is warm-blooded; a preferred warm-blooded vertebrate is a mammal. A preferred mammal is most preferably a human. As used herein, the term "subject' includes both human and animal subjects. Thus, veterinary therapeutic uses are provided herein. As such, the present technology provides for the diagnosis of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the diagnosis and treatment of livestock, including, but not limited to, domesticated swine, ruminants, ungulates, horses (including race horses), and the like. The presently-disclosed subject matter further includes a system for diagnosing pancreatic high-grade dysplasia (IPMN-HGD, PanIN-3, or PDAC) in a subject. The system can be provided, for example, as a commercial kit that can be used to screen for a risk of such a disorder in a subject from whom a biological sample has been collected. An exemplary system provided in accordance with the present technology includes assessing the methylation state of a DMR as provided in Tables 2 and 6.

EXAMPLES

Example I

Intraductal papillary mucinous neoplasm (IPMN) and pancreatic intraepithelial neoplasia (PanIN) are the key ductal precursors of pancreatic ductal adenocarcinoma (PDAC). While there is consensus that precursor lesions having high-grade dysplasia (HGD) and early PDAC should be treated surgically, current imaging tools and risk prediction models are imperfect and often fail to detect such lesions. Discriminant molecular markers, applied to media such as pancreatic juice, pancreatic cyst fluid, or stool, are needed to more accurately detect high-risk lesions.

Experiments were conducted to identify and validate methylated DNA marker candidates that discriminate a case group with high-grade precursors (IPMN-HGD, PanIN-3) or invasive cancer (PDAC) from a control group with either normal pancreas or low-grade precursor lesions (IPMN-low grade dysplasia (IPMN-LGD), PanIN-1, and PanIN-2).

Identification of candidate markers was based on an unbiased whole methylome discovery approach using reduced representation bisulfite sequencing (RRBS) on DNA from frozen pancreatic normal and neoplastic tissues; candidate markers were selected based on area under the ROC curve (AUC), fold-change, and p-value. Validation was based on independent micro-dissected tissues from case and control groups and blinded assay of selected markers using methylation specific PCR; marker levels were standardized to methylated LRRC4, a marker for pancreatic epithelia. Case group (n=53) included IPMN-HGD (19), PanIN-3 (4), and PDAC (30). Control group (n=111) included histologically-normal pancreatic tissue (31), IPMN-LGD (36), PanIN-1 (34), and PanIN-2 (10). AUC was calculated for each marker by logistic regression, and discrimination by marker combinations was explored.

From RRBS data, 28 candidate markers were selected for MSP validation. Three of these were Z-markers, a term used to identify regions which exhibit CpG hypermethylation in all the tissue samples whether normal, dysplastic, or cancerous—but have little to no methylation in hematopoietic derived DNA, such as circulating leukocytes (see, for example, Ser. No. 14/966,938). Z-markers serve 2 important functions—they are an effective denominator when normalizing neoplastic markers to a total epithelial signal in a biological sample (which usually contains some degree of immunologic infiltration) and they can be tumor specific markers in their own right in those cases where tumor cell shedding, apoptosis, or necrosis causes normal cells/DNA to be released as well.

Twenty three markers had MSP AUC values≥0.8 and p-values≤0.01 in the discovery samples and were taken, along with the 3 Z-markers, into an expanded independent validation set as outlined in the methods (Example III). Universal methylation standards were used in the assays, along with appropriate negative controls. Results were expressed as % methylation (normalized to LRRC4, a marker for pancreatic tissue). 4 markers were eliminated (low AUC (<0.79), low % methylation in cases, or high background) leaving 19 promising candidates (ABCB1, AK055957, C13ORF18, CD1D, CLEC11A, DLX4, ELMO1, EMX1, FER1L4, FRMD4A, GRIN2D, HOXA1, PRKCB, SP9, ST6GAL2, ST8SIA1, TBX15, VWC2, and ZNF781).

Discrimination between case and control groups was established in the validation set, and markers with AUC values≥0.79 on validation are listed at Table 1A (providing AUC values for the 19 promising candidates—ABCB1, AK055957, C13ORF18, CD1D, CLEC11A, DLX4, ELMO1, EMX1, FER1L4, FRMD4A, GRIN2D, HOXA1, PRKCB, SP9, ST6GAL2, ST8SIA1, TBX15, VWC2, and ZNF781). Table 1B shows a panel of markers with AUC values≥0.85. The panel shown at Table 1B detected 89, 87, 77, and 74% of cases at respective specificities of 85, 90, 95, and 100%.

Figure 1B:
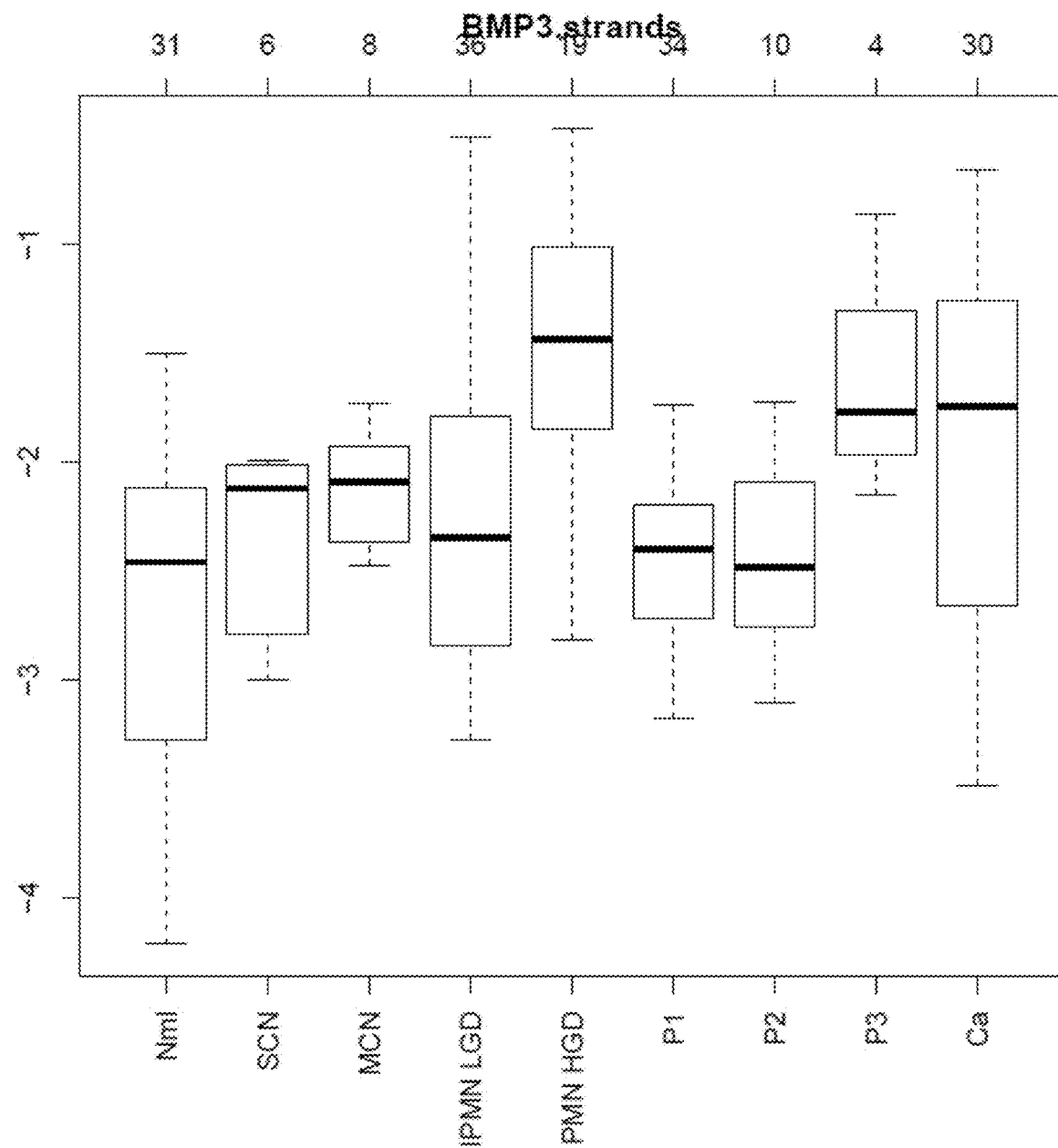
Figure 1C:
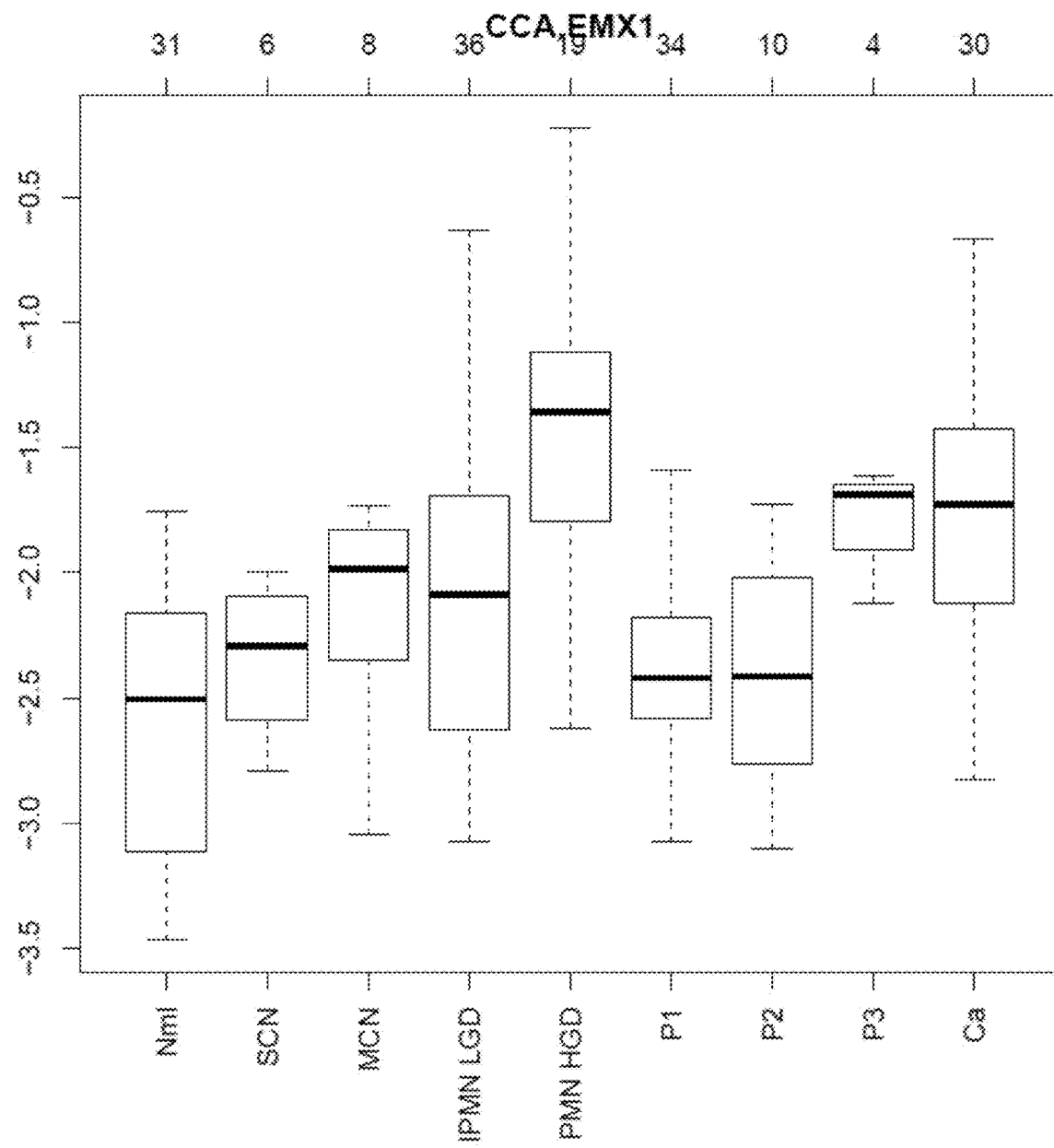
Figure 1D:
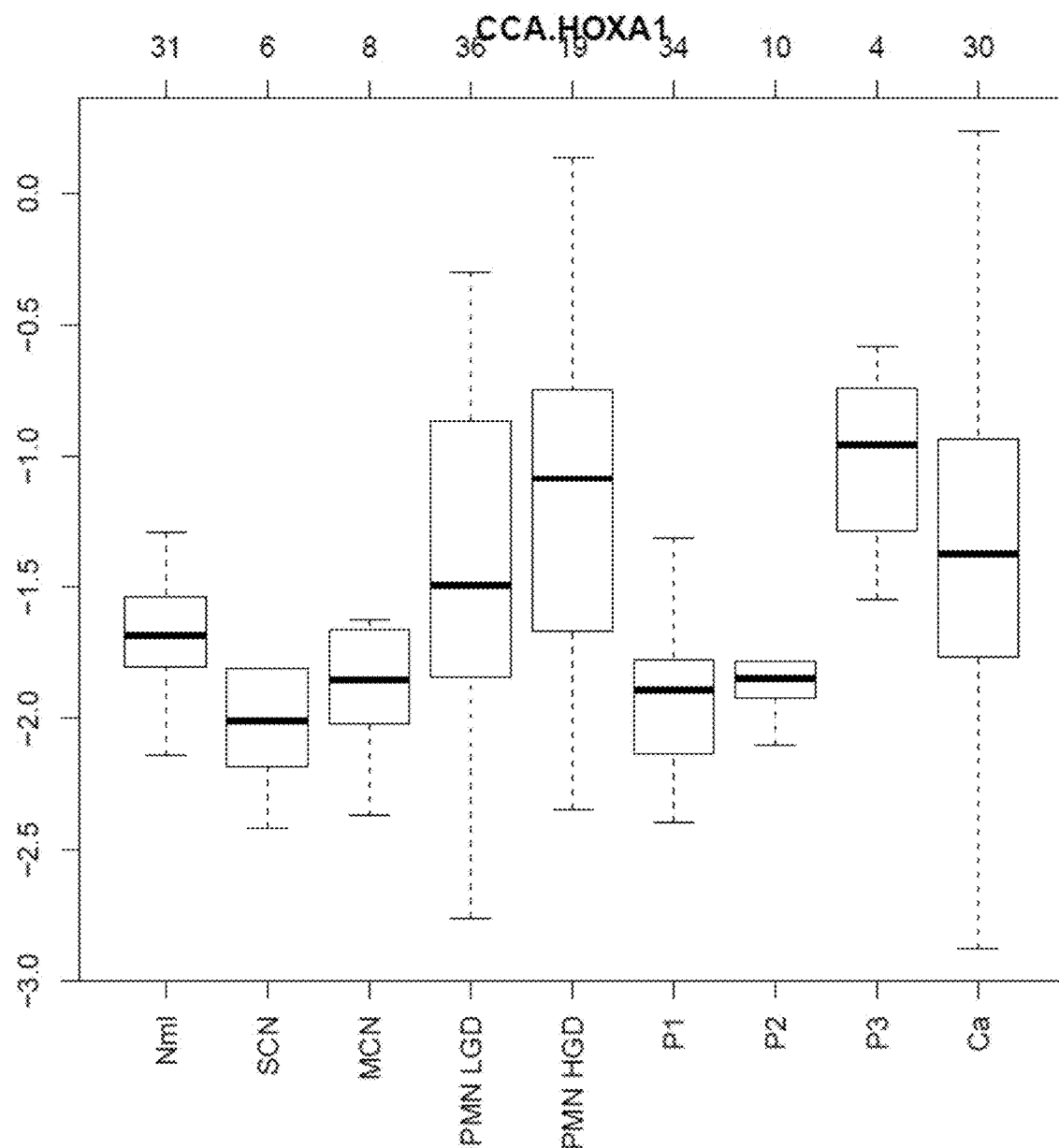
Figure 1E:
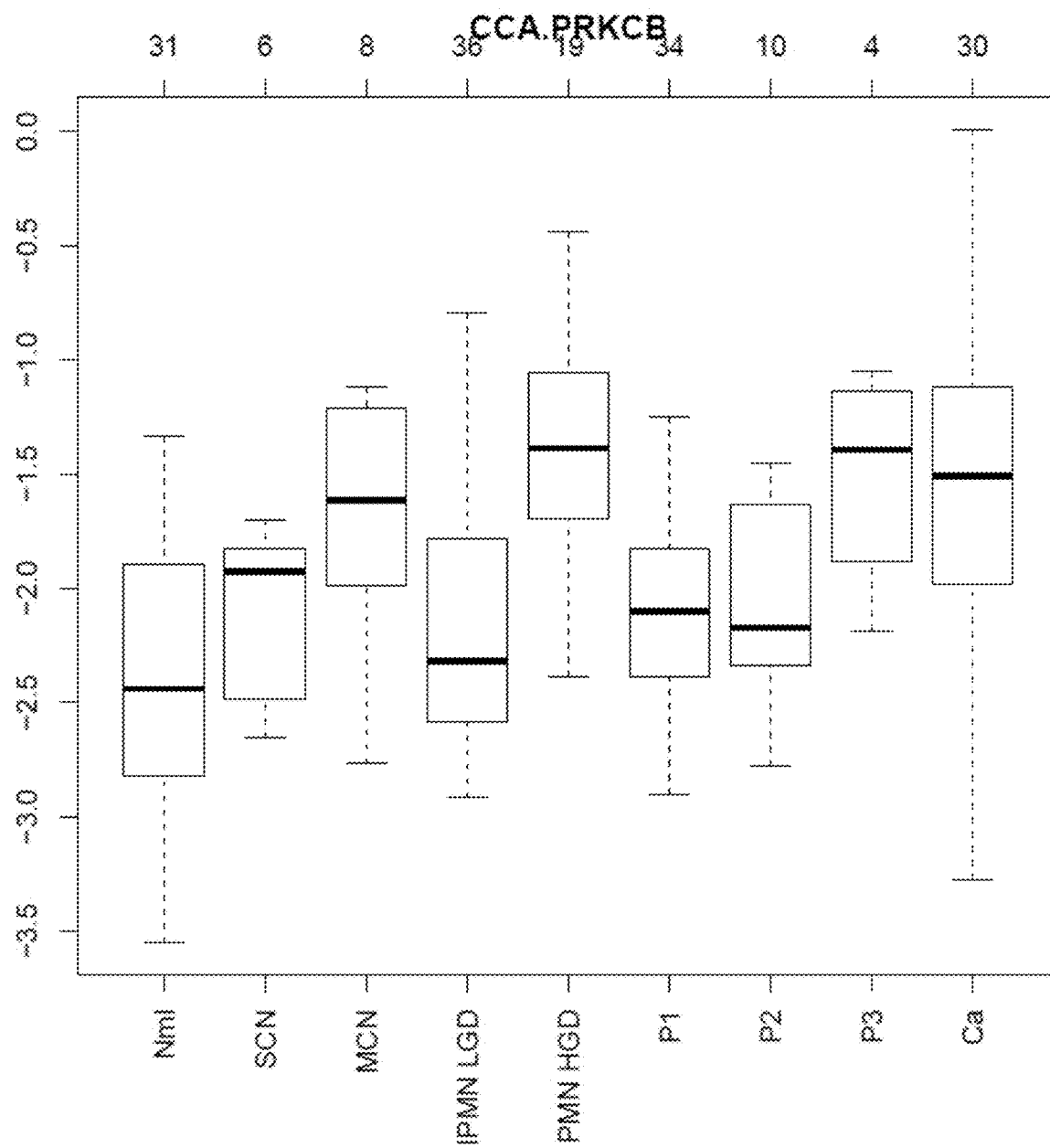
Figure 1F:
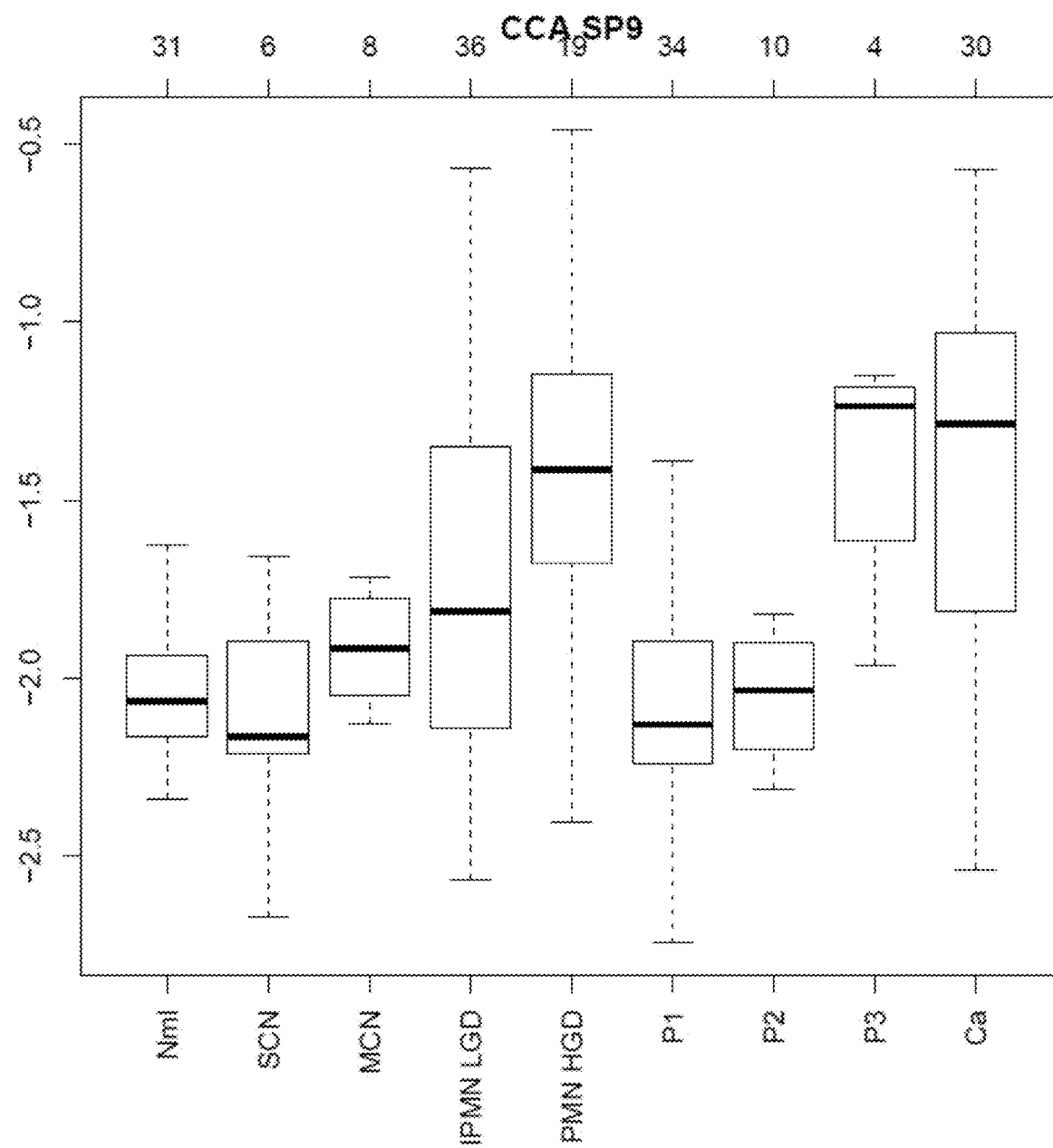
Figure 1G:
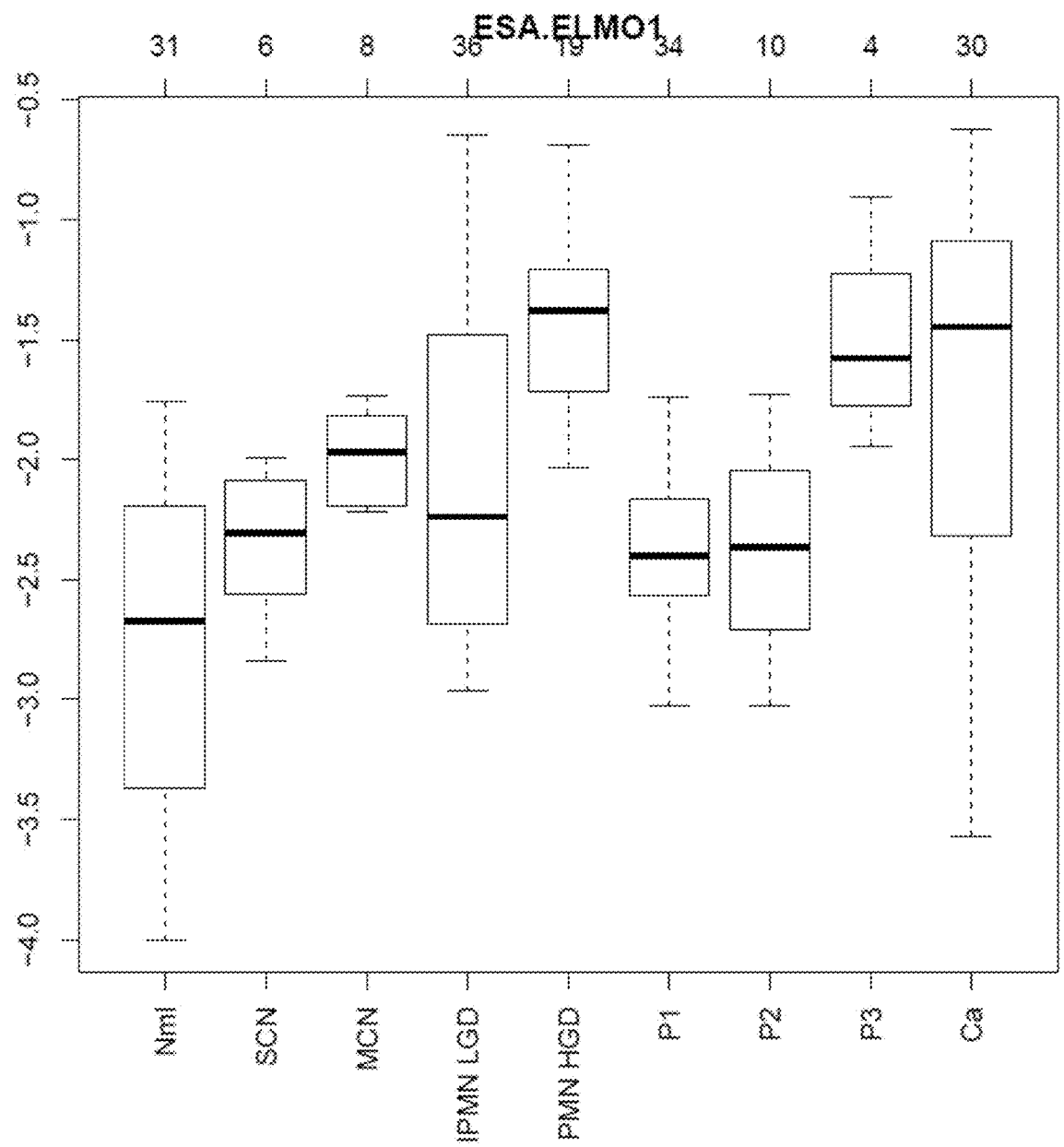
Figure 1H:
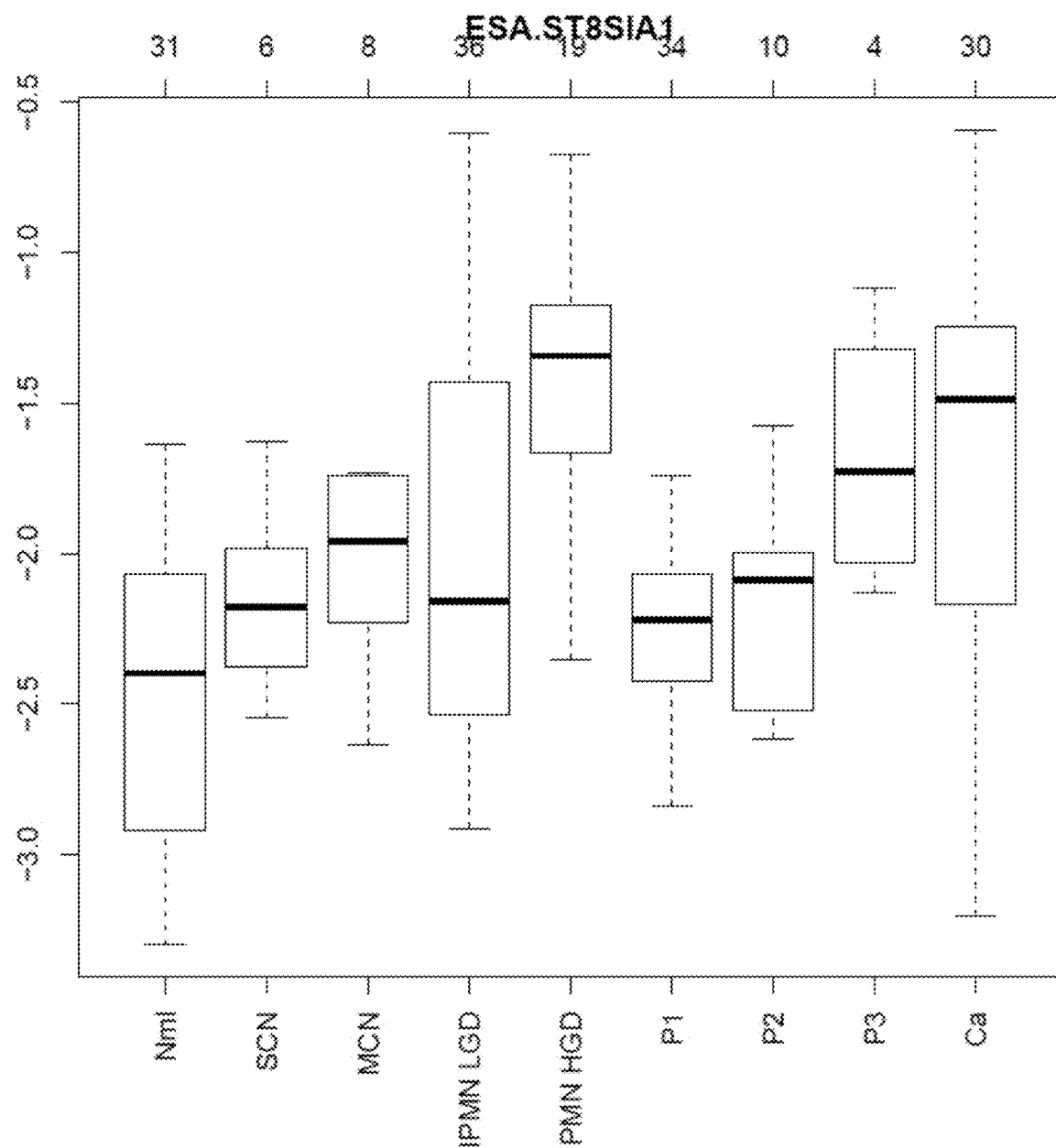
Figure 1I:
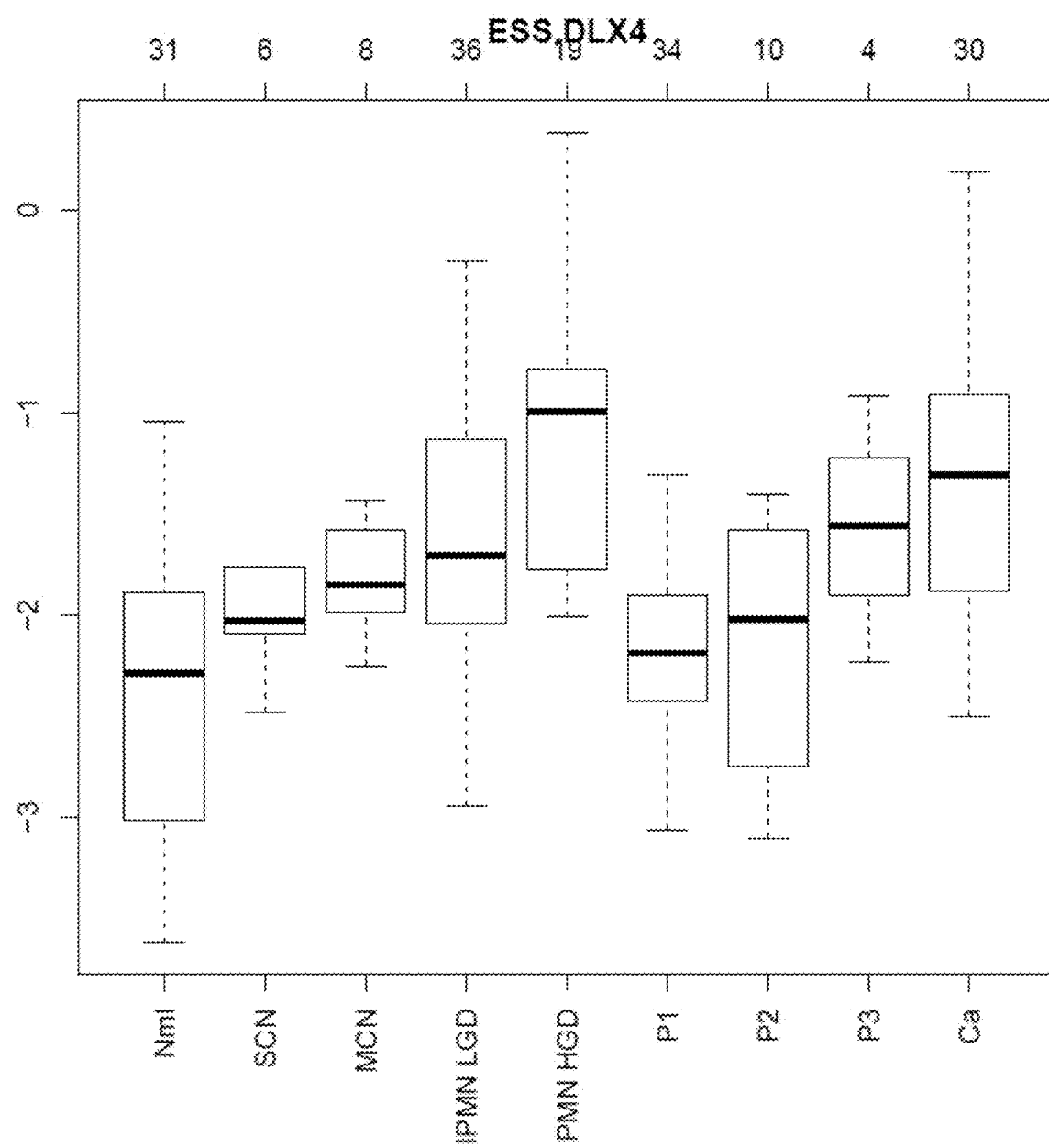
Figure 1J:
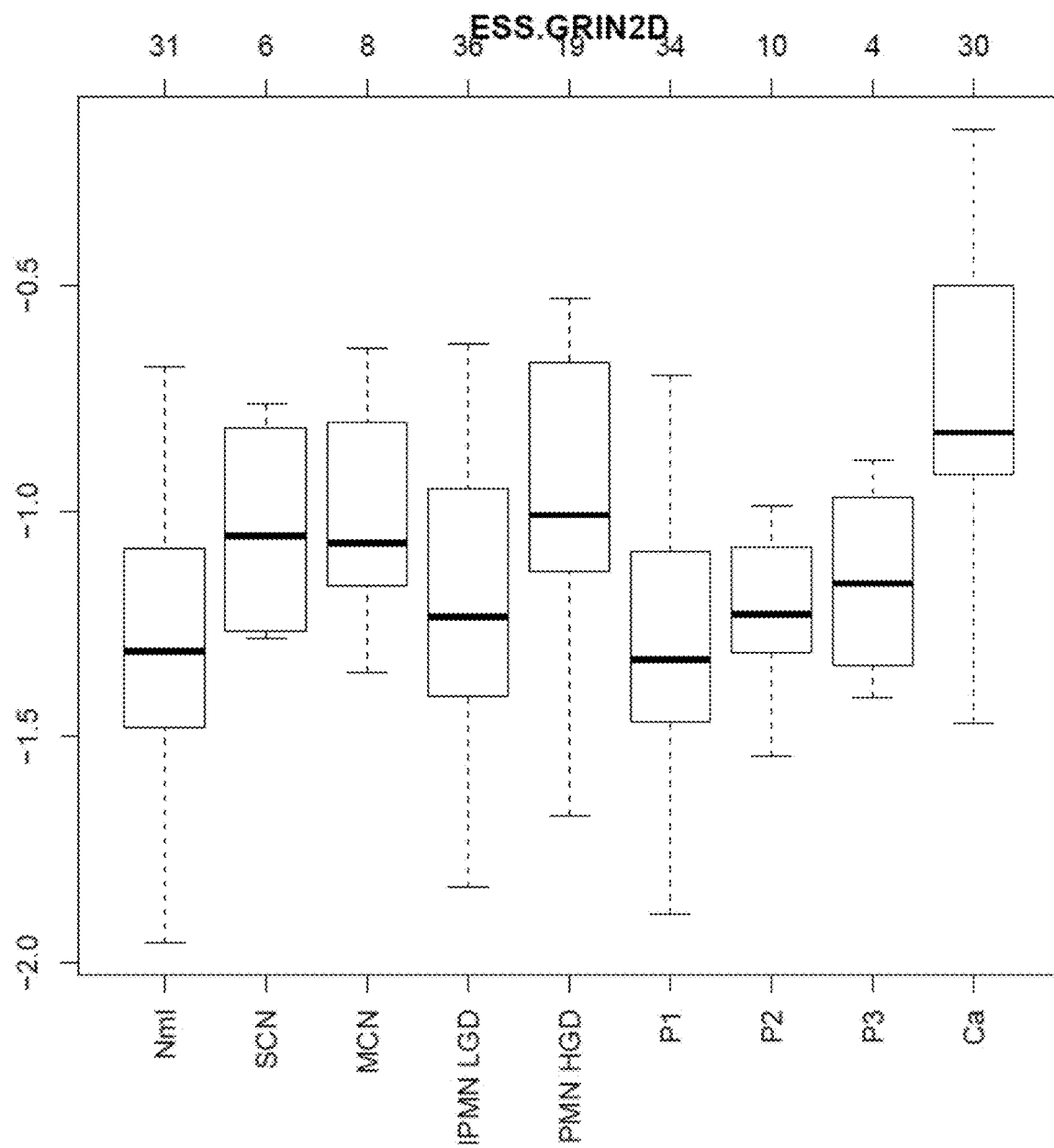
Figure 1K:
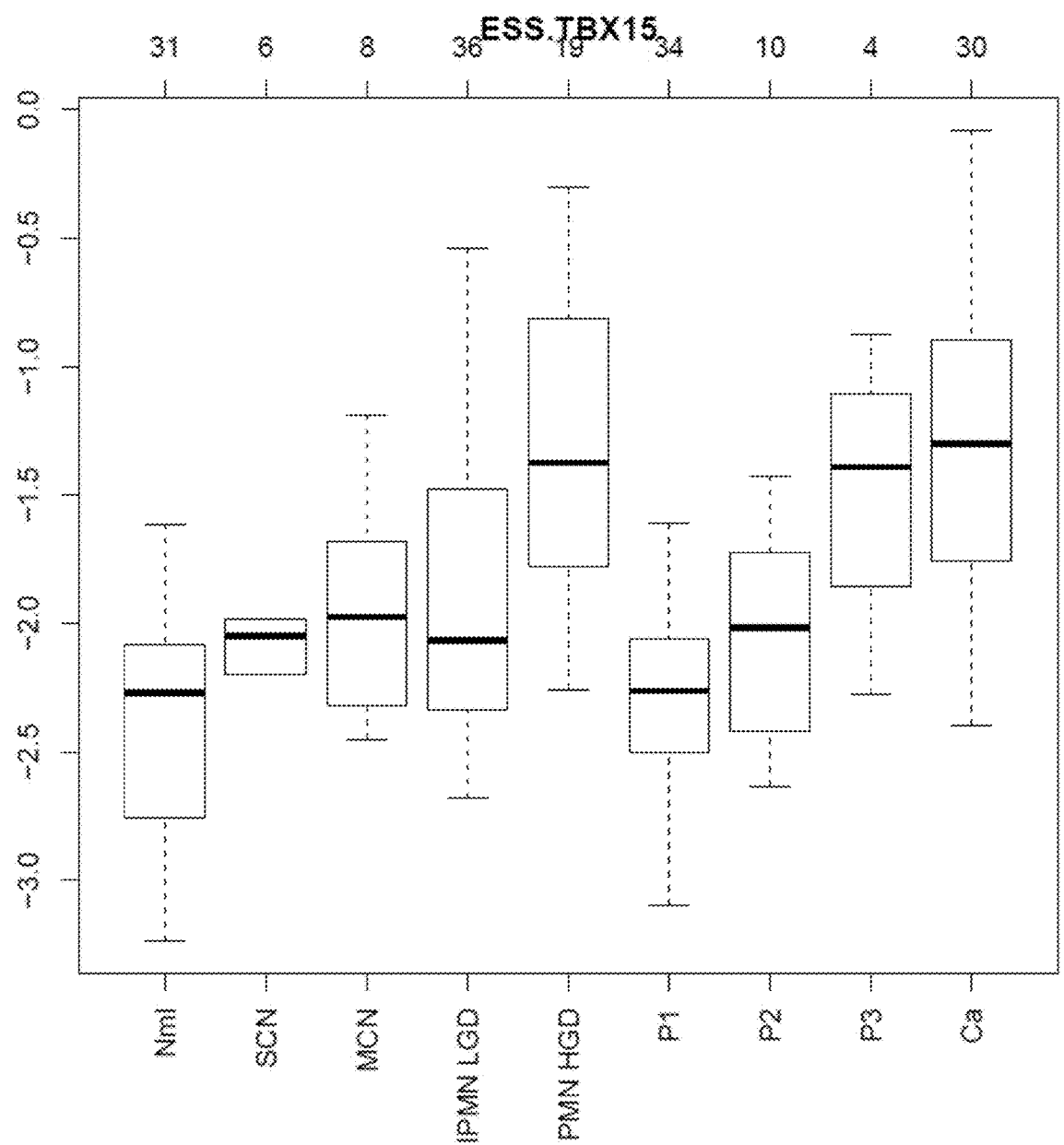
Figure 1L:
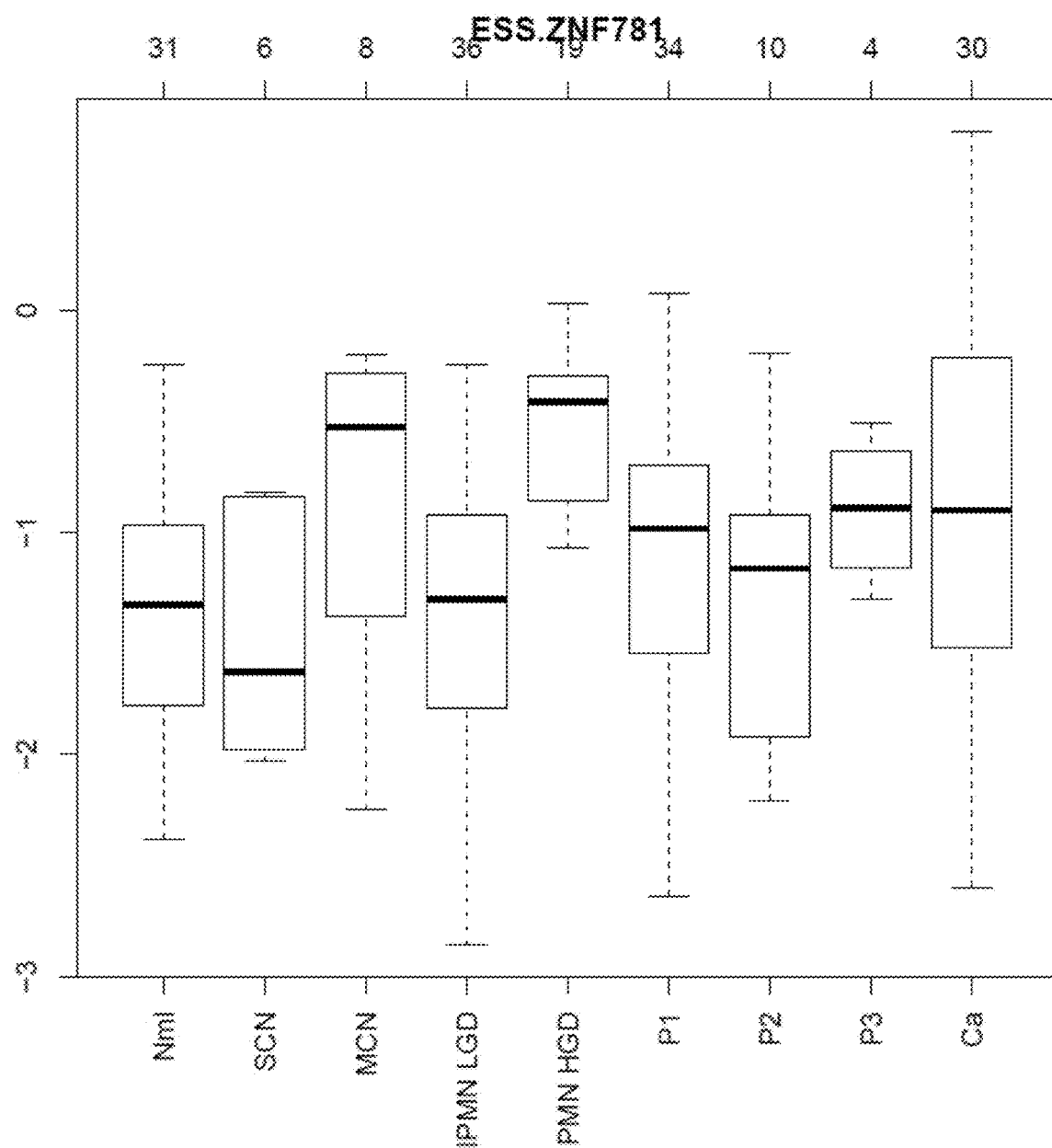
Figure 1M:
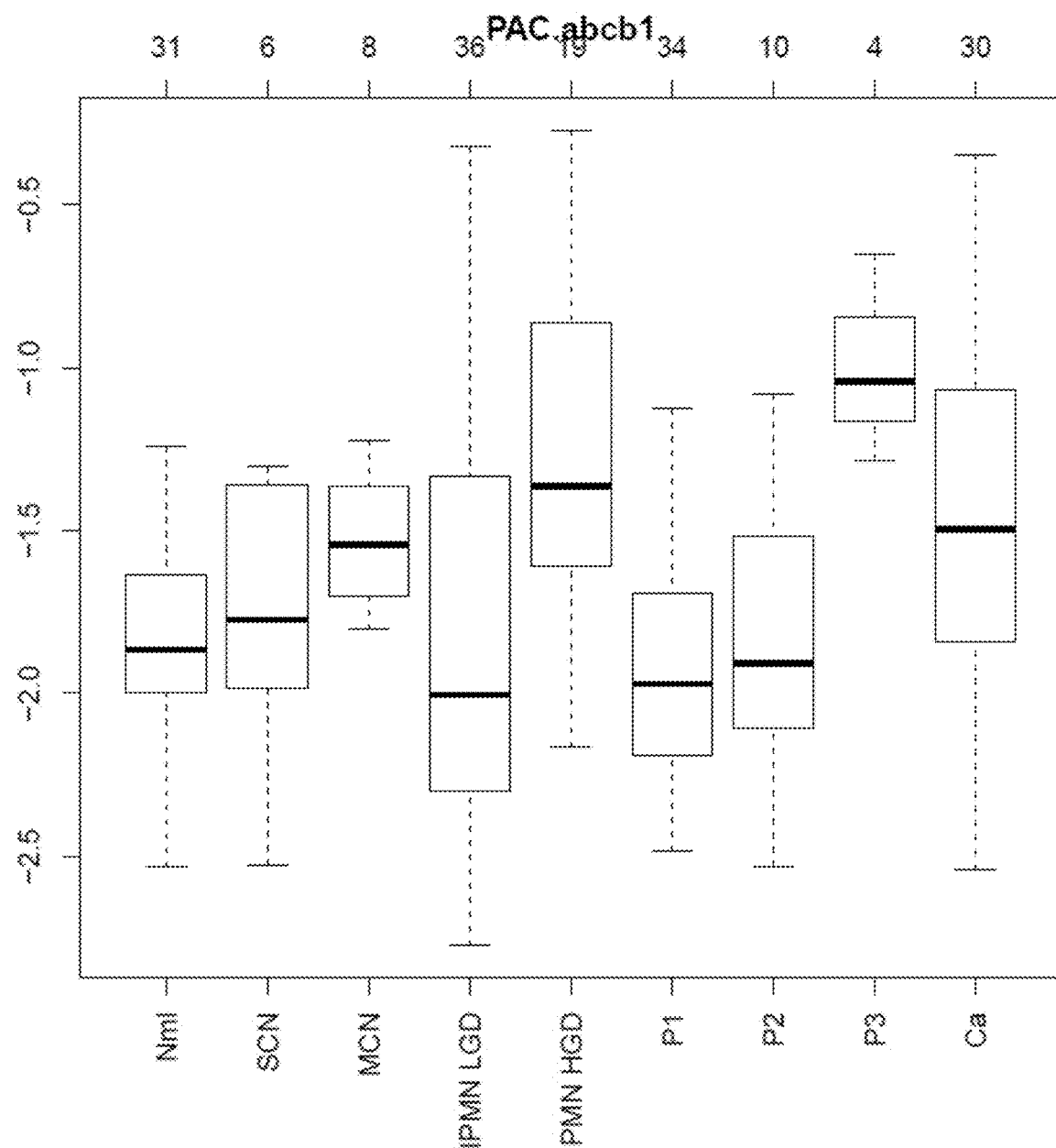
Figure 1N:
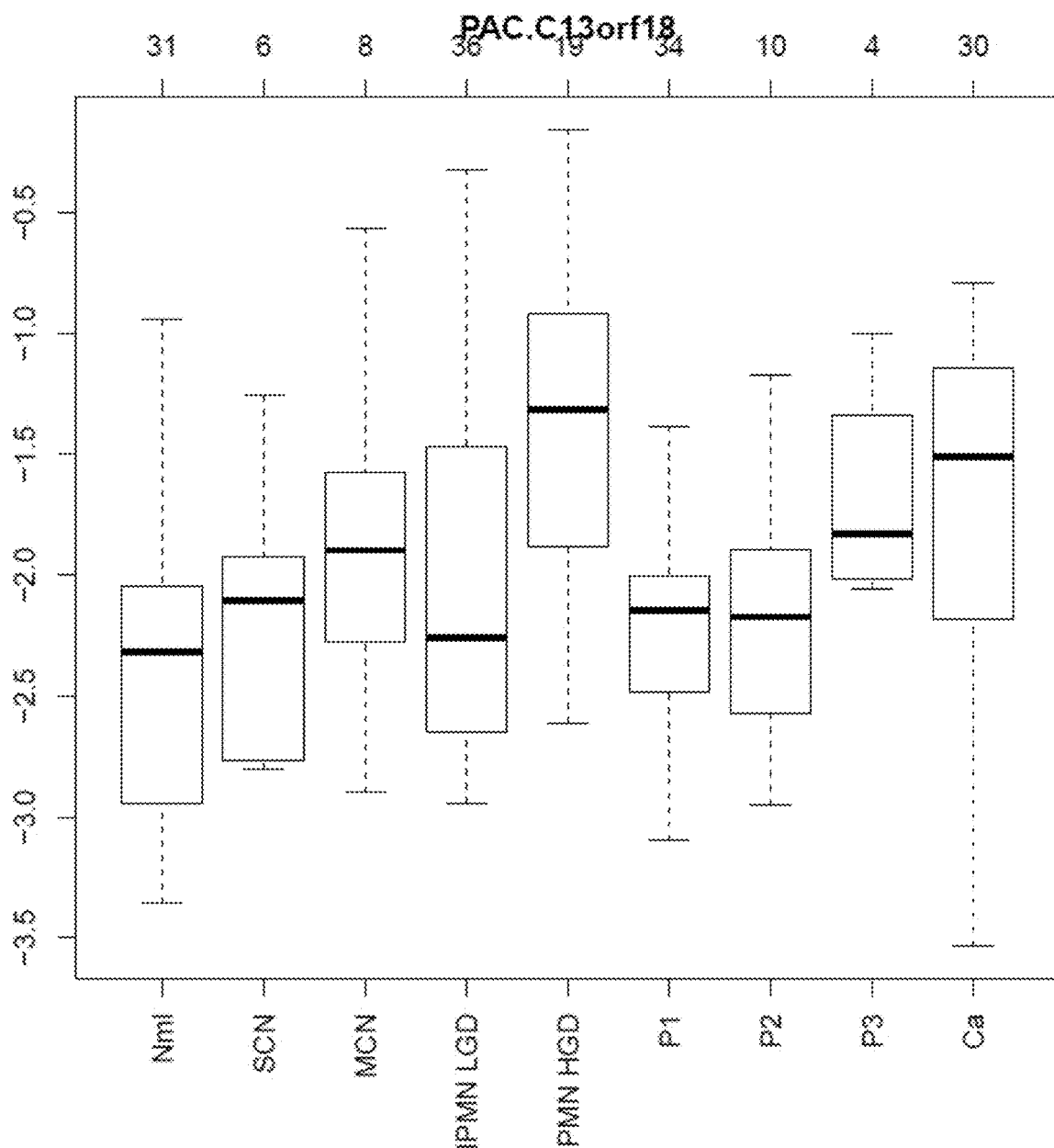
Figure 1O:
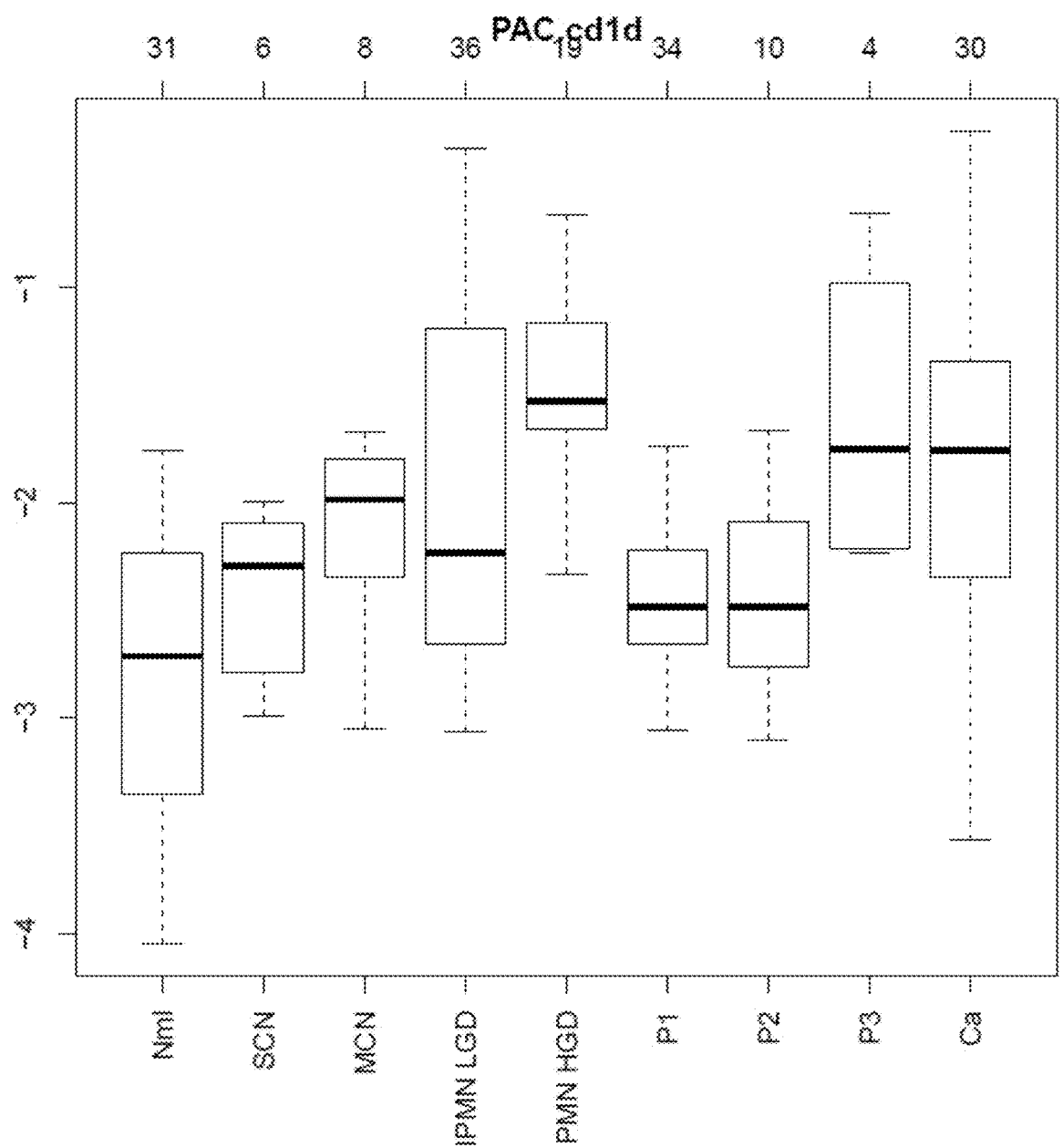
Figure 1P:
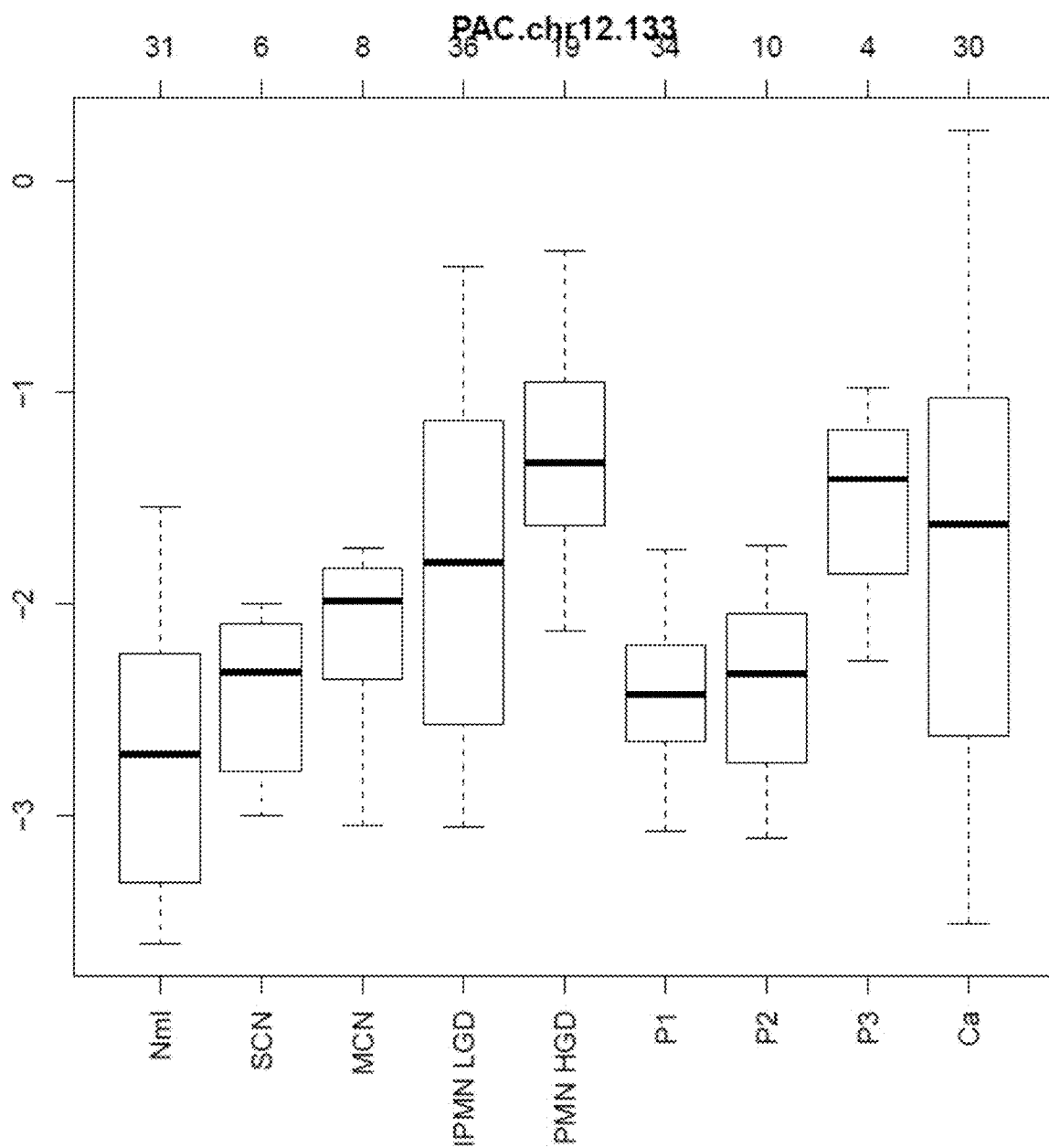
Figure 1Q:
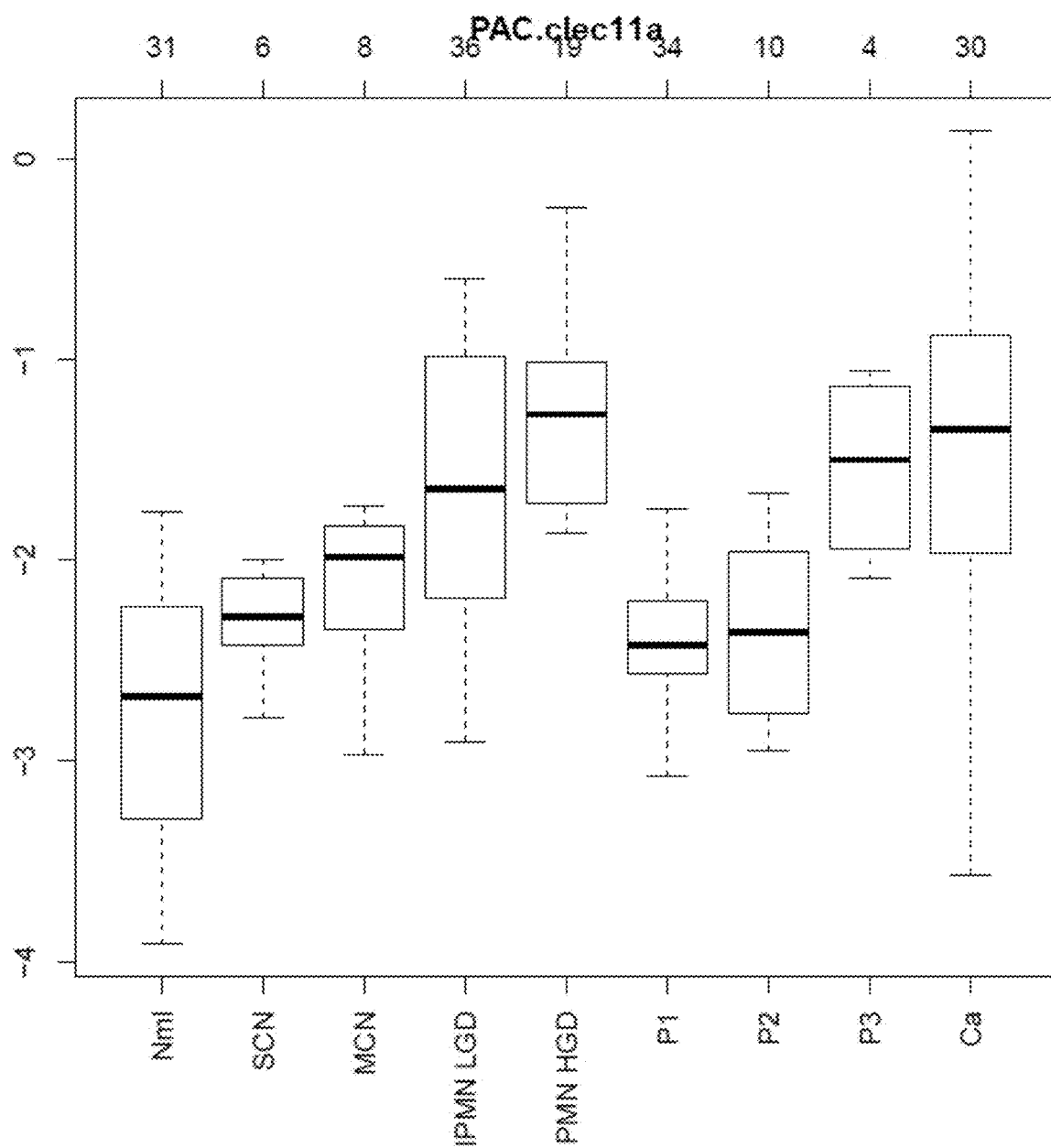
Figure 1R:
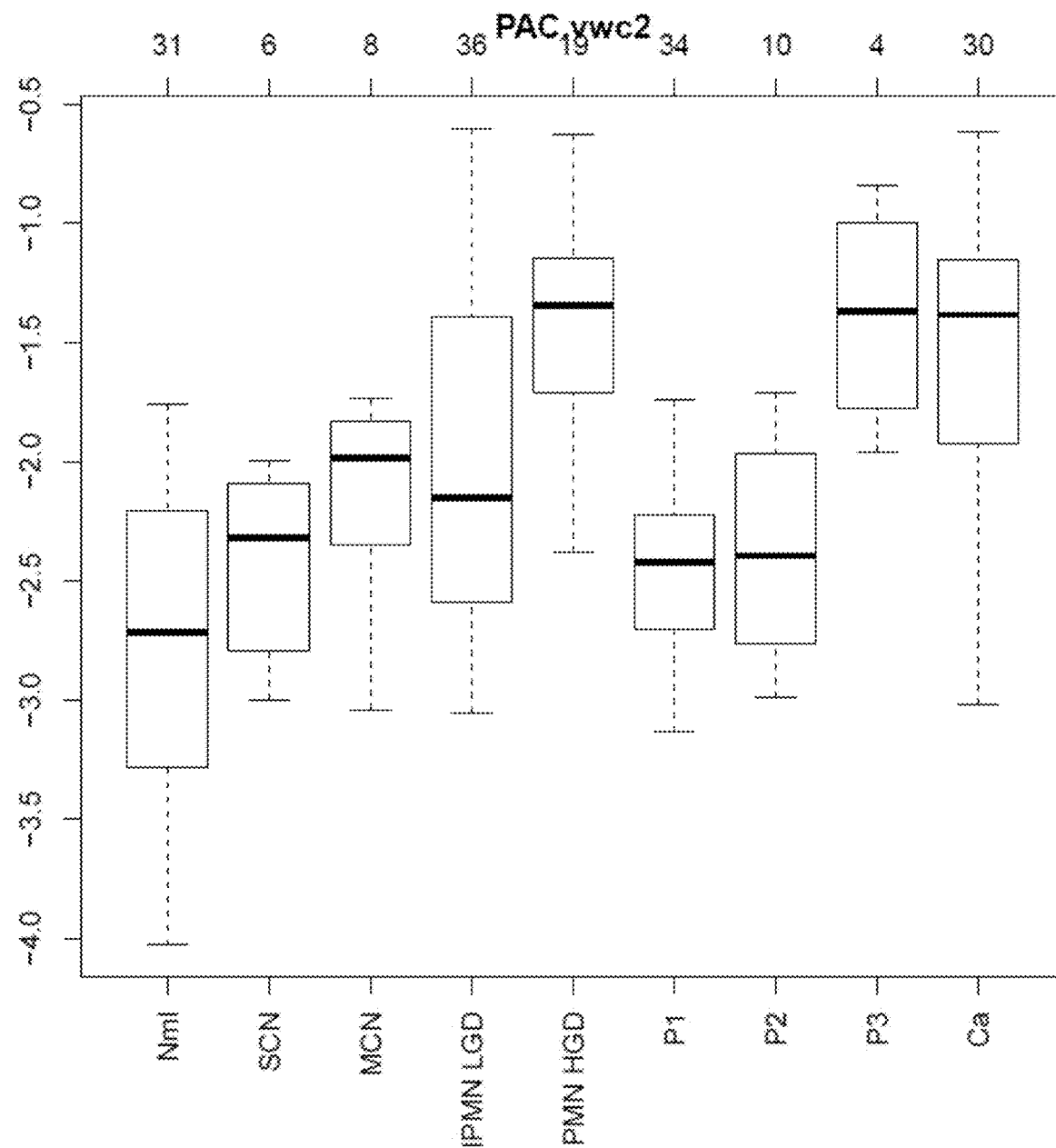
Figure 1S:
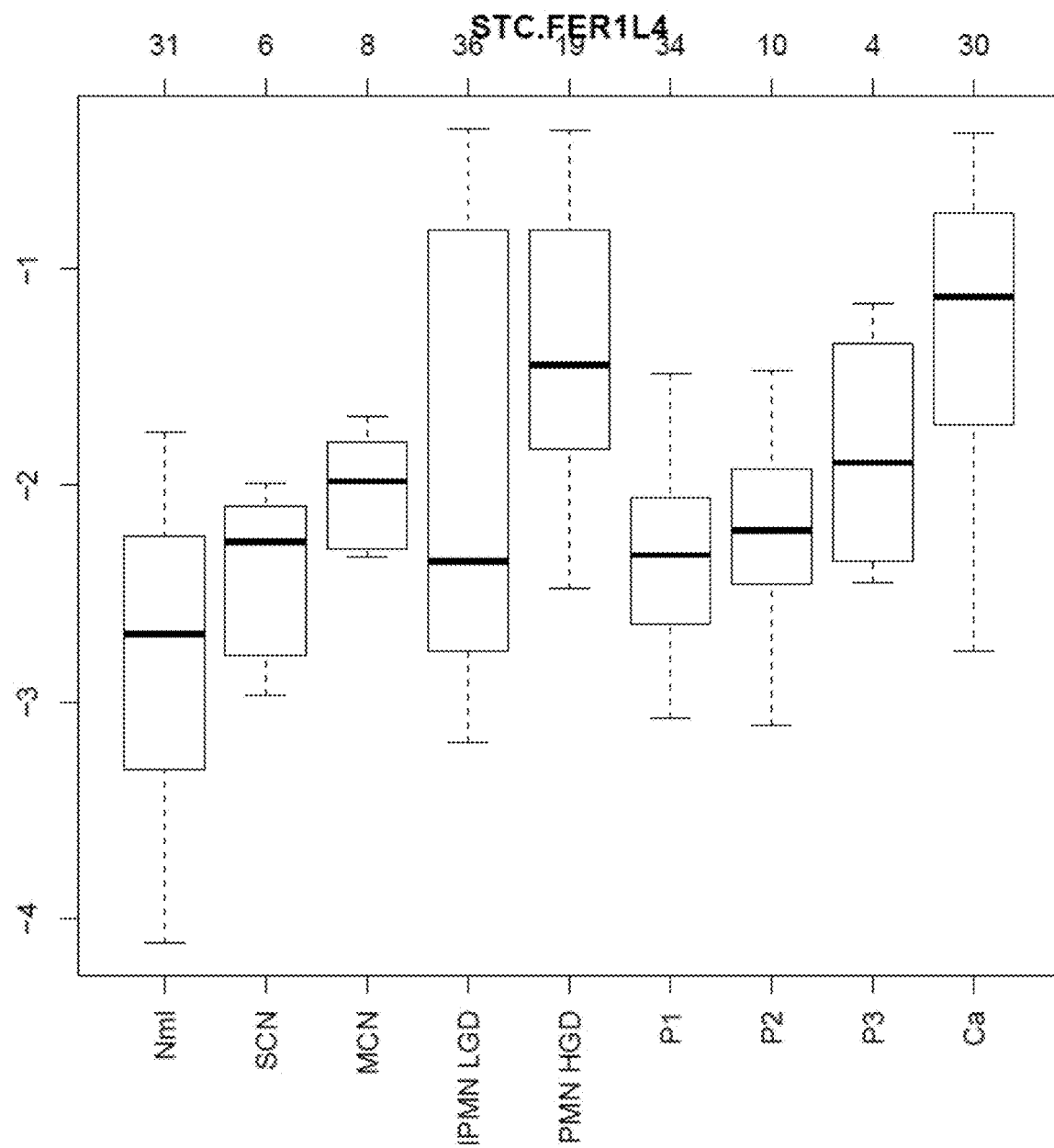
Figure 1T:
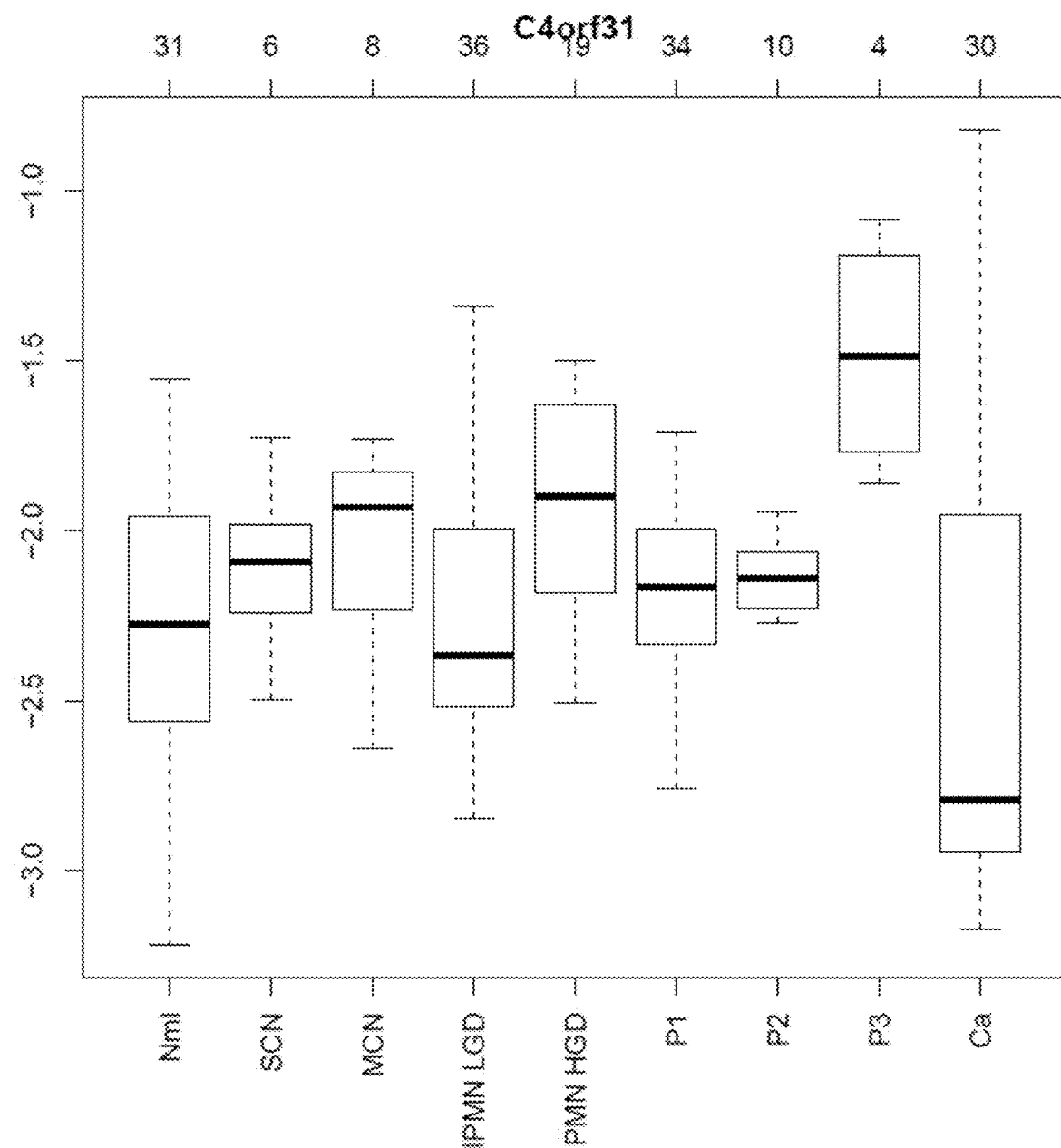
Figure 1U:
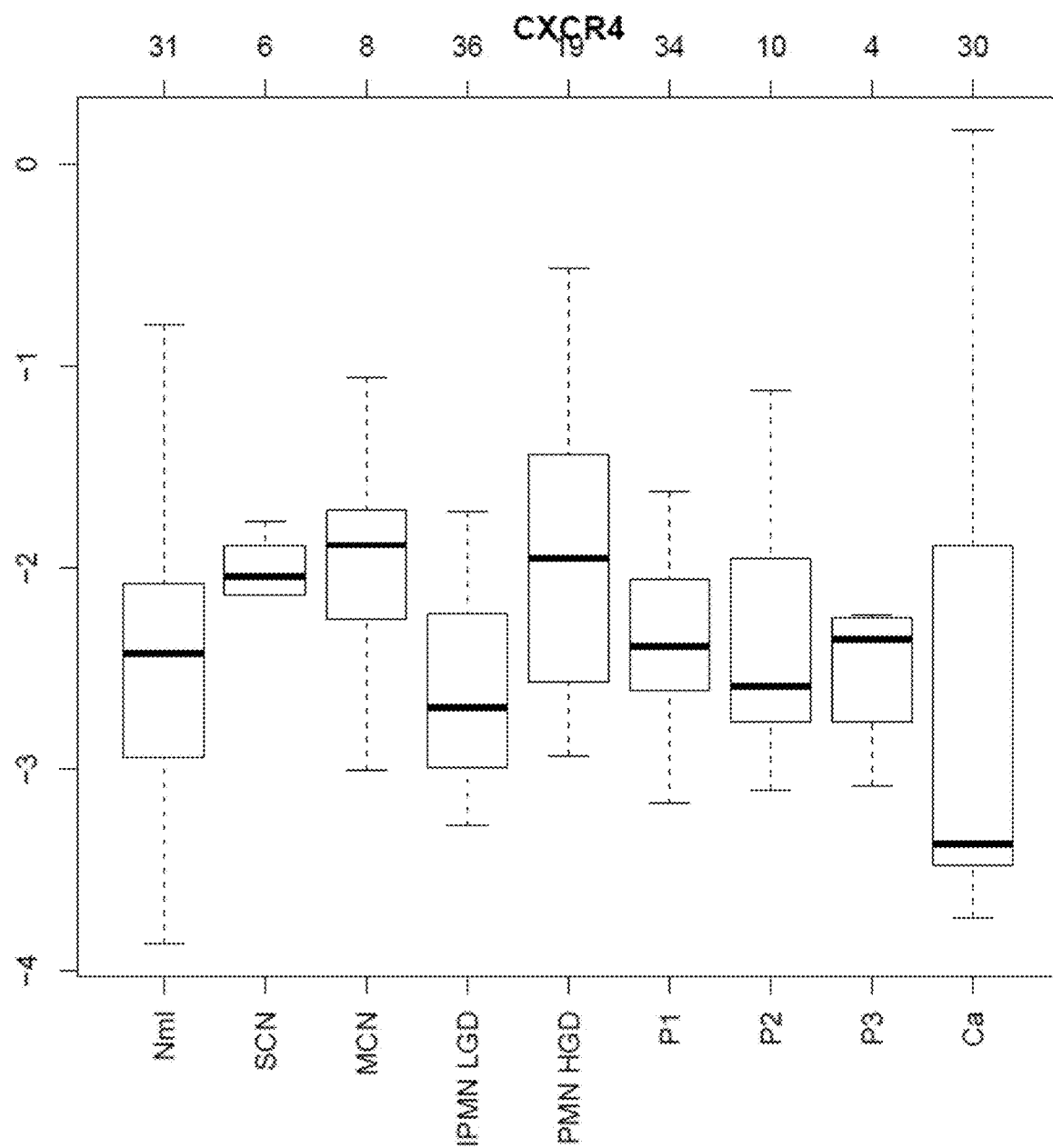
Figure 1V:
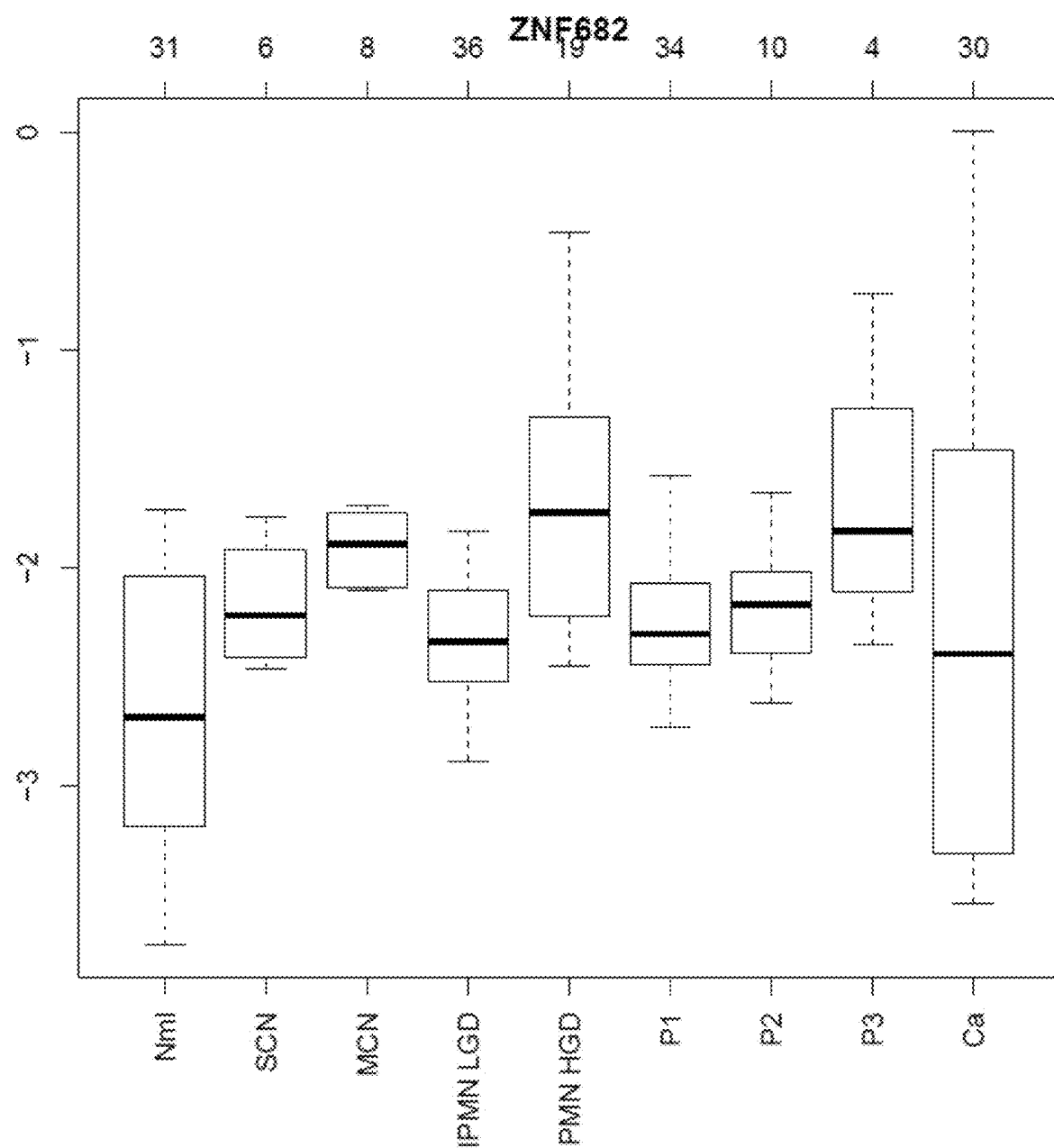
Figure 1W:
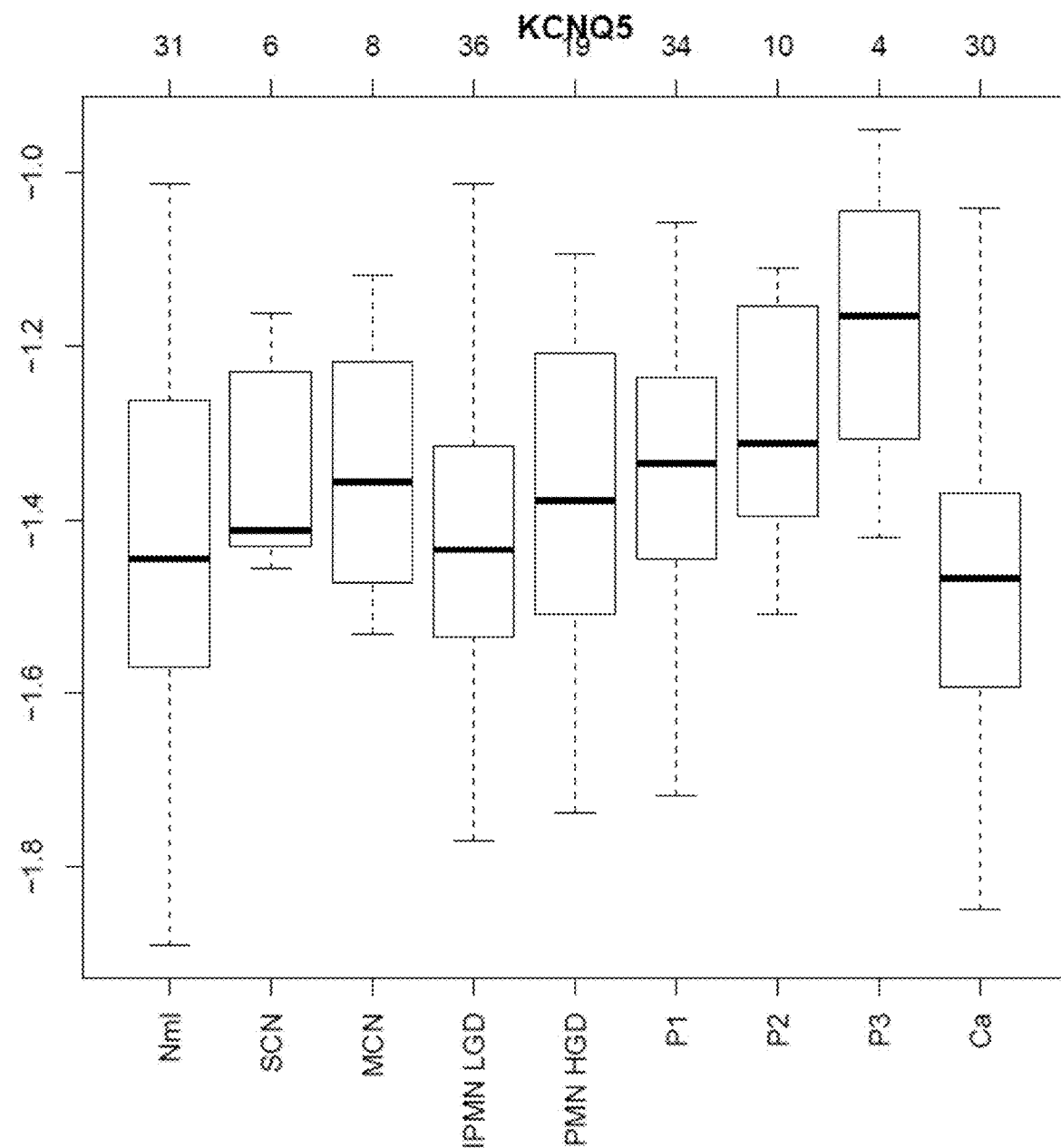
Figure 1X:
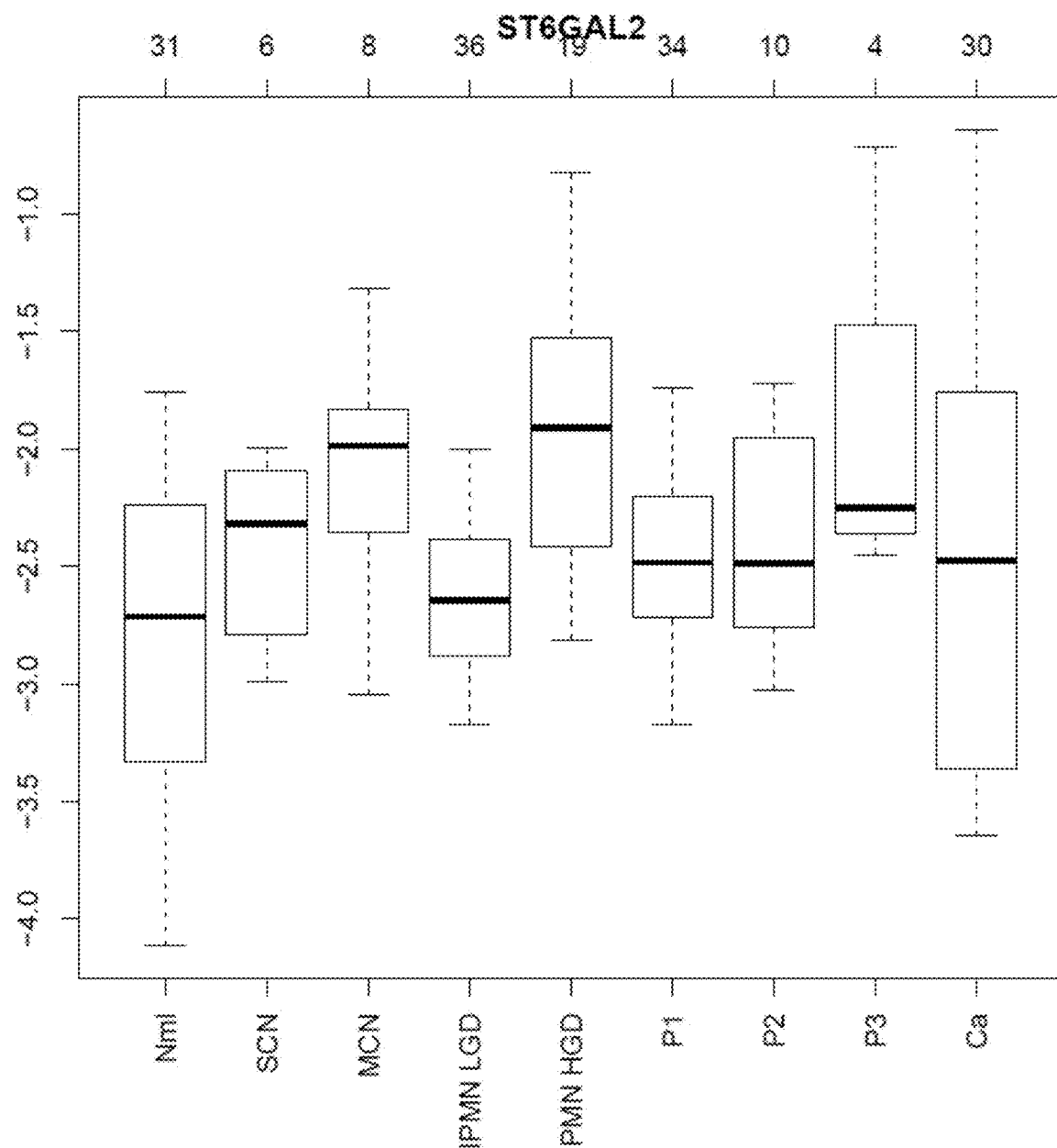

FIG. 1 provides distribution plots of different markers assayed from pancreatic tissue. A distribution plot of one top marker (TBX15) across individual tissue categories illustrates clearly the much higher levels in cases (IPMN-HGD, PanIN-3, and PDAC) than controls (FIG. 1). A panel of top markers yielded an AUC of 0.91 (95% CI: 85-96%). The panel detected 89, 87, 77, and 74% of cases at respective specificities of 85, 90, 95, and 100%.

Table 2 provides DMR information including chromosome number, gene annotation, and DMR start/stop position for such markers identified as highly discriminant markers for high-grade precursors (IPMN-HGD, PanIN-3) or invasive cancer (PDAC) (including ABCB1, AK055957, C13ORF18, CD1D, CLEC11A, DLX4, ELMO1, EMX1, FER1L4, FRMD4A, GRIN2D, HOXA1, PRKCB, SP9, ST6GAL2, ST8SIA1, TBX15, VWC2, and ZNF781). Table 3 provides primers for the DMRs provided in Table 2.

TABLE 1A

| Marker | AUC |
|---|---|
| VWC2 | 0.89 |
| TBX15 | 0.89 |
| CLEC11A | 0.89 |
| PRKCB | 0.89 |
| EMX1 | 0.88 |
| ELMO1 | 0.88 |
| ST8SIA1 | 0.87 |
| ABCB1 | 0.87 |
| DLX4 | 0.87 |
| SP9 | 0.86 |
| FRMD4A | 0.85 |
| GRIN2D | 0.85 |
| FER1L4 | 0.84 |
| CD1D | 0.83 |
| HOXA1 | 0.83 |
| AK055957 | 0.82 |
| C13orf18 | 0.82 |
| ZNF781 | 0.81 |
| ST6GAL2 | 0.79 |

TABLE 1B

Selected methylated DNA markers with high discrimination (AUC > 0.85) between cases (IPMN-HGD, PanIN-3, PDAC) and controls (Normal, IPMN-LGD, PanIN-1, 2)

| Marker | AUC | 95% Confidence Interval | p |
|---|---|---|---|
| TBX15 | 0.89 | 0.83-0.95 | <0.001 |
| VWC2 | 0.89 | 0.83-0.95 | <0.001 |
| PRKCB | 0.89 | 0.83-0.95 | <0.001 |
| CLEC11A | 0.89 | 0.83-0.94 | <0.001 |
| EMX1 | 0.88 | 0.82-0.94 | <0.001 |
| ELMO1 | 0.88 | 0.81-0.94 | <0.001 |
| DLX4 | 0.87 | 0.81-0.92 | <0.001 |
| ABCB1 | 0.87 | 0.80-0.93 | <0.001 |
| ST8SIA1 | 0.87 | 0.80-0.93 | <0.001 |
| SP9 | 0.86 | 0.79-0.92 | <0.001 |

TABLE 2

Information for DMRs

| DMR No. | Gene Annotation | Chromosome No. | DMR Start-End Positions |
|---|---|---|---|
| 1 | ABCB1 | 7 | 87229775-87229856 |
| 2 | ACAN | 15 | 89346282-89346382 |
| 3 | ADAM23 | 2 | 207308771-207308844 |
| 4 | AJAP1 | 1 | 4714768-4714799 |
| 5 | AK055957 | 12 | 133484978-133485739 |
| 6 | ANKS1B | 12 | 99288410-99288435 |
| 7 | ANKS1B | 12 | 99288269-99288361 |
| 8 | ARHGEF4 | 2 | 131797843-131797938 |
| 9 | ASCL1 | 12 | 103352254-103352327 |
| 10 | BEND4 | 4 | 42153551-42153626 |
| 11 | BTBD11 | 12 | 107713354-107713454 |
| 12 | C13orf18 | 13 | 46960767-46961669 |
| 13 | C8orf42 | 8 | 495602-495648 |
| 14 | CACNB2 | 10 | 18429175-18429297 |
| 15 | CADM3 | 1 | 159141662-159141748 |
| 16 | CADM3 | 1 | 159158449-159158481 |
| 17 | CCNA1 | 13 | 37005929-37005955 |
| 18 | CD1D | 1 | 158150797-158151205 |
| 19 | CELF2 | 10 | 11059508-11059637 |
| 20 | CELF2 | 10 | 11059947-11060085 |
| 21 | CLEC11A | 19 | 51228217-51228732 |
| 22 | COL23A1 | 5 | 178017202-178017291 |
| 23 | DAB1 | 1 | 58715853-58715890 |
| 24 | DLX4 | 17 | 48042426-48042820 |
| 25 | ELMO1 | 7 | 37487755-37488477 |
| 26 | EMX1 | 2 | 73147710-73147772 |
| 27 | EYA4 | 6 | 133562302-133562380 |
| 28 | FBLN1 | 22 | 45898783-45898862 |
| 29 | FBLN1 | 22 | 45898874-45898984 |
| 30 | FER1L4 | 20 | 34189488-34189566 |
| 31 | FJX1 | 11 | 35640997-35641094 |
| 32 | FJX1 | 11 | 35641325-35641485 |
| 33 | FLI1 | 11 | 128564620-128564788 |
| 34 | FLT1 | 13 | 29068359-29068403 |
| 35 | FRMD4A | 10 | 13933742-13933802 |
| 36 | FRMD4A | 10 | 13933653-13933799 |
| 37 | GAD2 | 10 | 26505523-26505589 |
| 38 | GALNT13 | 2 | 154728133-154728196 |
| 39 | GDNF | 5 | 37839926-37840050 |
| 40 | GFPT2 | 5 | 179780663-179781008 |
| 41 | GRIN2D | 7 | 37487755-37488477 |
| 42 | HMX3 | 10 | 124895177-124895244 |
| 43 | HOXA1 | 7 | 27136145-27136425 |
| 44 | ILDR2 | 1 | 166916866-166917004 |
| 45 | ISLR2 | 15 | 74420532-74420572 |
| 46 | KCNA1 | 12 | 5019401-5019496 |
| 47 | KCNA1 | 12 | 5019741-5019848 |
| 48 | KCNA1 | 12 | 5019499-5019633 |
| 49 | KIAA1239 | 4 | 37246813-37246866 |
| 50 | KIAA1239 | 4 | 37245707-37245735 |
| 51 | KIF19 | 17 | 72322322-72322421 |
| 52 | LOC100130155 | 8 | 65282172-65282334 |
| 53 | LOC100192379 | 4 | 122686300-122686394 |
| 54 | LOC642345 | 13 | 88324257-88324286 |
| 55 | LRRC4 | 7 | 127671993-127672310 |
| 56 | LY6H | 8 | 144241567-144241620 |
| 57 | MAX.chr12.133484966-133485681 | 12 | 133484966-133485681 |
| 58 | MAX.chr2.137523242-137523296 | 2 | 137523242-137523296 |

TABLE 2-continued

Information for DMRs

| DMR No. | Gene Annotation | Chromosome No. | DMR Start-End Positions |
|---|---|---|---|
| 59 | MAX.chr2.468116-468180 | 2 | 468116-468180 |
| 60 | MAX.chr3.69591901-69591966 | 3 | 69591901-69591966 |
| 61 | MAX.chr4.8859999-8860038 | 4 | 8859999-8860038 |
| 62 | MAX.chr8.72459953-72459992 | 8 | 72459953-72459992 |
| 63 | NEFL | 8 | 24813584-24813624 |
| 64 | NEFL | 8 | 24814127-24814163 |
| 65 | NTRK3 | 15 | 88800287-88800464 |
| 66 | OPLAH.9263 | 8 | 145106349-145106456 |
| 67 | PDE3A | 12 | 20522579-20522673 |
| 68 | PDE4B | 1 | 66258534-66258614 |
| 69 | PHF21B | 22 | 45404844-45404938 |
| 70 | PRKCB | 16 | 23847825-23848025 |
| 71 | PROKR2 | 20 | 5296943-5297041 |
| 72 | RASSF2 | 20 | 4803295-4803585 |
| 73 | RBFOX3 | 17 | 77179670-77179722 |
| 74 | RIMS2 | 8 | 104512722-104512817 |
| 75 | SLC35F1 | 6 | 118228394-118228509 |
| 76 | SOX11 | 2 | 5836458-5836545 |
| 77 | SP9 | 2 | 175202025-175202158 |
| 78 | SPSB4 | 3 | 140770490-140770550 |
| 79 | ST6GAL2 | 2 | 107502965-107503050 |
| 80 | ST6GALNAC5 | 1 | 77334012-77334125 |
| 81 | ST8SIA1 | 12 | 22487528-22487620 |
| 82 | ST8SIA6 | 10 | 17495971-17496068 |
| 83 | SYT6 | 1 | 114695394-114695533 |
| 84 | TBX15 | 1 | 119527066-119527655 |
| 85 | TCF24 | 8 | 67874063-67874135 |
| 86 | TCF4 | 18 | 53255304-53255565 |
| 87 | TFPI2 | 7 | 93519404-93519768 |
| 88 | TIAM1 | 21 | 32930771-32930935 |
| 89 | TSHZ3 | 19 | 31839809-31840038 |
| 90 | TSHZ3 | 19 | 31842197-31842291 |
| 91 | VIPR2 | 7 | 158937370-158937481 |
| 92 | VWC2 | 7 | 49813135-49814168 |
| 93 | WBSCR17 | 7 | 70596576-70596675 |
| 94 | ZNF781 | 19 | 38182950-38183127 |

TABLE 3

Primers for DMRs Provided in Table 2.

| DMR No. | Gene | Forward MSP primer (5'-3') | Reverse MSP primer (5'-3') |
|---|---|---|---|
| 1 | ABCB1 | GAT TTT GTT CGT CGT TAG TGC (SEQ ID NO: 1) | TCT CTA AAC CCG CGA ACG A (SEQ ID NO: 2) |
| 5 | AK055957 | TCG GCG TAT TTT TCG TAG ACG C (SEQ ID NO: 3) | CGC AAT CTT AAA CGT ACG CTT CGA (SEQ ID NO: 4) |
| 8 | ARHGEF4 | TGT TTT CGC GGT CGT TAT ATA TTA CGT CGT (SEQ ID NO: 5) | GAA CTA TCC CCG AAC TCC GAC TCG A (SEQ ID NO: 6) |
| 12 | C13orf18 | TTT AGG GAA GTA AAG CGT CGT TTT C (SEQ ID NO: 7) | AAC GAC GTC TCG ATA CCT ACG A (SEQ ID NO: 8) |
| 18 | CD1D | GCG CGT AGC GGC GTT TC (SEQ ID NO: 43) | CCC ATA TCG CCC GAC GTA A (SEQ ID NO: 44) |
| 21 | CLEC11A | AGT TTG GCG TAG TCG GTA GAT C (SEQ ID NO: 9) | GCG CGC AAA TAC CGA ATA AAC G (SEQ ID NO: 10) |
| 24 | DLX4 | GTA TTT TTA ATA TTT GGT GAG TGC G (SEQ ID NO: 11) | TAC TAA AAC GTA CGA TAA ACA TCG T (SEQ ID NO: 12) |
| 25 | ELMO1 | TTA TAT TTT CGT TTT TAG TAA TTC GCG TAG C (SEQ ID NO: 13) | GAA AAC CCG CCG AAA CAT TTC GA (SEQ ID NO: 14) |
| 26 | EMX1 | CGG GTT TTA GCG ATG TTT ATT TTA GTT CGT (SEQ ID NO: 15) | CCT TTT CGT TCG TAT AAA ATT TCG TT (SEQ ID NO: 16) |

TABLE 3-continued

Primers for DMRs Provided in Table 2.

| DMR No. | Gene | Forward MSP primer (5'-3') | Reverse MSP primer (5'-3') |
|---|---|---|---|
| 30 | FER1L4 | TGG AGT TTT TTT CGT CGT TGA CGC (SEQ ID NO: 17) | AAT ACC GCG TCG ACC AAA AAC G (SEQ ID NO: 18) |
| 36 | FRMD4A | TGTAAGCGGTTGGTATTTCGGAAC G (SEQ ID NO: 19) | CAAAAACCTTCGCCCGAACGAA (SEQ ID NO: 20) |
| 41 | GRIN2D | TTA TAT TTT TCG TTT TTA GTA ATT TCG CGT TAG C (SEQ ID NO: 21) | GAA AAC CCG CCG AAA CAT TTC GA (SEQ ID NO: 22) |
| 43 | HOXA1 | TGG GTT ATC GGT TTT TTA AGT TCG G (SEQ ID NO: 23) | GAA TTC CTC CCA ACC AAC CCT CTA CG (SEQ ID NO: 24) |
| 55 | LRRC4 | CGT GGT TGT CGT TTG TAA TAT CGC (SEQ ID NO: 25) | ATA ATC CCC GCT AAC TAA CGA CG (SEQ ID NO: 26) |
| 66 | OPLAH.9263 | TGC GTA GGT GAT AGG GAG GGG TTA C (SEQ ID NO: 27) | ACA AAA CAC ATC CTA TTA ACG CGA A (SEQ ID NO: 28) |
| 70 | PRKCB | GTC GTT TTT GGG CGT TTT AGA GGC (SEQ ID NO: 29) | TAA TCC CAA ACG AAC CGC CG (SEQ ID NO: 30) |
| 77 | SP9 | CGG GGG TAA AAA GGG TAG CGA TAG TGA TAC (SEQ ID NO: 31) | CGA AAA ATT CGA AAC GAA ACG TC (SEQ ID NO: 32) |
| 79 | ST6GAL2 | GTTAGTTTTCGGTCGGGATCGAGC (SEQ ID NO: 33) | CGTTCGTAACGTCGACGATTACCGT A (SEQ ID NO: 34) |
| 81 | ST8SIA1 | GAC GTT TGT CGT CGG GTT CGT TC (SEQ ID NO: 35) | AAA AAC CCT CCG CTA CCA CTT CGC (SEQ ID NO: 36) |
| 84 | TBX15 | CGC GTA GGT CGG ATT GAT TTT TCG T (SEQ ID NO: 37) | TTA ATT AAC GCC CGA ACA CCC GC (SEQ ID NO: 38) |
| 92 | VWC2 | TTG GAG AGT TTT TCG AAT TTT TTC GC (SEQ ID NO: 39) | GAA AAC CAC CCT AAC GCC G (SEQ ID NO: 40) |
| 94 | ZNF781 | TCG TTA GGA ATT AGT GGT TGG ATT TAT CGC (SEQ ID NO: 41) | CGT TCT CTT ATT TTC CGA ATA CGC GAA (SEQ ID NO: 42) |

Example II

Markers were tested on blinded cyst fluid samples from 8 patients with varying degrees of abnormal pancreatic histology. MSP was run on bisulfite converted cyst fluid DNA using 7 of our markers. Copies were normalized to % methylation with LRRC4 as denominator. Results from 4 markers are illustrated in Table 4.

For each of these markers, there is a correlation between the degree of histologic severity and methylation positivity. The adenocarcinoma patient sample (P-1) exhibited the highest % methylation for all markers. Patients P-2, P-3, and P-6 were zero across the board in alignment with the low grade malignant potential of these three histologies. The MCNs and IPMNs light up differentially with PRKCB being the least susceptible to mild to intermediate dysplasia (no high grade IPMNs were available for testing) and CD1D being the most sensitive.

TABLE 4

| | LRRC4 Normalized | | | | |
|---|---|---|---|---|---|
| | ST8SIA1 | CD1D | VWC2 | PRKCB | Clinical Histology |
| P-1 | 23.74 | 112.15 | 84.67 | 65.70 | PDAC with a cystic pattern |
| P-2 | 0.00 | 0.00 | 0.00 | 0.00 | ampullary adeno with adjacent retention cyst |

TABLE 4-continued

| | LRRC4 Normalized | | | | |
|---|---|---|---|---|---|
| | ST8SIA1 | CD1D | VWC2 | PRKCB | Clinical Histology |
| P-3 | 0.00 | 0.00 | 0.00 | 0.00 | serous cystadenoma |
| P-4 | 3.49 | 7.06 | 0.86 | 0.04 | MCN with mild to moderate dysplasia |
| P-5 | 0.00 | 7.52 | 0.00 | 0.00 | MCN with low to intermediate dysplasia |
| P-6 | 0.00 | 0.00 | 0.00 | 0.00 | pseudopapillary tumor |
| P-7 | 8.52 | 15.12 | 22.34 | 0.33 | BD-IPMN intermediate grade dysplasia |
| P-8 | 0.06 | 1.71 | 0.42 | 0.09 | BD-IPMN with low grade dysplasia with focal intermediate dysplasia |

Example III

This example provides the materials, methods, and results for Examples I and II.

Discovery tissue samples (fresh frozen and FFPE) were selected from institutional cancer registries at Mayo Clinic Rochester and were reviewed by an expert pathologist to confirm correct classification. These included pancreas cancer, IPMN, PanIN (P1, P2, and P3), normal pancreas, and normal colon. N=10 to 26 per clinical group and sub-group. 18 normal leukocyte controls were provided by the Mayo Biospecimens Linking Investigators and Clinicians to GIH Cell Signalling Research Clinical Core. Genomic DNA was prepared using Qiagen DNA Mini and Micro Kits RRBS (Reduced Representation Bisulfite Sequencing):

RRBS is a procedure which allows for an unbiased look at the epigenetic or methylation signatures in promoters and CpG islands, regions known to be hypermethylated in cancer cells and hypomethylated in normal cells. A number of the studies we have done are first of a kind—in both cancer type and method of filtering. The criteria we use to identify and rank marker regions is tailored around the end goal of designing clinical methylation specific amplification assays, which makes the process unique. The 4 main filters are 1) DMR calling using defined CpG density criteria and beta regression modeling 2) ROC curve analysis, 3) fold change (with respect to either normal tissue or normal leukocytes), and 4) demonstrated CpG co-methylation over the region (in cases) and lack of co-methylation (in controls).

Library Preparation:

Genomic DNA (300 ng) was fragmented by digestion with 10 Units of MspI, a methylation-specific restriction enzyme which recognizes CpG-containing motifs, to enrich sample CpG content and eliminates redundant areas of the genome. Digested fragments were end-repaired and A-tailed with 5 Units of Klenow fragment (3'-5' exo-), and ligated overnight to methylated TruSeq adapters (Illumina, San Diego Calif.) containing barcode sequences (to link each fragment to its sample ID.) Size selection of 160-340 bp fragments (40-220 bp inserts) was performed using Agencourt AMPure XP SPRI beads/buffer (Beckman Coulter, Brea Calif.). Buffer cutoffs were 0.7×-1.1× sample volumes of beads/buffer. Final elution volume was 22 uL (EB buffer—Qiagen, Germantown Md.); qPCR was used to gauge ligation efficiency and fragment quality on a small sample aliquot. Samples then underwent bisulfite conversion (twice) using a modified EpiTect protocol (Qiagen). qPCR and conventional PCR (PfuTurbo Cx hotstart—Agilent, Santa Clara Calif.) followed by Bioanalyzer 2100 (Agilent) assessment on converted sample aliquots determined the optimal PCR cycle number prior to final library amplification. The following conditions were used for final PCR: 1.) each 50 uL reaction contained 5 uL of 10× buffer, 1.25 uL of 10 mM each deoxyribonucleotide triphosphate (dNTP), 5 uL primer cocktail (~5 uM), 15 uL template (sample), 1 uL PfuTurbo Cx hotstart and 22.75 water; temperatures and times were 95 C-5 min; 98 C-30 sec; 12-16 cycles of 98 C-10 sec, 65 C-30 sec, 72 C-30 sec, 72 C-5 min and 4 C hold, respectively. Samples were combined (equimolar) into 4-plex libraries based on the randomization scheme and tested with the bioanalyzer for final size verification, and with qPCR using phiX standards and adaptor-specific primers.

Sequencing and Bioinformatics: Samples were loaded onto flow cells according to a randomized lane assignment with additional lanes reserved for internal assay controls. Sequencing was performed by the Next Generation Sequencing Core at the Mayo Clinic Medical Genome Facility on the Illumina HiSeq 2000. Reads were unidirectional for 101 cycles. Each flow cell lane generated 100-120 million reads, sufficient for a median coverage of 30-50 fold sequencing depth (read number per CpG) for aligned sequences. Standard Illumina pipeline software called bases and sequenced read generation in the fastq format. SAAP-RRBS, a streamlined analysis and annotation pipeline for reduced representation bisulfate sequencing, was used for sequence alignment and methylation extraction. For the RRBS discovery phase, the primary comparison of interest was the methylation difference—between pancreatic neoplasia cases, pancreas controls, leukocyte controls, and for certain applications colon controls—at each mapped CpG. CpG islands are biochemically defined by an observed to expected CpG ratio>0.6. However, for this model, tiled units of CpG analysis "differentially methylated region (DMR)" were created based on distance between CpG site locations for each chromosome. Islands with only single CpGs were excluded. Individual CpG sites were considered for differential analysis only if the total depth of coverage per disease group was ≥200 reads (an average of 10 reads/subject) and the variance of %-methylation was >0 (non-informative CpGs were excluded). Read-depth criteria were based on the desired statistical power to detect a 10% difference in the %-methylation between any two groups in which the sample size of each group was 18 individuals. Statistical significance was determined by logistic regression of the methylation percentage per DMR, based on read counts. To account for varying read depths across individual subjects, an over-dispersed logistic regression model was used, where dispersion parameter was estimated using the Pearson Chi-square statistic of the residuals from fitted model. DMRs, ranked according to their significance level, were further considered if %-methylation in tissue and leukocyte controls, combined, was ≤1% but ≥10% in cases. This resulted in 94 markers (Table 2). All had AUCs greater than 0.85, signal fold changes greater than 25 (cases v. normal pancreatic tissue) and 5 (cases v. all controls including low and moderate dysplasia samples), and p-values less than 0.001.

Methylation Specific PCR (MSP) Validation:

Candidate markers (usually 20-30 top ranked RRBS DMRs per site) are validated in tissue by methylation specific PCR—first on the discovery samples and subsequently on larger independent sample sets.

MSP Primer Design:

Primers specific for 28 top markers were designed and ordered (IDT, Coralville Iowa). The designs were performed using either Methprimer software (University of California, San Francisco Calif.) or MSPPrimer (Johns Hopkins University, Baltimore, Md.). Assays were tested and optimized by qPCR with SYBR Green on dilutions of universally methylated and unmethylated genomic DNA controls.

Methylation Specific PCR:

Quantitative MSP reactions were performed on the discovery samples to verify performance. Since genome wide next gen sequencing studies can suffer from a high false discovery rate, it is critical to test candidate DMRs on a platform with high analytical sensitivity and specificity. Validation was based on independent micro-dissected tissues from case and control groups and blinded assay of selected markers using methylation specific PCR; marker levels were standardized to methylated LRRC4, a marker for pancreatic epithelia. Case group (n=53) included IPMN-HGD (19), PanIN-3 (4), and PDAC (30). Control group (n=111) included histologically-normal pancreatic tissue (31), IPMN-LGD (36), PanIN-1 (34), and PanIN-2 (10). AUC was calculated for each marker by logistic regression, and discrimination by marker combinations was explored.

An additional validation was performed in cyst fluid samples which were provided from a collaborator at Massachusetts General Hospital in Boston. Eight 200 uL samples (1 pancreatic cancer with a cystic pattern, 1 ampullary adenoma with an adjacent retention cyst, 1 serous cystadenoma, 1 MCN with mild to moderate dysplasia, 1 MCN with low to intermediate dysplasia, 1 pseudopapillary tumor, 1 BD-IPMN with intermediate grade dysplasia, and 1 BD-IPMN with low grade dysplasia with focal intermediate dysplasia). DNA was extracted, bisulfate converted, and run (blinded) by MSP using 10 top marker candidates. LRRC4 normalized results and unblinded clinical information were exchanged simultaneously.

Example IV

This example demonstrates accurate detection of advanced neoplasia in pancreatic cysts with novel DNA methylation markers.

Current clinical algorithms to detect advanced neoplasia (high grade dysplasia (HGD) or cancer) in pancreatic cysts by imaging, with or without cyst fluid (CF) analyses, lack diagnostic accuracy, often resulting in unnecessary surgery. By whole-methylome sequencing of DNA from tissue, experiments identified novel methylated DNA markers that accurately separate cysts harboring HGD or cancer from those with low grade dysplasia (LGD) or no dysplasia. In studies on CF, it was found that a panel of these markers appeared to highly discriminate cysts with advanced neoplasia from those without.

In an expanded multicenter case-control study, experiments were conducted to (1) assess the detection accuracy of advanced neoplasia in pancreatic cysts by assay of novel methylated DNA markers based on blinded CF analyses in cyst cases (HGD or adenocarcinoma) and cyst controls (LGD or no dysplasia) and (2) compare methylated DNA marker distributions in CF with those of CEA and mutant KRAS.

Archival CF samples from surgically resected cysts were studied. CF was obtained by cyst puncture at endoscopic ultrasound or surgery. DNA extracted from 0.2 ml CF (QiaAmp Mini kit, Qiagen, Valencia Calif.) was bisulfite converted (EZ-96 DNA Methylation kit, Zymo Research, Irvine Calif.) and selected methylated DNA markers (BMP3, NDRG4, SP9, DLX4, ABCB1, CD1D, CLEC11A, EMX1, PRKCB, ST8SIA1, VWC2, TBX15, LRRC4, ELMO1) were then assayed by either methylation specific PCR or quantitative allele-specific real-time target and signal amplification (QuARTs). KRAS (7 mutations) was assayed by QuARTs and CEA by a commercial method (MILLIPLEX® MAP Kit) (see, e.g., U.S. Pat. No. 9,127,318).

From 134 pancreatic cysts (41 Intraductal Papillary Mucinous Neoplasm (IPMN), 35 Mucinous Cystic Neoplasm (MCN), 23 Serous Cystadenoma, 13 cystic invasive adenocarcinoma (3 IPMN, 1 MCN, 9 indeterminate precursor), and 22 inflammatory or other cysts, experiments categorized 21 as cases (8 HGD, 13 adenocarcinoma) and 113 as controls (45 no dysplasia, 68 LGD). Median age (IQR) was 71 years (56-77) for cases and 61 years (46-69) for controls (p<0.01); 61% of cases and 31% of controls were men (p=0.034). CF distributions of the 3 top methylated markers (TBX15, BMP3, CLEC11A) illustrate the high discrimination seen between cases and controls (see, FIG. 2). The top 4 methylation markers individually achieved areas under the ROC curve (AUCs)>0.90 (see, Table 5). Case detection was substantially and significantly better by each of these methylated markers than by mutant KRAS or CEA, based on either sensitivities at set specificities or AUCs (see, Table 5). At matched specificities, top individual methylated markers detected twice as many cases as did either mutant KRAS or CEA. Table 6 provides DMR information for BMP3 and NDRG4. Tabled 7 provides primer information for BMP3 and NDRG4.

TABLE 5

Diagnostic accuracy to discriminate cases (HGD/cancer) from controls (LGD, No dysplasia) on pancreatic cyst fluid analysis: Methylated DNA markers compared to mutant KRAS and CEA.

| Cyst Fluid Markers | Sensitivity, (%) | | AUC (95% CI) | P value vs KRAS |
|---|---|---|---|---|
| | At 85% specificity | At 95% specificity | | |
| Methylated DNA | | | | |
| TBX15 | 81 | 76 | 0.92 (0.85-0.99) | 0.002 |
| BMP3 | 81 | 67 | 0.92 (0.85-0.98) | 0.002 |
| CLEC11A | 86 | 67 | 0.91 (0.85-0.97) | 0.002 |
| ST8SIA1 | 86 | 57 | 0.90 (0.84-0.97) | 0.004 |
| CEA | 43 | 29 | 0.72 (0.60-0.84) | 0.906 |
| Mutant KRAS | 48 | 33 | 0.71 (0.57-0.85) | — |

TABLE 6

| DMR No. | Gene Annotation | Chromosome No. | DMR Start-End Positions |
|---|---|---|---|
| 95 | BMP3 | 4 | 81952348-81952402 |
| 96 | NDRG4 | 16 | 58497382-58497492 |

TABLE 7

Primers for DMRs Provided in Table 6.

| DMR No. | Gene | Forward MSP primer (5'-3') | Reverse MSP primer (5'-3') | Probe |
|---|---|---|---|---|
| 95 | BMP3 | GTTTAATTTTCGGTTTCGT CGTC (SEQ ID NO: 45) | CGCTACGAAACACTC CGA (SEQ ID NO: 46) | CGCCGAGGCGGTTTTTTG CG/3C6/ (SEQ ID NO: 49) |
| 96 | NDRG4 | CGGTTTTCGTTCGTTTTTT CG (SEQ ID NO: 47) | CCGCCTTCTACGCGA CTA (SEQ ID NO: 48) | CCACGGACGGTTCGTTTAT CG/3C6/ (SEQ ID NO: 50) |

Example V

This example demonstrates detection of advanced neoplasia in pancreatic cysts by assay of novel DNA methylation markers in cyst fluid.

An important subset of pancreatic cysts harbor advanced neoplasia (high-grade dysplasia (HGD) or cancer). Yet, current diagnostic approaches for detecting this high risk group are based on imaging criteria or cyst fluid analyses which lack accuracy. Management of patients with pancreatic cysts may be further optimized by molecular markers informative for advanced neoplasia. Experiments have recently identified and validated a panel of novel methylated DNA markers (MDMs) in pancreatic tissue that discriminates HGD or adenocarcinoma from low-grade dysplasia (LGD) and non-dysplastic tissue (see, e.g., Majumder S, et al., Gastroenterology 2016; S120-S121). It remains to be determined if this discrimination in tissue holds when applied to cyst fluid. As such, experiments were conducted with an aim to assess and compare distributions of candidate MDMs in cyst fluid from cases with cysts containing advanced neoplasia and from controls with cysts containing either low-grade dysplasia (LGD) or no dysplasia.

In this blinded multicenter study, archival pancreatic cyst fluid was identified from 83 surgically resected cysts. DNA from 0.2 ml cyst fluid was extracted using the QiaAmp Mini kit (Qiagen, Valencia Calif.) and bisulfate converted overnight using the EZ-96 DNA Methylation kit (Zymo Research, Irvine Calif.). Assay of 14 selected MDMs (BMP3, NDRG4, SP9, DLX4, ABCB1, CD1D, CLEC11A, EMX1, PRKCB, ST8SIA1, VWC2, TBX15, LRRC4, ELMO1) was then performed by either methylation specific PCR or quantitative allele-specific real-time target and signal amplification (QuARTs); levels were normalized to beta actin (total DNA) and age. Cases (n=14) were cysts with adenocarcinoma or HGD and controls (n=61) were cysts with LGD or no dysplasia. Cysts with intermediate grade dysplasia (n=8) were analyzed separately.

The top 5 MDMs (BMP3, EMX1, CLEC11A, ST8IA1, VWC2) individually achieved areas under the ROC curve of ≥0.90 to distinguish cases from controls. Cyst fluid level distributions of the 2 top MDMs (BMP3, EMX1) illustrate the high discrimination (see, FIG. 3). At specificity of 90% (95% CI 80-96%), this 2 MDM panel detected 93% (66-100%) of cases. MDM levels in cysts with intermediate grade dysplasia generally fell between HGD and LGD (see, FIG. 3); the 2 MDM panel would have called 38% of these lesions positive at 95% specificity.

Accordingly, such experiments demonstrate that assay of novel MDMs from pancreatic cyst fluid accurately distinguish cases with cancer or HGD from controls with LGD or no dysplasia.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in pharmacology, biochemistry, medical science, or related fields are intended to be within the scope of the following claims.

We claim:

1. A method for characterizing a biological sample comprising:
   measuring a methylation level of a CpG site for twenty-two or fewer genes in a biological sample of a human through
   treating genomic DNA in the biological sample with bisulfite;
   amplifying the bisulfite-treated genomic DNA using a set of primers for each of the selected twenty-two or fewer genes; and
   determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR,
   wherein the twenty-two or fewer genes are selected from BMP3, NDRG4, ABCB1, AK055957, C13ORF18, CD1D, CLEC11A, DLX4, ELMO1, EMX1, FER1L4, FRMD4A, GRIN2D, HOXA1, LRRC4, PRKCB, SP9, ST6GAL2, ST8SIA1, TBX15, VWC2, and ZNF781;
   wherein the twenty-two or fewer genes at least include AK055957 and ST8SIA1;
   wherein the twenty-two or fewer genes at least include one of the following: DLX4, EMX1, FRMD4A, LRRC4, SP9, TBX15, and ZNF781.

2. The method of claim 1 wherein the biological sample comprises pancreatic tissue and/or pancreatic cyst fluid.

3. The method of claim 1 wherein the biological sample comprises a stool sample, a blood sample, and/or a blood fraction sample.

4. The method of claim 1 wherein the primers for the twenty-two or fewer genes are selected from:
   for BMP3 a set of primers consisting of SEQ ID NOS: 45 and 46,
   for NDRG4 a set of primers consisting of SEQ ID NOS: 47 and 48,
   for ABCB1 a set of primers consisting of SEQ ID NOS: 1 and 2,
   for C13ORF18 a set of primers consisting of SEQ ID NOS: 7 and 8,
   for CD1D a set of primers consisting of SEQ ID NOS: 43 and 44,
   for CLEC11A a set of primers consisting of SEQ ID NOS: 9 and 10,
   for DLX4 a set of primers consisting of SEQ ID NOS: 11 and 12,
   for ELMO1 a set of primers consisting of SEQ ID NOS: 13 and 14,
   for EMX1 a set of primers consisting of SEQ ID NOS: 15 and 16,
   for FER1L4 a set of primers consisting of SEQ ID NOS: 17 and 18,
   for FRMD4A a set of primers consisting of SEQ ID NOS: 19 and 20,
   for GRIN2D a set of primers consisting of SEQ ID NOS: 21 and 22,
   for HOXA1 a set of primers consisting of SEQ ID NOS: 23 and 24,
   for LRRC4 a set of primers consisting of SEQ ID NOS: 25 and 26,
   for PRKCB a set of primers consisting of SEQ ID NOS: 29 and 30,
   for SP9 a set of primers consisting of SEQ ID NOS: 31 and 32,
   for ST6GAL2 a set of primers consisting of SEQ ID NOS: 33 and 34,
   for TBX15 a set of primers consisting of SEQ ID NOS: 37 and 38,
   for VWC2 a set of primers consisting of SEQ ID NOS: 39 and 40,
   for ZNF781 a set of primers consisting of SEQ ID NOS: 41 and 42,
   for AK055957 a set of primers consisting of SEQ ID NOS: 3 and 4, and
   for ST8SIA1 a set of primers consisting of SEQ ID NOS: 35 and 36.

5. The method of claim 1, wherein said CpG site is present in a coding region or a regulatory region.

6. The method of claim 1, wherein said measuring the methylation level a CpG site for the twenty-two or fewer genes comprises a determination selected from the group consisting of determining the methylation score of said CpG site and determining the methylation frequency of said CpG site.

7. A method for characterizing a biological sample comprising:
   measuring a methylation level of a CpG site for three or more genes in a biological sample of a human through
   treating genomic DNA in the biological sample with bisulfite;
   amplifying the bisulfite-treated genomic DNA using a set of primers for each of the selected three or more genes; and
   determining the methylation level of the CpG site by methylation-specific PCR, quantitative methylation-specific PCR, methylation-sensitive DNA restriction enzyme analysis, quantitative bisulfite pyrosequencing, or bisulfite genomic sequencing PCR,
   wherein the three or more genes are selected from BMP3, NDRG4, ABCB1, AK055957, C13ORF18, CD1D, CLEC11A, DLX4, ELMO1, EMX1, FER1L4, FRMD4A, GRIN2D, HOXA1, LRRC4, PRKCB, SP9, ST6GAL2, ST8SIA1, TBX15, VWC2, and ZNF781;
   wherein the three or more genes at least include AK055957 and ST8SIA1;
   wherein the three or more genes at least include one of the following:
   DLX4, EMX1, FRMD4A, LRRC4, SP9, TBX15, and ZNF781.

* * * * *

SEQUENCE LISTING

```
<160> NUMBER OF SEQ ID NOS: 50

<210> SEQ ID NO 1
<211> LENGTH: 21
<212> TYPE: DNA
<213> ORGANISM: Artificial Sequence
<220> FEATURE:
<223> OTHER INFORMATION: synthetic

<400> SEQUENCE: 1
gattttgttc gtcgttagtg c                                              21

<210> SEQ ID NO 2
<211> LENGTH: 19
<212> TYPE: DNA
<213> ORGANISM: Artificial Sequence
<220> FEATURE:
<223> OTHER INFORMATION: synthetic

<400> SEQUENCE: 2
tctctaaacc cgcgaacga                                                 19

<210> SEQ ID NO 3
<211> LENGTH: 22
<212> TYPE: DNA
<213> ORGANISM: Artificial Sequence
<220> FEATURE:
<223> OTHER INFORMATION: synthetic

<400> SEQUENCE: 3
tcggcgtatt tttcgtagac gc                                             22

<210> SEQ ID NO 4
<211> LENGTH: 24
<212> TYPE: DNA
<213> ORGANISM: Artificial Sequence
<220> FEATURE:
<223> OTHER INFORMATION: synthetic
```

```
<400> SEQUENCE: 4
cgcaatctta aacgtacgct tcga                                          24

<210> SEQ ID NO 5
<211> LENGTH: 30
<212> TYPE: DNA
<213> ORGANISM: Artificial Sequence
<220> FEATURE:
<223> OTHER INFORMATION: synthetic

<400> SEQUENCE: 5
tgttttcgcg gtcgttatat attacgtcgt                                    30

<210> SEQ ID NO 6
<211> LENGTH: 25
<212> TYPE: DNA
<213> ORGANISM: Artificial Sequence
<220> FEATURE:
<223> OTHER INFORMATION: synthetic

<400> SEQUENCE: 6
gaactatccc cgaactccga ctcga                                         25

<210> SEQ ID NO 7
<211> LENGTH: 25
<212> TYPE: DNA
<213> ORGANISM: Artificial Sequence
<220> FEATURE:
<223> OTHER INFORMATION: synthetic

<400> SEQUENCE: 7
tttagggaag taaagcgtcg ttttc                                         25

<210> SEQ ID NO 8
<211> LENGTH: 22
<212> TYPE: DNA
<213> ORGANISM: Artificial Sequence
<220> FEATURE:
<223> OTHER INFORMATION: synthetic

<400> SEQUENCE: 8
aacgacgtct cgatacctac ga                                            22

<210> SEQ ID NO 9
<211> LENGTH: 22
<212> TYPE: DNA
<213> ORGANISM: Artificial Sequence
<220> FEATURE:
<223> OTHER INFORMATION: synthetic

<400> SEQUENCE: 9
agtttggcgt agtcggtaga tc                                            22

<210> SEQ ID NO 10
<211> LENGTH: 22
<212> TYPE: DNA
<213> ORGANISM: Artificial Sequence
<220> FEATURE:
<223> OTHER INFORMATION: synthetic

<400> SEQUENCE: 10
gcgcgcaaat accgaataaa cg                                            22

<210> SEQ ID NO 11
<211> LENGTH: 25
```

```
<212> TYPE: DNA
<213> ORGANISM: Artificial Sequence
<220> FEATURE:
<223> OTHER INFORMATION: synthetic

<400> SEQUENCE: 11
gtatttttaa tatttggtga gtgcg                                    25

<210> SEQ ID NO 12
<211> LENGTH: 25
<212> TYPE: DNA
<213> ORGANISM: Artificial Sequence
<220> FEATURE:
<223> OTHER INFORMATION: synthetic

<400> SEQUENCE: 12
tactaaaacg tacgataaac atcgt                                    25

<210> SEQ ID NO 13
<211> LENGTH: 34
<212> TYPE: DNA
<213> ORGANISM: Artificial Sequence
<220> FEATURE:
<223> OTHER INFORMATION: synthetic

<400> SEQUENCE: 13 ttatatttt cgtttttagt aatttcgcgt tagc                           34

<210> SEQ ID NO 14
<211> LENGTH: 23
<212> TYPE: DNA
<213> ORGANISM: Artificial Sequence
<220> FEATURE:
<223> OTHER INFORMATION: synthetic

<400> SEQUENCE: 14
gaaaacccgc cgaaacattt cga                                      23

<210> SEQ ID NO 15
<211> LENGTH: 31
<212> TYPE: DNA
<213> ORGANISM: Artificial Sequence
<220> FEATURE:
<223> OTHER INFORMATION: synthetic

<400> SEQUENCE: 15
cgggttttag cgatgtttat tttagtttcg t                             31

<210> SEQ ID NO 16
<211> LENGTH: 26
<212> TYPE: DNA
<213> ORGANISM: Artificial Sequence
<220> FEATURE:
<223> OTHER INFORMATION: synthetic

<400> SEQUENCE: 16
ccttttcgtt cgtataaaat ttcgtt                                   26

<210> SEQ ID NO 17
<211> LENGTH: 24
<212> TYPE: DNA
<213> ORGANISM: Artificial Sequence
<220> FEATURE:
<223> OTHER INFORMATION: synthetic

<400> SEQUENCE: 17
```

```
tggagttttt ttcgtcgttg acgc                                           24
```

<210> SEQ ID NO 18
<211> LENGTH: 22
<212> TYPE: DNA
<213> ORGANISM: Artificial Sequence
<220> FEATURE:
<223> OTHER INFORMATION: synthetic

<400> SEQUENCE: 18

```
aataccgcgt cgaccaaaaa cg                                             22
```

<210> SEQ ID NO 19
<211> LENGTH: 25
<212> TYPE: DNA
<213> ORGANISM: Artificial Sequence
<220> FEATURE:
<223> OTHER INFORMATION: synthetic

<400> SEQUENCE: 19

```
tgtaagcggt tggtatttcg gaacg                                          25
```

<210> SEQ ID NO 20
<211> LENGTH: 22
<212> TYPE: DNA
<213> ORGANISM: Artificial Sequence
<220> FEATURE:
<223> OTHER INFORMATION: synthetic

<400> SEQUENCE: 20

```
caaaaacctt cgcccgaacg aa                                             22
```

<210> SEQ ID NO 21
<211> LENGTH: 34
<212> TYPE: DNA
<213> ORGANISM: Artificial Sequence
<220> FEATURE:
<223> OTHER INFORMATION: synthetic

<400> SEQUENCE: 21

```
ttatatttt cgttttagt aatttcgcgt tagc                                  34
```

<210> SEQ ID NO 22
<211> LENGTH: 23
<212> TYPE: DNA
<213> ORGANISM: Artificial Sequence
<220> FEATURE:
<223> OTHER INFORMATION: synthetic

<400> SEQUENCE: 22

```
gaaacccgc cgaaacattt cga                                             23
```

<210> SEQ ID NO 23
<211> LENGTH: 25
<212> TYPE: DNA
<213> ORGANISM: Artificial Sequence
<220> FEATURE:
<223> OTHER INFORMATION: synthetic

<400> SEQUENCE: 23

```
tgggttatcg gttttttaag ttcgg                                          25
```

<210> SEQ ID NO 24
<211> LENGTH: 26
<212> TYPE: DNA
<213> ORGANISM: Artificial Sequence
<220> FEATURE:
<223> OTHER INFORMATION: synthetic

<400> SEQUENCE: 24
gaattcctcc caaccaaccc tctacg       26

<210> SEQ ID NO 25
<211> LENGTH: 24
<212> TYPE: DNA
<213> ORGANISM: Artificial Sequence
<220> FEATURE:
<223> OTHER INFORMATION: synthetic

<400> SEQUENCE: 25
cgtggttgtc gtttgtaata tcgc       24

<210> SEQ ID NO 26
<211> LENGTH: 23
<212> TYPE: DNA
<213> ORGANISM: Artificial Sequence
<220> FEATURE:
<223> OTHER INFORMATION: synthetic

<400> SEQUENCE: 26
ataatccccg ctaactaacg acg       23

<210> SEQ ID NO 27
<211> LENGTH: 25
<212> TYPE: DNA
<213> ORGANISM: Artificial Sequence
<220> FEATURE:
<223> OTHER INFORMATION: synthetic

<400> SEQUENCE: 27
tgcgtaggtg atagggaggg gttac       25

<210> SEQ ID NO 28
<211> LENGTH: 25
<212> TYPE: DNA
<213> ORGANISM: Artificial Sequence
<220> FEATURE:
<223> OTHER INFORMATION: synthetic

<400> SEQUENCE: 28
acaaaacaca tcctattaac gcgaa       25

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
gtcgtttttg ggcgttttag aggc       24

<210> SEQ ID NO 30
<211> LENGTH: 20
<212> TYPE: DNA
<213> ORGANISM: Artificial Sequence
<220> FEATURE:
<223> OTHER INFORMATION: synthetic

<400> SEQUENCE: 30
taatcccaaa cgaaccgccg       20

<210> SEQ ID NO 31
<211> LENGTH: 30
<212> TYPE: DNA
<213> ORGANISM: Artificial Sequence
<220> FEATURE:
<223> OTHER INFORMATION: synthetic

<400> SEQUENCE: 31
cgggggtaaa aagggtagcg atagtgatac                                    30

<210> SEQ ID NO 32
<211> LENGTH: 23
<212> TYPE: DNA
<213> ORGANISM: Artificial Sequence
<220> FEATURE:
<223> OTHER INFORMATION: synthetic

<400> SEQUENCE: 32
cgaaaaattc gaaacgaaac gtc                                           23

<210> SEQ ID NO 33
<211> LENGTH: 24
<212> TYPE: DNA
<213> ORGANISM: Artificial Sequence
<220> FEATURE:
<223> OTHER INFORMATION: synthetic

<400> SEQUENCE: 33
gttagttttc ggtcgggatc gagc                                          24

<210> SEQ ID NO 34
<211> LENGTH: 26
<212> TYPE: DNA
<213> ORGANISM: Artificial Sequence
<220> FEATURE:
<223> OTHER INFORMATION: synthetic

<400> SEQUENCE: 34
cgttcgtaac gtcgacgatt accgta                                        26

<210> SEQ ID NO 35
<211> LENGTH: 23
<212> TYPE: DNA
<213> ORGANISM: Artificial Sequence
<220> FEATURE:
<223> OTHER INFORMATION: synthetic

<400> SEQUENCE: 35
gacgtttgtc gtcgggttcg ttc                                           23

<210> SEQ ID NO 36
<211> LENGTH: 24
<212> TYPE: DNA
<213> ORGANISM: Artificial Sequence
<220> FEATURE:
<223> OTHER INFORMATION: synthetic

<400> SEQUENCE: 36
aaaaaccctc cgctaccact tcgc                                          24

<210> SEQ ID NO 37
<211> LENGTH: 25
<212> TYPE: DNA
<213> ORGANISM: Artificial Sequence
<220> FEATURE:
<223> OTHER INFORMATION: synthetic

```
<400> SEQUENCE: 37
cgcgtaggtc ggattgattt ttcgt                                           25

<210> SEQ ID NO 38
<211> LENGTH: 23
<212> TYPE: DNA
<213> ORGANISM: Artificial Sequence
<220> FEATURE:
<223> OTHER INFORMATION: synthetic

<400> SEQUENCE: 38
ttaattaacg cccgaacacc cgc                                             23

<210> SEQ ID NO 39
<211> LENGTH: 26
<212> TYPE: DNA
<213> ORGANISM: Artificial Sequence
<220> FEATURE:
<223> OTHER INFORMATION: synthetic

<400> SEQUENCE: 39
ttggagagtt tttcgaattt tttcgc                                          26

<210> SEQ ID NO 40
<211> LENGTH: 19
<212> TYPE: DNA
<213> ORGANISM: Artificial Sequence
<220> FEATURE:
<223> OTHER INFORMATION: synthetic

<400> SEQUENCE: 40
gaaaaccacc ctaacgccg                                                  19

<210> SEQ ID NO 41
<211> LENGTH: 30
<212> TYPE: DNA
<213> ORGANISM: Artificial Sequence
<220> FEATURE:
<223> OTHER INFORMATION: synthetic

<400> SEQUENCE: 41
tcgttaggaa ttagtggttg gatttatcgc                                      30

<210> SEQ ID NO 42
<211> LENGTH: 27
<212> TYPE: DNA
<213> ORGANISM: Artificial Sequence
<220> FEATURE:
<223> OTHER INFORMATION: synthetic

<400> SEQUENCE: 42
cgttctctta ttttccgaat acgcgaa                                         27

<210> SEQ ID NO 43
<211> LENGTH: 17
<212> TYPE: DNA
<213> ORGANISM: Artificial Sequence
<220> FEATURE:
<223> OTHER INFORMATION: synthetic

<400> SEQUENCE: 43
gcgcgtagcg gcgtttc                                                    17

<210> SEQ ID NO 44
```

```
<211> LENGTH: 19
<212> TYPE: DNA
<213> ORGANISM: Artificial Sequence
<220> FEATURE:
<223> OTHER INFORMATION: synthetic

<400> SEQUENCE: 44
cccatatcgc ccgacgtaa                                                19

<210> SEQ ID NO 45
<211> LENGTH: 23
<212> TYPE: DNA
<213> ORGANISM: Artificial Sequence
<220> FEATURE:
<223> OTHER INFORMATION: synthetic

<400> SEQUENCE: 45
gtttaatttt cggtttcgtc gtc                                           23

<210> SEQ ID NO 46
<211> LENGTH: 18
<212> TYPE: DNA
<213> ORGANISM: Artificial Sequence
<220> FEATURE:
<223> OTHER INFORMATION: synthetic

<400> SEQUENCE: 46
cgctacgaaa cactccga                                                 18

<210> SEQ ID NO 47
<211> LENGTH: 21
<212> TYPE: DNA
<213> ORGANISM: Artificial Sequence
<220> FEATURE:
<223> OTHER INFORMATION: synthetic

<400> SEQUENCE: 47
cggttttcgt tcgtttttc g                                              21

<210> SEQ ID NO 48
<211> LENGTH: 18
<212> TYPE: DNA
<213> ORGANISM: Artificial Sequence
<220> FEATURE:
<223> OTHER INFORMATION: synthetic

<400> SEQUENCE: 48
ccgccttcta cgcgacta                                                 18

<210> SEQ ID NO 49
<211> LENGTH: 21
<212> TYPE: DNA
<213> ORGANISM: Artificial Sequence
<220> FEATURE:
<223> OTHER INFORMATION: synthetic

<400> SEQUENCE: 49
cgccgaggcg gttttttgcg c                                             21

<210> SEQ ID NO 50
<211> LENGTH: 22
<212> TYPE: DNA
<213> ORGANISM: Artificial Sequence
<220> FEATURE:
```

```
<223> OTHER INFORMATION: synthetic

<400> SEQUENCE: 50
ccacggacgg ttcgtttatc gc                                              22
```